US008586709B2

(12) United States Patent
Attwood et al.

(10) Patent No.: US 8,586,709 B2
(45) Date of Patent: Nov. 19, 2013

(54) CELL-PERMEABILISING PEPTIDES AND POLYPEPTIDES FOR MICROBIAL CELLS

(75) Inventors: Graeme Trevor Attwood, Ashhurst (NZ); William John Kelly, Ashhurst (NZ); Eric Heinz Altermann, Palmerston North (NZ)

(73) Assignee: Pastoral Greenhouse Research Limited, Wellington (NZ)

( * ) Notice: Subject to any disclaimer, the term of this patent is extended or adjusted under 35 U.S.C. 154(b) by 481 days.

(21) Appl. No.: 12/678,925

(22) PCT Filed: Sep. 25, 2008

(86) PCT No.: PCT/NZ2008/000247
§ 371 (c)(1),
(2), (4) Date: Mar. 24, 2010

(87) PCT Pub. No.: WO2009/041830
PCT Pub. Date: Apr. 2, 2009

(65) Prior Publication Data
US 2010/0209998 A1 Aug. 19, 2010

Related U.S. Application Data

(60) Provisional application No. 60/975,104, filed on Sep. 25, 2007, provisional application No. 60/989,840, filed on Nov. 22, 2007, provisional application No. 60/989,841, filed on Nov. 22, 2007.

(51) Int. Cl.
*C07K 1/00* (2006.01)

(52) U.S. Cl.
USPC .............. 530/350; 424/185.1; 424/191.1; 424/192.1; 424/234.1; 424/93.4; 530/300; 530/355

(58) Field of Classification Search
None
See application file for complete search history.

(56) References Cited

U.S. PATENT DOCUMENTS

| 2003/0219467 | A1 | 11/2003 | Miner et al. | |
|---|---|---|---|---|
| 2003/0233675 | A1* | 12/2003 | Cao et al. | 800/279 |
| 2006/0068386 | A1* | 3/2006 | Slesarev et al. | 435/6 |

FOREIGN PATENT DOCUMENTS

| WO | 9700086 | 1/1997 |
|---|---|---|
| WO | 02077183 A2 | 10/2002 |
| WO | 03038109 | 5/2003 |
| WO | 2006102350 | 9/2006 |

OTHER PUBLICATIONS

Uniprot Database. XP002624903; Accession No. Q07621; Nov. 1, 1996.
Database Geneseq. XP002624904; Accession No. ARW58722; Nov. 13, 2008.
Database Geneseq. XP002624905; Accession No. AEP62342; Mar. 8, 2007.
Database Geneseq. XP002624906; Accession No. ARW59535; Nov. 13, 2008.
Database Uniprot. XP002624907; Accession No. A6Q2N4; Aug. 21, 2007.
Nielsen Henrik et al: "Machine Learning Approaches for the Prediction of Signal Peptides and Other Protein Sorting Signals", Protein Engineering, Oxford University Press, Surrey, GB, vol. 12, No. 1, Jan. 1, 1999, pp. 3-9, XP002419718, ISSN: 0269-2139.
Eichler Jerry: "Archaeal Protein Translocation: Crossing Membranes in the Third Domain of Life", European Journal of Biochemistry, vol. 267, No. 12, Jun. 2000, pp. 3402-3412.
Ring Gabriela et al: "Extreme Secretion: Protein Translocation Across The Archael Plasma Membrane.", Journal of Bioenergetics and Biomembranes Feb. 2004 LNKD-PUBMED:15168608, vol. 36, No. 1, Feb. 2004, pp. 35-45.
Attwood G T et al: "Analysis of the *Methanobrevibacter ruminantium* Draft Genome: Understanding Methanogen Biology to Inhibit Their Action in the Rumen", Australian Journal of Experimental Agriculture, Csiro, Collingwod, AU, vol. 48, No. 1-2, Jan. 1, 2008, pp. 83-88.
Leahy Sinead C et al: "The Genome Sequence of the Rumen Methanogen *Methanobrevibacter ruminantium* Reveals New Possibilities for Controlling Ruminant Methane Emissions", Plos One, vol. 5, No. 1, Jan. 2010, pp. E8926, 1-17.
Database Uniprot. XP002624910; Accession No. A5UKP9. Jul. 10, 2007.
Database Uniprot. XP002624911; Accession No. A2SRW5. Mar. 6, 2007.
Database Uniprot. XP002624912; Accession No. A5UK85. Jul. 10, 2007.
Database Uniprot. XP002624913; Accession No. Q6L0M1. Jul. 5, 2004.
Database Uniprot. XP002624914; Accession No. O26731. Jan. 1, 1998.
Database Uniprot. XP002624915; Accession No. A5UN37. Jul. 10, 2007.
Database Uniprot. XP002624916; Accession No. A5UMP9. Jul. 10, 2007.
European Search Report corresponding to related EP Application No. 08834203.5; Mailed Mar. 11, 2011.
Database Genbank. XP008135722; Accession No. ZP_01872031. Jun. 8, 2007.
Samuel B.S. et al. "Genomic and Metabolic Adaptations of *Methanobrevibacter smithii* to the Human Gut". PNAS, 104(25), Jun. 19, 2007, pp. 10643-10648.
Smith D.R. et al. "Complete Genome Sequence of *Methanobacterium thermoautotrophicum* Deltah: Functional Analysis and Comparative Genomics". Journal of Bacteriology, 179(22), 1997, pp. 7135-7155.
Database Genbank. XP008135796; Accession No. ABN07071. Jan. 26, 2007.

(Continued)

*Primary Examiner* — Jennifer Graser
(74) *Attorney, Agent, or Firm* — Loeb & Loeb LLP

(57) ABSTRACT

Signal peptides and polypeptides from *Methanobrevibacter ruminantium*, a methanogenic archaea present in ruminants. Methods of using these peptides to permeabilise microbial cells, particularly *M. ruminantium* strain M1$^\tau$ (DSM 1093).

15 Claims, 35 Drawing Sheets

(56) References Cited

OTHER PUBLICATIONS

Database Genbank. XP008135794; Accession No. AAT43481. Feb. 6, 2004.
Database Genbank. XP008135795; Accession No. ABG93799. Jul. 24, 2006.
Database Genbank. XP008135793; Accession No. DQ419923. Feb. 28, 2006.
Database Genbank. XP008135727; Accession No. ZP_03607371. Oct. 27, 2008.
Database Genbank. XP008135724; Accession No. ZP_03608221. Oct. 27, 2008.
Database Genbank. XP008135726; Accession No. ZP_03608385. Oct. 27, 2008.
Database Genbank. XP008135725; Accession No. ZP_03608088. Oct. 27, 2008.
International Preliminary Patentability Report corresponding to related PCT Application No. PCT/NZ2008/000247; Mailed Oct. 26, 2009.

* cited by examiner

FIG. 1A

Comparison of Methanobacteriales genomes

| Methanogen | Mb | ORFs | %G+C | rRNAs | tRNAs |
|---|---|---|---|---|---|
| *Methanobrevibacter ruminantium* M1[a] | 2.9 | 2239 | 32.6 | 2 | 59 |
| *Methanobrevibacter smithii* PS[b] | 1.9 | 1795 | 31.0 | 2 | 34 |
| *Methanothermobacter thermoautotrophicus* ΔH[c] | 1.8 | 1873 | 49.5 | 2 | 39 |
| *Methanosphaera stadtmanae* DSM3091[d] | 1.8 | 1534 | 27.6 | 4 | 40 |

[a] genome size and number of ORFs are based on analysis of the single contig *M. ruminantium* draft genome sequence
[b] Samuel et al., 2007
[c] Smith et al., 1997
[d] Fricke et al., 2006

FIG. 1B

*M. ruminantium* draft genome statistics

| | |
|---|---|
| Genome size (bp) | 2937347 |
| Open reading frames | 2239 |
| Proteins with trans-membrane domains | 503 (22.5) |
| Terminator structures | 334 (14.9) |
| TIGRfams | 2304 |
| Pfams | 3315 |
| COGs | 1834 |

[a] Numbers in parentheses indicate the feature as a % of the total ORF number

FIG. 2-1

| GENE NAME | SIGNAL SEQUENCE | SEQ ID NO: |
|---|---|---|
| Contig40_gene_70 | ---------MRKEIISILVIAIIAISVIPTAFS--------- | 9 |
| Contig49_gene_208 | ---------MDKKIIIGAVVALLVI--IVGA----------- | 162 |
| Contig40_gene_867 | ---------MRKEILIAAIAIILIL--CGGVFA--------- | 65 |
| Contig47_gene_125 | ---------MDKKMIVSVAFLLLIL--AVALVSVFDESNS-- | 130 |
| Contig47_gene_391 | ---------MDKKMTVLLVALFCLL--CVG--S--------- | 146 |
| Contig40_gene_34 | ---------MVLALSIILLSSIAAASA-------------- | 1 |
| Contig45_gene_106 | ------MKFKNSHILLVSLISIFLLLSISAAASA-------- | 121 |
| Contig45_gene_36 | ------MFKVSKSILIVCLVSLFLLVSQASA----------- | 111 |
| Contig55_gene_23 | ----MLLNDKSELLKSLSILFLLIVLITSFNSVYA------- | 170 |
| Contig40_gene_231 | -----MKKNLSLKNILLILSLIFLFVLSIGSSFA-------- | 23 |
| Contig40_gene_1099 | ------MNFKKLLMISLILLFVLSVGFSTASA---------- | 87 |
| Contig40_gene_1254 | -------MKFNSRVLGILSLLFVLTILVSSVGA--------- | 96 |
| Contig40_gene_39 | ----------MDN--KKIFVIVALAL-LAIVAVGSVS-A--- | 3 |
| Contig40_gene_40 | ----------MNN--KKIFAIAALAI-IAIVAVGSVS-A--- | 4 |
| Contig40_gene_41 | ----------MNA--KKLTILAALAI-LAIVAVGSVS-A--- | 5 |
| Contig40_gene_1036 | ----------MNN--KKIFV-AGLAI-LAIVLMGSVA----- | 79 |
| Contig40_gene_732 | ----------MDS--KKLILVTALAF-LAIVSIASVS-A--- | 47 |
| Contig40_gene_1215 | ----------MDS--KKILMIAVVAL-IAIVAVSSCS-A--- | 93 |
| Contig47_gene_146 | ----------MDS--KKILVIIGLTV-LAIFLASSVS-A--- | 132 |
| Contig40_gene_964 | ----------MSI--KRILLTSLMLF-IIIFSISFVS-A--- | 71 |
| Contig40_gene_1274 | ----------MKN--KSLILISLILI-ITIISIGSVV-A--- | 98 |
| Contig40_gene_1350 | ----------MN---KKIILSLLLVL-LVAISVSAVA-A--- | 101 |
| Contig40_gene_1355 | ----------MNN--KKIIMSFLIVL-LIAISVSAVS-A--- | 103 |
| Contig47_gene_381 | ----------MKF--KKYLFILLIAL-ICIISVSAVA----- | 145 |
| Contig40_gene_203 | -----MKTNLKKTTIILALLMAILLSIGAIS-A--------- | 21 |
| Contig40_gene_837 | ---------MK--LKKFSVILAVLL-VAILAIGAVS-A---- | 61 |
| Contig40_gene_553 | ---------MK---KKIAIILGIAL-LAFLVIGASS-A---- | 43 |
| Contig45_gene_116 | ---------MNS--KKIAIVLGIIL-LSFAIVGSAS-A---- | 122 |
| Contig40_gene_834 | ---------MNS--NKTYAVLGLLL-LLILSIGAIS-A---- | 58 |
| Contig40_gene_105 | -------MNINLKKITFLCLVLVLIGLISFNSIS-A------ | 12 |
| Contig40_gene_45 | -------MKINLKRV-ILGIILLICISSASIIS-A------- | 172 |
| Contig55_gene_228 | -------MNSKGKYL-VLFLILILS-FSIISASF-A------ | 22 |

FIG. 2-2

| GENE NAME | SIGNAL SEQUENCE | SEQ ID NO: |
|---|---|---|
| Contig40_gene_269 | ----------M--KRRYK-VLFLLAILT-IISINAIS-A------- | 29 |
| Contig40_gene_815 | ----------------------MILAILL-AVGMTLTAVS-A--- | 55 |
| Contig49_gene_184 | -------------MKNKAMFLISALLI-AVILSLSAVS-AADDAIA | 160 |
| Contig40_gene_63 | -------------MNKVQLSSILALVL-ILFLSLAVVS-A----- | 8 |
| Contig40_gene_187 | -------------MFNKKMVLAISLLA-VIFASMCIVS-A----- | 20 |
| Contig47_gene_197 | ---------------------MLISVLG-VIVIIMVVA-A----- | 134 |
| Contig40_gene_352 | --------------------MKK-SVFKILIALA-LILLAVSIVS-S | 36 |
| Contig47_gene_13 | --------------------MNKQNVF-ALILLT-IILLSVVAVS-- | 125 |
| Contig40_gene_841 | ----------------------MILISLI-LVILSISCVS-A--- | 62 |
| Contig49_gene_239 | -------------MLIMAI-LVLLTMASVS-ASELEDIQVT | 164 |
| Contig40_gene_1074 | ------------MEKTMKSKLFLLIII-SILISISSVS-A----- | 80 |
| Contig40_gene_1238 | ------------MK--LKSKYFVFLLII-CILFSISTVS-A---- | 94 |
| Contig47_gene_7 | ------------MMRKTIFGVIFIV-FILFSISTVS-A------- | 124 |
| Contig40_gene_232 | -----------MKRNIYFIILLVT-LFLISMSVVS-A-------- | 40 |
| Contig40_gene_930 | ----------MKPLIIKISIFCNKKIFIFTIMI-VMLLSLAAVS-A | 70 |
| Contig49_gene_175 | ----------MLNRKALIFSLIV-LFMLSISAVS-A--------- | 157 |
| Contig40_gene_1084 | ----------MD-KKIFIVSFIL-LAIFTIGAVG-A--------- | 81 |
| Contig40_gene_1089 | ---------MVIMNNKKLFIVSLII-LTILTIGAVS-A------- | 83 |
| Contig40_gene_1088 | ---------MMKMTKKNLFLISLIL-LIILTIGAVS-A------- | 82 |
| Contig49_gene_167 | ---------MNNKTLFIIGLFI-CLLFFTIPMVS-A--------- | 155 |
| Contig40_gene_824 | --------MNKRI----FLYIALIFI-ISLLSFSAVS-A------ | 56 |
| Contig47_gene_375 | --------LTFNNLRINIKDCMVIFVVFT-VLLISIIAVS-A--- | 144 |
| Contig40_gene_1158 | --------MKVLK-----IAIML-ILIISLGAVS-A--------- | 90 |
| Contig49_gene_43 | --------MRLRY-----FAIISL-ILLIFLVPVSFA-------- | 150 |
| Contig45_gene_91 | --------MEIRYKNLLKVFTIFL-VLLISCGFAS-A-------- | 115 |
| Contig45_gene_93 | --------MKIRYKNLLKVFTIFL-VLLISCGFAS-A-------- | 116 |
| Contig40_gene_164 | --------MIVTTICVILILIVLFYGLFPGLTNS----------- | 16 |
| Contig40_gene_1364 | --------MKIQRGIYIYILTLLVLFS--LSAASAA--------- | 104 |
| Contig47_gene_57 | --------MLNKKIIILTFLILS--ISSASASA------------ | 126 |
| Contig55_gene_40 | --------MKKIILGTCILFLL--ISVAYA--------------- | 171 |
| Contig40_gene_1029 | -------MRNPKDYIMKTDYLIILMALLIS--IVSPIAA------ | 78 |
| Contig40_gene_169 | -------LKSDKRAKFAIFFSIAIALG--LSNIAA---------- | 18 |
| Contig47_gene_304 | --------------VILILFLA--VSTVAA--------------- | 138 |
| Contig40_gene_346 | -------LS--------MEDNLLKNRKLILISIFLVSLLA--ISAVSA | 34 |
| Contig40_gene_872 | -----------------MLISIVLISLIA--LGAVSA-------- | 66 |
| Contig40_gene_750 | -----------------MISLLLISILA--ISAASAA-------- | 50 |
| Contig40_gene_1008 | ---------------MILISLFLISLLA--IGAASA--------- | 75 |
| Contig40_gene_501 | --------MKLNKFFIISILLIFLS--ISAISA------------ | 42 |

FIG. 2-3

| GENE NAME | SIGNAL SEQUENCE | SEQ ID NO: |
|---|---|---|
| Contig40_gene_1021 | ----------------MKLYKNSIIILLLILLILS--IGAAAA-------- | 76 |
| Contig40_gene_721 | ------------------MK----RSIIFLTIILSLFLV--IGYASA-------- | 45 |
| Contig40_gene_1093 | ---------------MKFNKNRGISAISIILILFLS--ISMASA-------- | 84 |
| Contig40_gene_1097 | ------------VFILKFEIKRSLIFISILAILILS--IGMASA-------- | 85 |
| Contig40_gene_1176 | ---------------MNFKTKGSLILISLLFLILIG--IGMASA-------- | 91 |
| Contig40_gene_72 | ------------MNKKRFKLLLTIFIAFALINTCFILNDNLS-------- | 10 |
| Contig49_gene_25 | ---------------MRKKILFLTLMLLICFTLNSVCA-------- | 149 |
| Contig40_gene_411 | ------------------M--KKNIFLIAILLIAVVAVSGC-------- | 37 |
| Contig49_gene_152 | ---------------MDKKTLAIIAITVIALVAVG---------- | 154 |
| Contig40_gene_636 | ------------MNFNKKILLIIALVFIASVGIVAA---------- | 44 |
| Contig40_gene_1351 | ---------MSLSIFVLVIGGGFINKRILLIFVFLIFFISIGSVVA---------- | 102 |
| Contig49_gene_194 | --------MKF---------NKSLIAIFVILIVAFSSISVIA---------- | 161 |
| Contig40_gene_909 | ---------------MKNWKIIGLILILILLAVVSV--SG---------- | 69 |
| Contig40_gene_996 | ------------MKISRII-LILLFVVFFEIGLFSSYTIVNA---------- | 74 |
| Contig40_gene_835 | ------------MINKRIISLSLLIIIIVFLIIG--LSAVSA---------- | 59 |
| Contig40_gene_349 | ------------MNRN----KIIVLVLLIAVVGFTMGPACA---------- | 35 |
| Contig47_gene_140 | ------------MKIS----RIIVLLMILI-----FTAGMVYA---------- | 131 |
| Contig40_gene_1104 | ------------MKIKKS----FVILCLICL-----FTIASVAA---------- | 88 |
| Contig47_gene_62 | ---------VFSVSLNKLKIG----RVFICLFILV-----FISCSINCVFA---------- | 128 |
| Contig40_gene_828 | ------------MKYN----KKIFFLFLLCL-----IIPQAIY---------- | 57 |
| Contig40_gene_1247 | ------------MNYS----IIIFIFLMDAL--VLMASIQVCGA---------- | 95 |
| Contig40_gene_1198 | ------------MG------KFKFIFILVLAI--FLICGIA---------- | 92 |
| Contig40_gene_1098 | MQAIIPVKDNFLILVTNMKKSDFK----RIFICLVLLTCL--IGAVSA---------- | 86 |
| Contig49_gene_44 | ---------------MFIGLLLIGLL--IIPISFA---------- | 151 |
| Contig40_gene_836 | ------------MD-FKK-----AIPLFALLLLIL--FIIGSSSA---------- | 60 |
| Contig49_gene_183 | ---------MSYFNKGHIWNILLICILLIGTL--AMMGSASA---------- | 159 |
| Contig40_gene_847 | ------------MDNSNII-ISVIIVLCIAAGVTA---------- | 63 |
| Contig40_gene_848 | ------------MDNSSIL-ISVIIVLCIAAGVTA---------- | 64 |
| Contig40_gene_766 | ---------MLKTKLCGISLKNPLMLAAGVLGSHA---------- | 52 |
| Contig45_gene_64 | ---------MKITVAGVGYVGLSLAVLLAQKHDVTA---------- | 113 |
| Contig45_gene_89 | ------MNLMKITVAGVGYVGLSIAILLAQKHDVTA---------- | 114 |
| Contig55_gene_4 | ---------MFIVILLFAFIVIGGSYSVFA---------- | 167 |

KKLIILLLLILLLSI
SEQ ID NO:117

Fluorescein-KKKLIILLLLLLLLSI
SEQ ID NO:118

FIG. 6-1

| Gene Number | Annotation | SignalP-HMM SP probability score | | | SignalP-NN Y-score & predicted cleavage site | | | |
|---|---|---|---|---|---|---|---|---|
| | | Gram+ | Gram- | Euk | Gram+ | Gram- | Euk | |
| Contig40_gene_34 | hypothetical protein | 0.931 | 0.998 | 1 | 0.655 | 0.534 | 0.886 | 19 |
| Contig40_gene_35 | LcmA family protein | 0.839 | 0.635 | 0.207 | 0.122 | 0.083 | 0.472 | 19 |
| Contig40_gene_39 | hypothetical protein | 0.999 | 1 | 0.991 | 0.736 | 0.737 | 0.748 | 26 |
| Contig40_gene_40 | hypothetical protein | 1 | 1 | 0.99 | 0.698 | 0.704 | 0.819 | 26 |
| Contig40_gene_41 | hypothetical protein | 1 | 1 | 0.999 | 0.601 | 0.745 | 0.8 | 26 |
| Contig40_gene_51 | adhesin-like protein | 0.017 | 0.016 | 0.938 | 0.433 | 0.338 | 0.448 | 23 |
| Contig40_gene_54 | hypothetical protein | 0.848 | 0 | 0.057 | 0.363 | 0.162 | 0.631 | 17 |
| Contig40_gene_63 | adhesin-like protein | 1 | 1 | 0.997 | 0.775 | 0.621 | 0.92 | 26 |
| Contig40_gene_70 | hypothetical protein | 1 | 0.999 | 0.892 | 0.807 | 0.633 | 0.789 | 25 |
| Contig40_gene_72 | hypothetical protein | 1 | 0.971 | 0.59 | 0.612 | 0.406 | 0.484 | 25 |
| Contig40_gene_75 | hypothetical protein | 0.048 | 0.143 | 0.996 | 0.338 | 0.2 | 0.41 | 23 |
| Contig40_gene_105 | adhesin-like protein | 1 | 1 | 0.816 | 0.789 | 0.739 | 0.726 | 29 |
| Contig40_gene_119 | molybdopterin-guanine dinucleotide biosynthesis protein A MobA | 0.007 | 0.582 | 0.012 | 0.483 | 0.279 | 0.39 | 31 |
| Contig40_gene_161 | hypothetical protein | 0.914 | 0.982 | 0.174 | 0.278 | 0.199 | 0.439 | 34 |
| Contig40_gene_163 | 2-dehydropantoate 2-reductase PanE | 0.736 | 0.941 | 0.114 | 0.323 | 0.161 | 0.249 | 14 |
| Contig40_gene_164 | hypothetical protein | 0.824 | 0.828 | 0.675 | 0.362 | 0.469 | 0.843 | 28 |
| Contig40_gene_165 | hypothetical protein | 0.292 | 0.56 | 0.282 | 0.348 | 0.388 | 0.624 | 26 |
| Contig40_gene_169 | hypothetical protein | 0.991 | 0.998 | 0.958 | 0.448 | 0.314 | 0.462 | 28 |
| Contig40_gene_179 | hypothetical protein | 0.709 | 0.522 | 0.128 | 0.38 | 0.119 | 0.149 | 42 |
| Contig40_gene_187 | hypothetical protein | 1 | 1 | 0.994 | 0.766 | 0.551 | 0.699 | 26 |
| Contig40_gene_203 | adhesin-like protein | 1 | 1 | 0.971 | 0.652 | 0.684 | 0.848 | 29 |
| Contig40_gene_228 | SNase domain-containing protein | 1 | 1 | 0.95 | 0.717 | 0.754 | 0.696 | 24 |
| Contig40_gene_231 | adhesin-like protein | 1 | 1 | 0.98 | 0.677 | 0.814 | 0.699 | 29 |
| Contig40_gene_232 | adhesin-like protein with cysteine protease domain | 1 | 1 | 0.989 | 0.77 | 0.704 | 0.802 | 25 |
| Contig40_gene_248 | hypothetical protein | 0.721 | 0.346 | 0.112 | 0.244 | 0.295 | 0.185 | 22 |
| Contig40_gene_251 | hypothetical protein | 0.769 | 0.931 | 0.099 | 0.514 | 0.635 | 0.939 | 21 |
| Contig40_gene_252 | hypothetical protein | 0.408 | 0.929 | 0.991 | 0.603 | 0.851 | 0.85 | 32 |
| Contig40_gene_260 | hypothetical protein | 0.014 | 0.457 | 0.854 | 0.628 | 0.428 | 0.584 | 28 |
| Contig40_gene_296 | adhesin-like protein | 1 | 1 | 0.988 | 0.48 | 0.546 | 0.826 | 25 |
| Contig40_gene_297 | hypothetical protein | 0.605 | 0.045 | 0.381 | 0.207 | 0.085 | 0.407 | 13 |
| Contig40_gene_306 | UDP-glucose pyrophosphorylase GalU | 0.999 | 0.99 | 0.372 | 0.385 | 0.827 | 0.491 | 15 |
| Contig40_gene_317 | geranylgeranyl reductase family protein | 0.022 | 0.107 | 0.661 | 0.494 | 0.458 | 0.427 | 29 |
| Contig40_gene_346 | adhesin-like protein | 0.458 | 0.954 | 0.446 | 0.808 | 0.451 | 0.746 | 22 |
| Contig40_gene_349 | hypothetical protein | 1 | 1 | 0.854 | 0.499 | 0.755 | 0.851 | 30 |
| Contig40_gene_352 | hypothetical protein | 0.999 | 1 | 0.994 | 0.939 | 0.947 | 0.647 | 27 |
| Contig40_gene_411 | hypothetical protein | 1 | 1 | 0.995 | 0.5 | 0.402 | 0.843 | 25 |
| Contig40_gene_431 | signal peptidase I | 0.881 | 0.986 | 0.973 | 0.406 | 0.184 | 0.748 | 22 |
| Contig40_gene_448 | peptidase S49 family | 0.426 | 0.855 | 0.999 | 0.466 | 0.302 | 0.744 | 23 |
| Contig40_gene_466 | hypothetical protein | 0.875 | 0.884 | 0.003 | 0.26 | 0.086 | 0.61 | 19 |
| Contig40_gene_483 | ABC transporter substrate-binding protein | 0.966 | 0.488 | 0.044 | 0.715 | 0.321 | 0.549 | 31 |
| Contig40_gene_501 | adhesion-like protein | 1 | 0.999 | 0.47 | 0.346 | 0.471 | 0.862 | 17 |
| Contig40_gene_553 | ABC transporter substrate-binding protein | 1 | 1 | 0.97 | 0.632 | 0.716 | 0.921 | 25 |
| | | | | 0.993 | 0.671 | 0.564 | 0.59 | 24 |

FIG. 6-2

| Gene ID | Description | | | | | | | | | |
|---|---|---|---|---|---|---|---|---|---|---|
| Contig40_gene_636 | hypothetical protein | 1 | 1 | 0.981 | 0.613 | 27 | 0.749 | 24 | 0.926 | 25 |
| Contig40_gene_721 | ABC transporter substrate-binding protein | 0.991 | 1 | 0.988 | 0.756 | 24 | 0.851 | 24 | 0.907 | 24 |
| Contig40_gene_730 | CBS domain-containing protein | 0.026 | 0.533 | 0.862 | 0.232 | 40 | 0.099 | 42 | 0.248 | 33 |
| Contig40_gene_732 | hypothetical protein | 0.999 | 1 | 0.996 | 0.754 | 26 | 0.68 | 26 | 0.771 | 26 |
| Contig40_gene_733 | hypothetical protein | 0.448 | 0.881 | 0.97 | 0.455 | 36 | 0.396 | 36 | 0.432 | 25 |
| Contig40_gene_749 | hypothetical protein | 0.251 | 0.988 | 1 | 0.284 | 31 | 0.281 | 30 | 0.353 | 21 |
| Contig40_gene_750 | adhesin-like protein | 0.991 | 1 | 1 | 0.544 | 18 | 0.761 | 18 | 0.863 | 18 |
| Contig40_gene_762 | DGC domain-containing protein | 0.02 | 0.674 | 0.232 | 0.428 | 31 | 0.263 | 31 | 0.09 | 31 |
| Contig40_gene_766 | dihydroorotate dehydrogenase PyrD | 0.88 | 0.977 | 0.921 | 0.321 | 38 | 0.569 | 27 | 0.305 | 27 |
| Contig40_gene_769 | coenzyme A biosynthesis bifunctional protein CoaBC | 0 | 0.001 | 0.505 | 0.369 | 36 | 0.361 | 35 | 0.716 | 29 |
| Contig40_gene_787 | energy-converting hydrogenase B subunit H EhbH | 0 | 0 | 0.669 | 0.296 | 34 | 0.169 | 30 | 0.471 | 22 |
| Contig40_gene_815 | hypothetical protein | 0.958 | 0.995 | 1 | 0.454 | 19 | 0.402 | 18 | 0.821 | 19 |
| Contig40_gene_824 | adhesin-like protein | 1 | 1 | 0.982 | 0.819 | 26 | 0.767 | 26 | 0.909 | 26 |
| Contig40_gene_828 | cobaltochelatase CobN subunit | 1 | 1 | 0.996 | 0.477 | 25 | 0.911 | 25 | 0.94 | 25 |
| Contig40_gene_834 | adhesin-like protein | 1 | 1 | 0.993 | 0.834 | 26 | 0.674 | 26 | 0.853 | 26 |
| Contig40_gene_835 | adhesin-like protein | 1 | 1 | 0.962 | 0.786 | 34 | 0.545 | 28 | 0.942 | 28 |
| Contig40_gene_836 | adhesin-like protein | 1 | 1 | 0.999 | 0.595 | 26 | 0.791 | 26 | 0.874 | 26 |
| Contig40_gene_837 | adhesin-like protein | 1 | 1 | 0.999 | 0.828 | 26 | 0.628 | 26 | 0.886 | 26 |
| Contig40_gene_841 | adhesin-like protein | 0.903 | 0.992 | 1 | 0.461 | 19 | 0.578 | 19 | 0.905 | 19 |
| Contig40_gene_847 | adhesin-like protein | 0.919 | 0.895 | 0.899 | 0.416 | 25 | 0.548 | 23 | 0.877 | 23 |
| Contig40_gene_848 | hypothetical protein | 0.965 | 0.99 | 0.965 | 0.498 | 25 | 0.603 | 23 | 0.878 | 23 |
| Contig40_gene_867 | hypothetical protein | 0.999 | 1 | 0.992 | 0.384 | 26 | 0.531 | 23 | 0.872 | 23 |
| Contig40_gene_872 | adhesin-like protein | 1 | 0.999 | 1 | 0.717 | 25 | 0.426 | 19 | 0.85 | 19 |
| Contig40_gene_900 | signal peptidase I | 0.206 | 0.065 | 0.955 | 0.461 | 22 | 0.109 | 21 | 0.189 | 22 |
| Contig40_gene_906 | hypothetical protein | 0.779 | 0.299 | 0.947 | 0.278 | 22 | 0.188 | 22 | 0.206 | 20 |
| Contig40_gene_909 | ribonuclease | 1 | 0.998 | 0.988 | 0.409 | 27 | 0.244 | 26 | 0.772 | 23 |
| Contig40_gene_930 | adhesin-like protein | 1 | 1 | 0.743 | 0.554 | 35 | 0.616 | 34 | 0.914 | 35 |
| Contig40_gene_964 | adhesin-like protein | 1 | 1 | 0.984 | 0.799 | 26 | 0.862 | 26 | 0.891 | 26 |
| Contig40_gene_975 | glycerol-3-phosphate dehydrogenase (NAD) | 0.04 | 0.851 | 0.837 | 0.497 | 31 | 0.389 | 25 | 0.614 | 25 |
| Contig40_gene_982 | hypothetical protein | 0.964 | 0.526 | 0.263 | 0.177 | 28 | 0.242 | 20 | 0.464 | 20 |
| Contig40_gene_996 | hypothetical protein | 0.967 | 0.846 | 1 | 0.636 | 31 | 0.379 | 31 | 0.714 | 31 |
| Contig40_gene_1008 | adhesin-like protein | 0.999 | 1 | 1 | 0.611 | 21 | 0.436 | 21 | 0.775 | 21 |
| Contig40_gene_1021 | adhesin-like protein with cysteine protease domain | 1 | 1 | 0.99 | 0.573 | 25 | 0.763 | 24 | 0.911 | 25 |
| Contig40_gene_1025 | adhesin-like protein | 0.217 | 0.413 | 0.999 | 0.299 | 31 | 0.315 | 23 | 0.24 | 23 |
| Contig40_gene_1029 | hypothetical protein | 0.999 | 1 | 0.782 | 0.645 | 32 | 0.511 | 32 | 0.8 | 32 |
| Contig40_gene_1036 | hypothetical protein | 1 | 1 | 0.99 | 0.495 | 25 | 0.692 | 25 | 0.727 | 24 |
| Contig40_gene_1074 | adhesin-like protein | 1 | 1 | 0.984 | 0.696 | 28 | 0.774 | 28 | 0.88 | 28 |
| Contig40_gene_1084 | adhesin-like protein | 0.999 | 0.999 | 0.985 | 0.565 | 24 | 0.764 | 24 | 0.793 | 24 |
| Contig40_gene_1088 | adhesin-like protein | 1 | 1 | 0.997 | 0.737 | 28 | 0.852 | 28 | 0.87 | 28 |
| Contig40_gene_1089 | adhesin-like protein | 1 | 1 | 0.984 | 0.684 | 28 | 0.883 | 28 | 0.809 | 28 |
| Contig40_gene_1093 | adhesin-like protein | 1 | 1 | 0.983 | 0.808 | 28 | 0.809 | 28 | 0.891 | 28 |
| Contig40_gene_1097 | adhesin-like protein | 1 | 1 | 0.875 | 0.824 | 31 | 0.734 | 31 | 0.823 | 31 |
| Contig40_gene_1098 | adhesin-like protein | 0.998 | 0.999 | 0.849 | 0.364 | 43 | 0.308 | 43 | 0.835 | 43 |
| Contig40_gene_1099 | adhesin-like protein | 1 | 1 | 0.998 | 0.803 | 27 | 0.905 | 27 | 0.887 | 27 |
| Contig40_gene_1104 | adhesin-like protein | 1 | 1 | 0.992 | 0.624 | 25 | 0.615 | 24 | 0.89 | 25 |

FIG. 6-3

| | | | | | | | | |
|---|---|---|---|---|---|---|---|---|
| Contig40_gene_1106 | hypothetical protein | 0.206 | 0.937 | 0.842 | 0.34 | 35 | 0.228 | 26 | 0.375 | 24 |
| Contig40_gene_1158 | adhesin-like protein with cysteine protease domain | 0.991 | 1 | 0.998 | 0.781 | 23 | 0.46 | 23 | 0.929 | 23 |
| Contig40_gene_1176 | adhesin-like protein | 1 | 1 | 0.955 | 0.833 | 28 | 0.802 | 28 | 0.866 | 28 |
| Contig40_gene_1198 | protein disulfide-isomerase thioredoxin-related | 1 | 0.999 | 0.975 | 0.527 | 27 | 0.35 | 22 | 0.761 | 22 |
| Contig40_gene_1215 | molybdate ABC transporter substrate-binding protein ModA | 0.995 | 0.999 | 0.978 | 0.57 | 26 | 0.402 | 26 | 0.559 | 26 |
| Contig40_gene_1238 | adhesin-like protein with cysteine protease domain | 1 | 1 | 0.987 | 0.762 | 26 | 0.938 | 26 | 0.944 | 26 |
| Contig40_gene_1247 | hypothetical protein | 0.642 | 0.591 | 0.912 | 0.426 | 28 | 0.477 | 27 | 0.632 | 28 |
| Contig40_gene_1254 | hypothetical protein | 1 | 1 | 0.98 | 0.788 | 27 | 0.77 | 27 | 0.911 | 27 |
| Contig40_gene_1270 | ABC transporter substrate-binding protein | 1 | 0.999 | 0.37 | 0.372 | 24 | 0.24 | 19 | 0.608 | 19 |
| Contig40_gene_1274 | adhesin-like protein | 1 | 1 | 0.982 | 0.649 | 26 | 0.806 | 26 | 0.835 | 26 |
| Contig40_gene_1296 | hypothetical protein | 0.005 | 0.011 | 0.743 | 0.37 | 24 | 0.136 | 12 | 0.243 | 20 |
| Contig40_gene_1331 | hypothetical protein | 0 | 0.001 | 0.746 | 0.336 | 31 | 0.162 | 19 | 0.449 | 31 |
| Contig40_gene_1350 | adhesin-like protein | 1 | 1 | 1 | 0.8 | 25 | 0.775 | 24 | 0.834 | 25 |
| Contig40_gene_1351 | adhesin-like protein | 0.943 | 0.984 | 0.734 | 0.532 | 38 | 0.702 | 38 | 0.854 | 38 |
| Contig40_gene_1355 | adhesin-like protein | 1 | 1 | 0.999 | 0.86 | 26 | 0.795 | 26 | 0.932 | 26 |
| Contig40_gene_1364 | adhesin-like protein | 1 | 1 | 0.998 | 0.696 | 25 | 0.707 | 25 | 0.894 | 26 |
| Contig40_gene_1367 | tungsten formylmethanofuran dehydrogenase subunit G FwdG | 0.221 | 0.576 | 0.221 | 0.4 | 31 | 0.286 | 24 | 0.203 | 24 |
| Contig45_gene_8 | conserved hypothetical protein | 0.998 | 0.936 | 0.003 | 0.272 | 24 | 0.358 | 18 | 0.452 | 18 |
| Contig45_gene_20 | conserved hypothetical secreted protein | 1 | 1 | 0.316 | 0.51 | 21 | 0.43 | 21 | 0.292 | 19 |
| Contig45_gene_21 | conserved hypothetical protein | 0.379 | 0.712 | 0.125 | 0.388 | 36 | 0.592 | 36 | 0.437 | 35 |
| Contig45_gene_30 | hypothetical secreted protein | 0.656 | 0.405 | 0.218 | 0.199 | 26 | 0.176 | 15 | 0.118 | 23 |
| Contig45_gene_35 | conserved hypothetical secreted protein | 0.651 | 0.652 | 0.146 | 0.423 | 30 | 0.447 | 30 | 0.368 | 32 |
| Contig45_gene_36 | peptidase C39 family | 1 | 1 | 0.999 | 0.85 | 26 | 0.947 | 26 | 0.902 | 26 |
| Contig45_gene_60 | poly-gamma-glutamate biosynthesis protein | 0.999 | 1 | 0.061 | 0.216 | 32 | 0.149 | 24 | 0.653 | 26 |
| Contig45_gene_64 | UDP-glucose/GDP-mannose dehydrogenase | 0.942 | 0.802 | 0.938 | 0.534 | 28 | 0.174 | 36 | 0.643 | 28 |
| Contig45_gene_89 | UDP-glucose/GDP-mannose dehydrogenase | 0.961 | 0.635 | 0.59 | 0.562 | 31 | 0.145 | 24 | 0.566 | 31 |
| Contig45_gene_91 | adhesin-like protein | 0.982 | 1 | 0.859 | 0.87 | 28 | 0.529 | 28 | 0.85 | 28 |
| Contig45_gene_93 | adhesin-like protein | 0.999 | 1 | 0.947 | 0.896 | 28 | 0.54 | 28 | 0.851 | 28 |
| Contig45_gene_100 | hypothetical protein | 0 | 0.033 | 0.571 | 0.462 | 24 | 0.28 | 23 | 0.146 | 24 |
| Contig45_gene_106 | adhesin-like protein | 1 | 1 | 0.999 | 0.889 | 28 | 0.871 | 28 | 0.852 | 28 |
| Contig45_gene_116 | conserved hypothetical protein | 1 | 1 | 0.99 | 0.778 | 26 | 0.742 | 26 | 0.872 | 26 |
| Contig45_gene_159 | homoserine dehydrogenase | 0.086 | 0.055 | 0.688 | 0.435 | 39 | 0.152 | 39 | 0.43 | 39 |
| Contig47_gene_7 | adhesin-like protein with cysteine protease domain | 1 | 1 | 0.993 | 0.719 | 25 | 0.896 | 25 | 0.919 | 25 |
| Contig47_gene_13 | hypothetical protein | 0.999 | 0.995 | 0.968 | 0.582 | 35 | 0.285 | 24 | 0.644 | 24 |
| Contig47_gene_57 | adhesin-like protein with cysteine protease domain | 1 | 1 | 0.998 | 0.819 | 26 | 0.807 | 26 | 0.834 | 26 |
| Contig47_gene_60 | hypothetical protein | 0.006 | 0.003 | 0.761 | 0.353 | 29 | 0.225 | 21 | 0.705 | 23 |
| Contig47_gene_62 | adhesin-like surface protein | 0.999 | 0.997 | 0.954 | 0.589 | 34 | 0.655 | 34 | 0.821 | 34 |
| Contig47_gene_98 | adhesin-like protein | 0.999 | 0.986 | 0.355 | 0.086 | 22 | 0.06 | 15 | 0.405 | 20 |
| Contig47_gene_125 | hypothetical protein | 0.999 | 0.986 | 0.757 | 0.467 | 26 | 0.176 | 24 | 0.49 | 30 |
| Contig47_gene_140 | hypothetical protein | 1 | 1 | 0.991 | 0.718 | 23 | 0.731 | 23 | 0.903 | 23 |
| Contig47_gene_146 | hypothetical protein | 1 | 1 | 0.992 | 0.702 | 26 | 0.887 | 26 | 0.713 | 26 |
| Contig47_gene_160 | hypothetical protein | 0.485 | 0.821 | 0.414 | 0.817 | 33 | 0.393 | 33 | 0.472 | 24 |
| Contig47_gene_197 | hypothetical protein | 0.942 | 0.91 | 0.736 | 0.29 | 30 | 0.256 | 20 | 0.6 | 19 |
| Contig47_gene_208 | hypothetical protein | 0.001 | 0.001 | 0.738 | 0.451 | 31 | 0.307 | 23 | 0.66 | 23 |
| Contig47_gene_253 | cobalt ABC transporter permease protein | 0.995 | 0.859 | 0.252 | 0.293 | 26 | 0.443 | 22 | 0.618 | 22 |

FIG. 6-4

| Gene | Description | | | | | | | | |
|---|---|---|---|---|---|---|---|---|---|
| Contig47_gene_269 | coenzyme F420-dependent N(5),N(10)-Methenyltetrahydromethanopterin Hmd | 0.033 | 0.701 | | 0.325 | 23 | 0.177 | 0.188 | 19 |
| Contig47_gene_304 | adhesin-like protein | 0.508 | 0.67 | 1 | 0.389 | 17 | 0.666 | 0.896 | 17 |
| Contig47_gene_306 | hydrolase alpha/beta fold family | 1 | 0.915 | 0.075 | 0.245 | 29 | 0.215 | 0.411 | 17 |
| Contig47_gene_309 | hypothetical protein | 0.966 | 0.847 | 0.108 | 0.434 | 24 | 0.262 | 0.722 | 31 |
| Contig47_gene_349 | adhesin-like protein | 0.008 | 0.319 | 0.989 | 0.116 | 28 | 0.233 | 0.608 | 19 |
| Contig47_gene_353 | OB fold nucleic acid binding domain-containing protein | 0.647 | 0.435 | 0.053 | 0.39 | 23 | 0.171 | 0.281 | 21 |
| Contig47_gene_356 | short-chain dehydrogenase/reductase family protein | 0.936 | 0.889 | 0.047 | 0.357 | 26 | 0.286 | 0.171 | 16 |
| Contig47_gene_375 | hypothetical protein | 1 | 1 | 0.517 | 0.614 | 33 | 0.438 | 0.783 | 33 |
| Contig47_gene_381 | adhesin-like protein | 1 | 1 | 0.988 | 0.764 | 26 | 0.791 | 0.783 | 23 |
| Contig47_gene_391 | hypothetical protein | 0.688 | 0.671 | 0.915 | 0.537 | 28 | 0.28 | 0.647 | 21 |
| Contig49_gene_3 | hypothetical protein | 0.186 | 0.698 | 0.17 | 0.523 | 28 | 0.398 | 0.549 | 28 |
| Contig49_gene_4 | conserved hypothetical protein | 0.125 | 0.542 | 0.798 | 0.552 | 28 | 0.463 | 0.512 | 28 |
| Contig49_gene_25 | transglutaminase-like superfamily protein | 1 | 1 | 1 | 0.719 | 24 | 0.789 | 0.886 | 24 |
| Contig49_gene_43 | adhesin-like protein | 1 | 1 | 0.997 | 0.694 | 24 | 0.929 | 0.907 | 24 |
| Contig49_gene_44 | adhesin-like protein | 0.907 | 0.997 | 1 | 0.534 | 24 | 0.671 | 0.84 | 19 |
| Contig49_gene_96 | hypothetical protein | 0 | 0.106 | 0.86 | 0.431 | 32 | 0.537 | 0.208 | 25 |
| Contig49_gene_128 | ABC transporter substrate-binding protein | 0 | 0.004 | 0.837 | 0.359 | 26 | 0.17 | 0.082 | 21 |
| Contig49_gene_152 | adhesin-like protein | 0.996 | 0.995 | 0.693 | 0.497 | 25 | 0.24 | 0.512 | 21 |
| Contig49_gene_167 | conserved hypothetical protein | 1 | 1 | 0.999 | 0.891 | 32 | 0.913 | 0.891 | 25 |
| Contig49_gene_172 | adhesion-like protein | 0.799 | 0.265 | 0.204 | 0.19 | 21 | 0.039 | 0.179 | 14 |
| Contig49_gene_175 | conserved hypothetical protein | 1 | 1 | 0.999 | 0.596 | 22 | 0.914 | 0.869 | 25 |
| Contig49_gene_180 | hypothetical protein | 0.241 | 0.953 | 0.328 | 0.504 | 24 | 0.306 | 0.63 | 24 |
| Contig49_gene_183 | adhesin-like protein | 1 | 1 | 0.99 | 0.513 | 31 | 0.731 | 0.646 | 24 |
| Contig49_gene_184 | adhesin-like protein | 1 | 1 | 0.999 | 0.885 | 32 | 0.682 | 0.744 | 27 |
| Contig49_gene_194 | hypothetical secreted protein | 0.994 | 0.994 | 0.969 | 0.772 | 26 | 0.918 | 0.668 | 27 |
| Contig49_gene_208 | ABC transporter substrate-binding protein | 0.996 | 0.799 | 0.583 | 0.289 | 33 | 0.343 | 0.674 | 21 |
| Contig49_gene_226 | conserved hypothetical secreted protein | 1 | 1 | 0.041 | 0.32 | 17 | 0.396 | 0.802 | 13 |
| Contig49_gene_239 | adhesin-like protein | 1 | 1 | 0.995 | 0.619 | 27 | 0.866 | 0.743 | 27 |
| Contig49_gene_246 | conserved hypothetical | 0.999 | 1 | 0.484 | 0.31 | 19 | 0.845 | 0.614 | 17 |
| Contig55_gene_2 | hypothetical protein | 0.376 | 0.809 | 0.152 | 0.234 | 33 | 0.11 | 0.242 | 27 |
| Contig55_gene_3 | hypothetical protein | 0.84 | 0.911 | 0.997 | 0.696 | 22 | 0.82 | 0.636 | 25 |
| Contig55_gene_7 | adhesin-like protein | 0.22 | 0.951 | 0.996 | 0.438 | 39 | 0.226 | 0.318 | 19 |
| Contig55_gene_13 | hypothetical secreted protein | 0.951 | 0.956 | 0.291 | 0.627 | 17 | 0.741 | 0.864 | 29 |
| Contig55_gene_23 | conserved hypothetical secreted protein | 0.997 | 0.998 | 0.884 | 0.683 | 32 | 0.796 | 0.873 | 17 |
| Contig55_gene_40 | hypothetical secreted protein | 0.999 | 1 | 0.999 | 0.584 | 21 | 0.866 | 0.857 | 32 |
| Contig55_gene_45 | conserved hypothetical protein | 1 | 0.998 | 0.871 | 0.684 | 28 | 0.272 | 0.682 | 21 |

FIG. 7-1

| Gene Number | Amino acid sequence | SEQ ID NO: |
|---|---|---|
| Contig40_gene_34 | MVLALSILLSSIAAASA | 1 |
| Contig40_gene_35 | MSTFILVIIILGIILIA | 2 |
| Contig40_gene_39 | MDNKKIFVIVALALLAIVAVGSVSA | 3 |
| Contig40_gene_40 | MNNKKIFAIAALAIIAIVAVGSVSA | 4 |
| Contig40_gene_41 | MNAKKLTILAALAILAIVAVGSVSA | 5 |
| Contig40_gene_51 | MICCVLLTFSTVSAIDMDGNLT | 6 |
| Contig40_gene_54 | MIIAIIFMYNRVRNKR | 7 |
| Contig40_gene_63 | MNKVQLSSILALVLILFLSLAVVSA | 8 |
| Contig40_gene_70 | MRKEIISILVIAIIAISVIPTAFS | 9 |
| Contig40_gene_72 | MNKKRFKLLLTIFIAFALINTCFILNDNLS | 10 |
| Contig40_gene_75 | MMVILLITLLSVPILSLTIDYS | 11 |
| Contig40_gene_105 | MNINLKKITFLCLVLVLIGLISFNSISA | 12 |
| Contig40_gene_119 | MNNQNKYSCIVLAGGMSRRMGQ | 13 |
| Contig40_gene_161 | MEDRKAKFIVYVVCLLAFICSSTVFSMTGGLS | 14 |
| Contig40_gene_163 | MNILINGTGAIGIGLGASMISQG | 15 |
| Contig40_gene_164 | MIIVTICVILLILVLFYGLFPGLTNS | 16 |
| Contig40_gene_165 | MSDVGKTVITTIITLVTTAFG | 17 |
| Contig40_gene_169 | LKSDKRAKFAIFFSIAILALGLSNIAA | 18 |
| Contig40_gene_179 | MINGIMDKQKVITAFGIILFLAAAFSPFVVLPILGV | 19 |
| Contig40_gene_187 | MFNKKMVLAISLLAVIFASMCIVSA | 20 |
| Contig40_gene_203 | MKTNLKKTTIILALLMAILILSIGAISA | 21 |
| Contig40_gene_228 | MNSKGKYLVLFLILILSFSIISASFA | 22 |
| Contig40_gene_231 | MKKNLSLKNILILSLIFLFVLSIGSSFA | 23 |
| Contig40_gene_232 | MKRNIYFILLVTLFLISMSVVSA | 24 |
| Contig40_gene_248 | MKKMEMASYIILIASVLAILYA | 25 |
| Contig40_gene_251 | MPKIAKLWNKLADPKNIPRLFAVI | 26 |
| Contig40_gene_252 | MFNLAIWVYLGLALAIFGSLATVWGPGVKDP | 27 |
| Contig40_gene_260 | LFAIVSLSAVSASDDFSSSLADDSDSD | 28 |
| Contig40_gene_269 | MKRRYKVLFLLAILTIISINAISA | 29 |
| Contig40_gene_296 | MLFSVIATVSATC | 30 |

FIG. 7-2

| | | |
|---|---|---|
| Contig40_gene_297 | MFIKIRRDTLIILL | 31 |
| Contig40_gene_306 | MKAVIPAAGLGTRFLPATKAQPKEMLPVYDKPTIQ | 32 |
| Contig40_gene_317 | MIKTDVLVIGAGPAGSSAARFAAKGG | 33 |
| Contig40_gene_346 | MEDNLLKNRKLILISIFLVSLLAISAVSA | 34 |
| Contig40_gene_349 | MNRNKIIVLLVLLIAVVGFTMGPACA | 35 |
| Contig40_gene_352 | MKKSVFKILIALILLAVSIVSS | 36 |
| Contig40_gene_411 | MKKNIFLIAIILIAVVAVSGC | 37 |
| Contig40_gene_431 | MLIALLGLSAVAAVDADPLTDN | 38 |
| Contig40_gene_448 | MSENNRTLITIGIGAFII | 39 |
| Contig40_gene_466 | MGKIFKIVTILLIVIALAILGVFIYSDGHSE | 40 |
| Contig40_gene_483 | MDKKTIIIAAVAILVI | 41 |
| Contig40_gene_501 | MKLNKFFIISILIIFLSISAISA | 42 |
| Contig40_gene_553 | MKKKIAIILGIALLAFLVIGASSA | 43 |
| Contig40_gene_636 | MNFNKKILLIIALVFIASVGIVAA | 44 |
| Contig40_gene_721 | MKRSIIFLTIILSLFLVIGYASA | 45 |
| Contig40_gene_730 | VGITFTAIITGALGGTTFSEPLGNYLSQFIPY | 46 |
| Contig40_gene_732 | MDSKKLILVTALAFLAIVSIASVSA | 47 |
| Contig40_gene_733 | MNVNKKIFLLVIFIISISIAGVYCADIHQDSDLTA | 48 |
| Contig40_gene_749 | MILALFCFIVIGSASAADFK | 49 |
| Contig40_gene_750 | MISLLLISILAISAASAA | 50 |
| Contig40_gene_762 | MEEKIALAACSGMSPNGLVARVAVHDLAID | 51 |
| Contig40_gene_766 | MLKTKLCGISLKNPLMLAAGVLGSHA | 52 |
| Contig40_gene_769 | MEIVLCVTGSVAAVETVKLAREFKRQG | 53 |
| Contig40_gene_787 | MVVATIIFASSLFDALYGFKN | 54 |
| Contig40_gene_815 | MILAILLAVGMTLTAVSA | 55 |
| Contig40_gene_824 | MNKRIFLYIALIFIISLLSFSAVSA | 56 |
| Contig40_gene_828 | MKYNKKIFFLFLLLCLIIPQAIY | 57 |
| Contig40_gene_834 | MNSNKTYAVLGLLLLLILSIGAISA | 58 |
| Contig40_gene_835 | MINKRIISLSLLIILVFLIIGLSAVSA | 59 |
| Contig40_gene_836 | MDFKKAIPLFALLLILFIIGSSSA | 60 |
| Contig40_gene_837 | MKLKKFSVILAVLLVAILAIGAVSA | 61 |
| Contig40_gene_841 | MILISLILVILSISCVSA | 62 |

FIG. 7-3

| | | |
|---|---|---|
| Contig40_gene_847 | MDNSNIIISVIIVLCIAAGVTA | 63 |
| Contig40_gene_848 | MDNSSILISVIIVLCIAAGVTA | 64 |
| Contig40_gene_867 | MRKEILIAAIAIAILILCGGVFA | 65 |
| Contig40_gene_872 | MLISIVLISLIALGAVSA | 66 |
| Contig40_gene_900 | MKEIAIYLILIIIVLIAAQHL | 67 |
| Contig40_gene_906 | LFEAGMIALPTGLPGLALLGL | 68 |
| Contig40_gene_909 | MKNWKIIGLILILLAVVSVSG | 69 |
| Contig40_gene_930 | MKPLIIKISIFCNKKIFIFTLMIVMLLSLAAVSA | 70 |
| Contig40_gene_964 | MSIKRILLTSLMLFIIIFSISFVSA | 71 |
| Contig40_gene_975 | MDKVGIIGAGSLGTALAQTVANNV | 72 |
| Contig40_gene_982 | LICSIQACSASCTAVYVGP | 73 |
| Contig40_gene_996 | MKISRIILILLLFVVFFEIGLFSSYTIVNA | 74 |
| Contig40_gene_1008 | MILISLFLISLLAIGAASA | 75 |
| Contig40_gene_1021 | MKLYKNSIIILLILILSIGAAAA | 76 |
| Contig40_gene_1025 | LAVILILFSLGTVAASENIVI | 77 |
| Contig40_gene_1029 | MRNPKDYIMKTDYLIIlMALLLISIVSPIAA | 78 |
| Contig40_gene_1036 | MNNKKIFVAGLAILAIVLMGSVA | 79 |
| Contig40_gene_1074 | MEKTMKSKLFILLIIISILISISSVSA | 80 |
| Contig40_gene_1084 | MDKKIFIVSFILLAIFTIGAVGA | 81 |
| Contig40_gene_1088 | MMKMTKKNLFLISLILILILTIGAVSA | 82 |
| Contig40_gene_1089 | MVIMNNKKLFIVSLILTILTIGAVSA | 83 |
| Contig40_gene_1093 | MKFNKNRGISAISILILEFLSISMASA | 84 |
| Contig40_gene_1097 | VFILKFEIKRSLIFISILAILILSIGMASA | 85 |
| Contig40_gene_1098 | MQAIIPVKDNFLILVTNMKKSDFKRIFICLVLLTCLIGAVSA | 86 |
| Contig40_gene_1099 | MNFKKLLMISLILLFVLSVGFSTASA | 87 |
| Contig40_gene_1104 | MKIKKSFVILCLIICLFTIASVAA | 88 |
| Contig40_gene_1106 | VTVSVFISASFAFGNVLSNADNG | 89 |
| Contig40_gene_1158 | MKVLKIAIIMLILIISLGAVSA | 90 |
| Contig40_gene_1176 | MNFKTKGSLILISLLFILIIGIGMASA | 91 |
| Contig40_gene_1198 | MGKFKFIFILVLALFLICGIA | 92 |
| Contig40_gene_1215 | MDSKKILMIAVVALIAIVAVSSCSA | 93 |
| Contig40_gene_1238 | MKLKSKYFVFLLIICILFSISTVSA | 94 |

FIG. 7-4

| Contig40_gene_1247 | MNYSIIIFIFIFLMDALVLMASIQVCGA | 95 |
|---|---|---|
| Contig40_gene_1254 | MKFNSRVLGILSLLFVLTILVSSVGA | 96 |
| Contig40_gene_1270 | MEKKTIILVILIALIAC | 97 |
| Contig40_gene_1274 | MKNKSLILISLLLLITIISIGSVVA | 98 |
| Contig40_gene_1296 | MRSTILLSASTAESRSPSLTTGR | 99 |
| Contig40_gene_1331 | VLLICFIGLVEAILMALVDWEDLAISVRKSP | 100 |
| Contig40_gene_1350 | MNKKIILSLLLVLLVAISVSAVAA | 101 |
| Contig40_gene_1351 | MSLSIFVLVIGGGFINKRILLIFVFLIFFISIGSVVA | 102 |
| Contig40_gene_1355 | MNNKKIIMSFLLVLLIAISVSAVSA | 103 |
| Contig40_gene_1364 | MKIQRGIYILTLLVLFSLSAASAA | 104 |
| Contig40_gene_1367 | MELKVDQDKCLGCGVCVIACPVNASISPEN | 105 |
| Contig45_gene_8 | MNRRSKLIIAILIVIII | 106 |
| Contig45_gene_20 | MKRSKKLIIAILVVILLGLL | 107 |
| Contig45_gene_21 | MKEYKIAIIGGGPAGMIAAIRAAEILGPNAVCILE | 108 |
| Contig45_gene_30 | MANEGGGHLKTILMIILIAFICGL | 109 |
| Contig45_gene_35 | MDNKIKAGIALAIIVLVAVIGFSFINESN | 110 |
| Contig45_gene_36 | MFKVSKSILIVCLVSLFLLVSQASA | 111 |
| Contig45_gene_60 | MWYDMKRRRFYLILFTILLILAAIA | 112 |
| Contig45_gene_64 | MKITVAGVGYVGLSLAVLLAQKHDVTA | 113 |
| Contig45_gene_89 | MNLMKITVAGVGYVGLSIAILLAQKHDVTA | 114 |
| Contig45_gene_91 | MEIRYKNLLKVFTIFLVLLISCGFASA | 115 |
| Contig45_gene_93 | MKIRYKNLLKVFTIFLVLLISCGFASA | 116 |
| Contig45_gene_100 | MQRSLFDKVKTSLWMLPSFFGLV | 120 |
| Contig45_gene_106 | MKFKNSHILLVSLISIFLLLSISAAASA | 121 |
| Contig45_gene_116 | MNSKKIAIVLGIILLSFAIVGSASA | 122 |
| Contig45_gene_159 | MDECKLVLIGFGAVGQGVARAISMKKEMINEKFGISLKV | 123 |
| Contig47_gene_7 | MMRKTIFGVIFIVFILFSISTVSA | 124 |
| Contig47_gene_13 | MNKQNVFALILLTILLLSVVAVS | 125 |
| Contig47_gene_57 | MLNKKIIILTFILILSISSASASA | 126 |
| Contig47_gene_60 | MGVLASVAGGIFFEAGMIATCT | 127 |
| Contig47_gene_62 | VFSVSLNKLKIGRVFICLFILVFISCSINCVFA | 128 |
| Contig47_gene_98 | MGGEIINNEKLKLILIT | 129 |

FIG. 7-5

| | | |
|---|---|---|
| Contig47_gene_125 | MDKKMIVSVAFLLLILAVALVSVFDESNS | 130 |
| Contig47_gene_140 | MKISRIIVLLMILIFTAGMVYA | 131 |
| Contig47_gene_146 | MDSKKILVILGLTVLAIFLASSVSA | 132 |
| Contig47_gene_160 | MKPYVILIGSASGIGKSTVAAELAKTLNIKHLV | 133 |
| Contig47_gene_197 | MLISVLGVIVIIMVVAA | 134 |
| Contig47_gene_208 | MATRTKQTICRLYSFHGGRFL | 135 |
| Contig47_gene_253 | MELSKSDKYLIVGIIFCLAL | 136 |
| Contig47_gene_269 | MKVAILGAGCYRTHAASGITNF | 137 |
| Contig47_gene_304 | LSVILILFLAVSTVAA | 138 |
| Contig47_gene_306 | MNKKLKIILYILLALI | 139 |
| contig47_gene_309 | METKNLIIICATVILAVVIVLSAFIYVNMGN | 140 |
| Contig47_gene_349 | VLVLAFAIIFLGYSISLGNNQ | 141 |
| Contig47_gene_353 | MELNDEIIFKVALITALVGMIG | 142 |
| Contig47_gene_356 | MKNYFDIKDKVAVVTGASSGLGWQI | 143 |
| Contig47_gene_375 | LTFNNLRINIKDCMVIFVVFTVLLLSILAVSA | 144 |
| Contig47_gene_381 | MKFKKYLFLILIALICIISVSAVA | 145 |
| Contig47_gene_391 | MDKKMTVLLVALFCLLCVGS | 146 |
| Contig49_gene_3 | MDRKDIIIILVLIIISLLALGLHNHQV | 147 |
| Contig49_gene_4 | MTSEIMILTPTAVVLAADSAVTISDIK | 148 |
| Contig49_gene_25 | MRKKILFLTLMILICFTLNSVCA | 149 |
| Contig49_gene_43 | MRLRYFAIISLILLIFLVPVSFA | 150 |
| Contig49_gene_44 | MFIGLLLIIPISFA | 151 |
| Contig49_gene_96 | LLIGLVICAGVFYFQFNYATPTYL | 152 |
| Contig49_gene_128 | VVLVAVVVIGSTAFLLNYDETVKYT | 153 |
| Contig49_gene_152 | MDKKTLAIIAIIVIALVAVG | 154 |
| Contig49_gene_167 | MNNKTLFIIGLFICLLFTIPMVSA | 155 |
| Contig49_gene_172 | MIKTDNKGQITVELLLLSF | 156 |
| Contig49_gene_175 | MLNRKALIFSLIVLFMLSISAVSA | 157 |
| Contig49_gene_180 | MDNKAIIGIVIALIVIVLACFAY | 158 |
| Contig49_gene_183 | MSYFNKGHIWNLLLICLLIGTLAMMGSASA | 159 |
| Contig49_gene_184 | MKNKAMFLISALLIAVILSLSAVSAADDAIA | 160 |
| Contig49_gene_194 | MKFNKSLIAIFVILVAFSSISVIA | 161 |

FIG. 7-6

| Contig49_gene_208 | MDKKIIGAVVALLVIIVGA | 162 |
|---|---|---|
| Contig49_gene_226 | VEGDNMVNIKTVALAV | 163 |
| Contig49_gene_239 | MLIMAILVLLTMASVSASELEDIQVT | 164 |
| Contig49_gene_246 | MNNTTKILIGVLMGLL | 165 |
| Contig55_gene_2 | METENLIIVILLVLLIAMAGIF | 16 |
| Contig55_gene_4 | MFLVILLFAFIVIGGSYSVFA | 167 |
| Contig55_gene_7 | MALLILAMSCVSASNASDNLDDLTISDSNSLDLVSTSN | 168 |
| Contig55_gene_13 | MNNKYFLGIIIIIAV | 169 |
| Contig55_gene_23 | MLLNDKSELLKSLSILFLLIVLITSFNSVYA | 170 |
| Contig55_gene_40 | MKKIILGTCILFLLISVAYA | 171 |
| Contig55_gene_45 | MKINLKRVILGIILILICISSASIISA | 172 |

FIG. 8-1

| Gene Number | Nucleotide sequence | SEQ ID NO: |
|---|---|---|
| Contig40_gene_34 | atggtccttgccttaagcataatcctactcagttcaattgcagcagcatctgca | 173 |
| Contig40_gene_35 | atgagtactttttattttagtcataataactgttatttatttaataatcgca | 174 |
| Contig40_gene_39 | atggataataaaaaaatatttgttattgtagctttgctctttagctatcgttgcagtaggatctgttag | 175 |
| Contig40_gene_40 | atgaacaataaaaaaatatttgcagcttagcagttatagcatcgtagcagtagatcagtcagtg ct | 176 |
| Contig40_gene_41 | atgaatgctaaaaaactaactattctagcagccttagctatctcgctatcgttgcagtaggctcagtaagtg ct | 177 |
| Contig40_gene_51 | atgatttgctgtgtttattaacatttcaactgttagtgcaattgatatgatgaaatctaact | 178 |
| Contig40_gene_54 | atgattattgccataatctcttcatgtataatagggtccgcaataagaga | 179 |
| Contig40_gene_63 | atgaataaggttcaattgtcctccatactgcttagtattaatattattcttgtcttgctagtagtg ca | 180 |
| Contig40_gene_70 | atgagaaaagaaataatttctatattggtaattgctattatagcaatctcagttattccaactgccttca | 181 |
| Contig40_gene_72 | atgaataaaaaaagatttaaatttaactattttatagcatttgcactcattaacacttgttttattt taaatgataatctctca | 182 |
| Contig40_gene_75 | atgatggtcattctactaataacactcctttctgttcctatcctcactacaattgattattca | 183 |
| Contig40_gene_105 | atgaatattaattaaaaaaatcacattcttatgtttggttttagttctaatcggttgatctcattaatt caatcagcgct | 184 |
| Contig40_gene_119 | atgaataatcaaaataagtattcttgcatagtttgcatagttttatgtgcttgctttatctgcagcagcacag | 185 |
| Contig40_gene_161 | atggaagatagaaaagcaaaacaaaattatcgttatgctgttactgttgctgctttatctgcagcagcacag tcttctctatgactgcgcggtctttct | 186 |
| Contig40_gene_163 | atgaacatactaatcaatggaactgagctatcggaataggctggagcatctatgattcacaaggt | 187 |
| Contig40_gene_164 | atgataatagtcactacaatctgtgttatcttaatttgatagttctttttgattgttccctgattga caaacagc | 188 |
| Contig40_gene_165 | atgtctgatgttggtaaaactgtaataacactattattacttagtaactactgcattggt | 189 |
| Contig40_gene_169 | ttgaaatcagataaacgggctaaattgccatatattctctcaattgcaatccttgccttgggactgagcaata ttgcagct | 190 |
| Contig40_gene_179 | atgattaatgaataatgaacaagcagaagttatacactgccttttggcataattctattttttggcagctgctt tcagtccgttttgtagtcttgcctatcttaggagtt | 191 |
| Contig40_gene_187 | atgtttaataagagatggttttagccataagcttattagcttatctttgttatcttatgtgcatagtttcag ca | 192 |
| Contig40_gene_203 | atgaaacaaatcttaaaaaacaacaatcatattggcactgctgatggccattttaatttatcgattggag ccatctctgca | 193 |

FIG. 8-2

| | | |
|---|---|---|
| Contig40_gene_228 | atgaattccaaggaaatatctgttttattctatttaatattatcattagcataatctctgcttcat ttgct | 194 |
| Contig40_gene_231 | atgaagaaaattaagcttaaaaatatttaattttatcattaatcttccttttgtattaagcataggat cttcatttgca | 195 |
| Contig40_gene_232 | atgaaaaggaatatttattatttattagttacactatttttaatcagtatgagtgttgttagtgca | 196 |
| Contig40_gene_248 | atgaaaaaaatggaaatggctagtatattatctttaattgcatctgtattagctatacttttatgca | 197 |
| Contig40_gene_251 | atgcctaaaattgcaaaattatgaataagctagcagatccaaagaacattcctaggctgtttgctgtaatt | 198 |
| Contig40_gene_252 | atgtttaatctgctattgctatttgggtttatttaggtttggcattagtctatttttgaagcctcgcaactgtatggg gtcctgagtaaaggatcca | 199 |
| Contig40_gene_260 | ttgttcgctatagtaagcctatctgcagtcagcgcaagcgatgattttcagttcccttgc | 200 |
| Contig40_gene_269 | atgaaaagaagatataaagtttatttctattggccatcttaactatcttaataagcattaatgccattcagct | 201 |
| Contig40_gene_296 | atgctcttttcagtaattgctactgtatctgctacttgt | 202 |
| Contig40_gene_297 | atgtttattaaaattagaagagacacttaataatattat | 203 |
| Contig40_gene_306 | atgaaagcagtcattcctgcgcagcaggcttgaacaagattcctcctgctactaaagctcaaccaaaagaga tgttgccggttttatgacaagccgaccattcaa | 204 |
| Contig40_gene_317 | atgattaaaactgatgtattggttattggtgctgaccctgcttgttcttcagctgctagatttgcagctaaag gcggc | 205 |
| Contig40_gene_346 | atggaggataatctttttgaaaatagaaaactaatttgatataattctccttgttagtctgcttgcaattt ctgctgtaagcgca | 206 |
| Contig40_gene_349 | atgaacacagaaataaattagttttttgcttgtattattgatagcagttgttggctttacaatgggccagctt gtgca | 207 |
| Contig40_gene_352 | atgaaaaatcagttttaaaattctaattgcttttaatttattgctgtatcaattgtttcatct | 208 |
| Contig40_gene_411 | atgaaaaagaatatttttttttaattgcaataataactaattgcagttgttgcagttagtgatgt | 209 |
| Contig40_gene_431 | atgttgattgccttactgtctctgcttgttgacgcttaacatgcattaactgataat | 210 |
| Contig40_gene_448 | atgagcgaaatataatagaaacttgattacaataggaatcggcgcttttattata | 211 |
| Contig40_gene_466 | atgggaaaagatatttaaaattgttacaatcatattgattgtcattgctatacttggtgttttcatct attctgatgacattctgaa | 212 |
| Contig40_gene_483 | atggataagaaaacaatcattatagctgcagtagctattctcgttatt | 213 |
| Contig40_gene_501 | atgaaattaataaattcttcattatcagcatatcatttattattctatcaattagtcaataagtgc | 214 |
| Contig40_gene_553 | atgaagaaaaatagcaattatttttaggaattgcattattagcattcttagtcatcggcgcatccagcgca | 215 |
| Contig40_gene_636 | atgaatttcaataaaaatttttattaataatagcattgtattcattgctagtgttggcattgtttgcagct | 216 |
| Contig40_gene_721 | atgaaaagatcaatcatatttttaacaattaatattatcctatttttagtaattggctatggctatgcaagcgct | 217 |

FIG. 8-3

| | | |
|---|---|---|
| Contig40_gene_730 | gtgggcataaccttacagcaatcatcacaggggcattagtggaactacttttcagaacctttaggaaact acctagccaattcatacctttac | 218 |
| Contig40_gene_732 | atggattctaaaaaactgattttagtgactgcattggcttttttagctattgtttccatagcttcagttagtg catggacttgtttgaa | 219 |
| Contig40_gene_733 | atgaatgtgaataagaaaatatttttacttgtaatcttttatatatctatttcaatagctggatatattgtg cagacatccatcaggatagcgatttaaccgca | 220 |
| Contig40_gene_749 | atgatactggcactattttgttttatagtcattggctcagcaagtgcagcagactttaaa | 221 |
| Contig40_gene_750 | atgatctcactgcttcttatttcaattcttgctataagcgcagcaagtgctgca | 222 |
| Contig40_gene_762 | atggagaaaaaattgcttttagctgcttgcagtggtatgagtcagtccaaatgtttgttgcaagagttgcagttc atgatttggctattgacg | 223 |
| Contig40_gene_766 | atgttaaaaactaaattatgcggaattagtttaaaaatccattaatgcttgctgcaggtgttttgggaagcc atgca | 224 |
| Contig40_gene_769 | atggaaattgtattatgtgtaacaggcagtgtagctgcatgaaactgtaagttagctcgtgaatttaagc gtcaaggc | 225 |
| Contig40_gene_787 | atggtagttgcaacaataatctttgcatccagcttattcgacgcccttatgatttaaaaac | 226 |
| Contig40_gene_815 | atgatattggcaatatattgcttgccgttgaatgacacttactgcagtaagtgca | 227 |
| Contig40_gene_824 | atgaataagcaatatattctatatatagcacactgatttttattatttccctgcttctttttctgcagtcagtg ct | 228 |
| Contig40_gene_828 | atgaaatataataaaaagataatattcttttatttttattgtctcataattcctcaagctatttat | 229 |
| Contig40_gene_834 | atgaattctaataagacttatgcagtattaggattatgctcttataatcttatccatagggctattagtg ca | 230 |
| Contig40_gene_835 | atgataaataaaagaataattagtcttagtctgctgattatattggtcttttctcattattgattaagtgcag tcagtgct | 231 |
| Contig40_gene_836 | atggatttttaaaaaagcaatccctctatttgcttttattgattttattatcggctcttcaagcg ca | 232 |
| Contig40_gene_837 | atgaagcttaaaagtttcagtgtattgcttgtagcaataactgctattgggctgtaagtg ca | 233 |
| Contig40_gene_841 | atgattttaatatccttaatttagttatcttaagcattcttgtgtaagtgct | 234 |
| Contig40_gene_847 | atggacaactccaatattataatctcagtaattatagtattgcagcaggagtaactgca | 235 |
| Contig40_gene_848 | atgataattcaagcattcttatatccgtaatcatcgttttatgttatgcagcaggagtaactgcc | 236 |
| Contig40_gene_867 | atgagaaaggaaattttaattgcaatcatattatattatgtggaggtgtatttgca | 237 |
| Contig40_gene_872 | atgttgatatcaattgtacttatatctctcattgcttttaggtcagtaagtgca | 238 |
| Contig40_gene_900 | atgaaagaaattgctatttctatttcatcctccttatccataatgttcttattgccgcacaacactta | 239 |

FIG. 8-4

| | | |
|---|---|---|
| Contig40_gene_906 | ttgtttgaagcaggtatgattgctcttcctactggtttgcctgacttgcctgttgggctt | 240 |
| Contig40_gene_909 | atgaaaaactggaaataattggattaatatattcatcccttctgctgtcgtttcagttagcggc | 241 |
| Contig40_gene_930 | atgagaaataaaaagatttcatttttacttgattgtcatgctattatcgcttgctgcagttcagcaa atgatctgataatcttgaagttgatgat | 242 |
| Contig40_gene_964 | atgagtattaaacgaatattacttacgagtttaatgctatttataataatatttcaatttcgttttgtaagtg caaatgaaaa | 243 |
| Contig40_gene_975 | atggataaggtaggaattatagagcaggtagtctaggtacagctttagctcaaacagtggcta | 244 |
| Contig40_gene_982 | ttgatctgtagcatacagccctgctcggctcatgcactgcagtctatgtagggct | 245 |
| Contig40_gene_996 | atgaaaatatcaagaattatactattatattgcttttgttgtattttttgaaataggactgttcagctcat ataccatagtaaatgct | 246 |
| Contig40_gene_1008 | atgattttaattatttcactattccttattcatcgctatcggtgcgcaagcgca | 247 |
| Contig40_gene_1021 | atgaaattatataaaatagcataatcattttattttaatttttatcgattggagcagctgcagct | 248 |
| Contig40_gene_1025 | ttggcagtgattttgataatcctatttcacttgaactgttgcagcaagtgaaaatatagttatt | 249 |
| Contig40_gene_1029 | atgagaaacctaaagattatatatgaagactgattatttgattattcttatgcctttattgctgatttcta tagtttcacctatagcagct | 250 |
| Contig40_gene_1036 | atgaataataaaagatatttgtgccgattagcatatttggctattgttctaatggatcagttgct | 251 |
| Contig40_gene_1074 | atggagaaaactatgaaatctaaactttttatactttctaatcattatctaataagcattcatcag tttcagca | 252 |
| Contig40_gene_1084 | atggataaaagatttttatagtttagctttttttttaattagtttaatactactaatttcttctagctattttcacaataggggctgttggcgct | 253 |
| Contig40_gene_1088 | atgatgaaaatgactaaaaagaatctttttttaattagtttaatactactaatttttacaattggtgctg tcagcgca | 254 |
| Contig40_gene_1089 | atggtgattatgaataataaaagcttttttattgttagtttgattatactaactatttgacaataggcgctg tcagtgca | 255 |
| Contig40_gene_1093 | atgaagtttaataaaataggggcatatctgccatatcaataatttaattctattttaagtatttctatgg catctgct | 256 |
| Contig40_gene_1097 | gtgtttatttgaatttgaattaaaagaagttaatatattcatttcaatattattgatcttatcta ttggaatggcatctgaa | 257 |
| Contig40_gene_1098 | atgcaagcaattattccagttaagacaatttctaattttagtgacaaatatgaagaaaagtgattttaaac gtatattcatatgttagttcttcttactgcttgattggtgcagtaagtgct | 258 |
| Contig40_gene_1099 | atgaactttaaaaaaaacttttaatgatttcattattttgtcttatcagtaggatttagcacagcaa gcgct | 259 |
| Contig40_gene_1104 | atgaaaattaaaagagttttgtcattttatgcttaattactattgcaagtgttgcagct | 260 |
| Contig40_gene_1106 | gtgactgttttatttcagttgtttttataagtgcttcatttgcttttttggcaatgttcaagcaatgcagataacgga | 261 |

FIG. 8-5

| | | |
|---|---|---|
| Contig40_gene_1158 | atgaaggtcttaaagatagcaattatcatgctatttaatcatatctctggagcggtttcagca | 262 |
| Contig40_gene_1176 | atgaatttaaaacaaaagaagcttgattcttattcattacttttcattttaataataagtattggaatgg catcagca | 263 |
| Contig40_gene_1198 | atgggaaaatttaaattatattttattctagttttagctctatttttaatatgtgaattgct | 264 |
| Contig40_gene_1215 | atggattctaagaaaatattaatgattgctagttgctgttaatagcaattgttgctaagttcatgctctg ca | 265 |
| Contig40_gene_1238 | atgaagttaaaatcaaagtattttgtattttactcataatatgtatcctattcagtatttcaacagtttcag cg | 266 |
| Contig40_gene_1247 | atgaattattccattattatctttcattatctttcttatgatgcattggtgttaatgctagcatacaagtct gtggagct | 267 |
| Contig40_gene_1254 | atgaagtttaattcaagagtttagggatttatctctattatttgttcttacaattcttgtttcaagtgtgg gggca | 268 |
| Contig40_gene_1270 | atgaaaagaaaactacaattatatgttattttaattgctctcttattgcatgc | 269 |
| Contig40_gene_1274 | atgaagaataagagtttaatattcttattcttattactgattacaataagcataagaggatctgttgttg ca | 270 |
| Contig40_gene_1296 | atgagaagcactatcctgttaagtgcaagtactgcggaaagcgttcaccaagtctcacacaggcaga | 271 |
| Contig40_gene_1331 | gtgcttctcattgcttttataggattggttgaggcgatactgatggcattgttgattgggaggacttggcaa tatccgttcgcaagtctcct | 272 |
| Contig40_gene_1350 | atgaataaaaattatctttagtattattagtagctatttctgtctctcgagttgcagca | 273 |
| Contig40_gene_1351 | atgtcgttatccatattgttctgttctgttataggaggtggattattaataaaagaatatattattcgtat ttctaatattcttcataagtattggatctgtagttgc | 274 |
| Contig40_gene_1355 | atgaacaataataaaagattatataatgtcttttctcattggtcctattgattgcaatatctgtctctgcagtttcag ca | 275 |
| Contig40_gene_1364 | atgaaaatccaaagaggtatatatataataattacttacttgttctctttagccttttctgctgcaagcag ca | 276 |
| Contig40_gene_1367 | atggaacttaagtagatcaagataagtgttaggttgtggagtatgtgttatcgcatgtcctgtaaacgctt ccatcagtccgaaaac | 277 |
| Contig45_gene_8 | atgaatcgaagatcaaagttaataattgcgattttaatagttatcataata | 278 |
| Contig45_gene_20 | atgaaaagatcaaaaaattaattatagacaattcttgttgtaatccttttggattacta | 279 |
| Contig45_gene_21 | atgaagaatacaagataagcaattatagagaagggccagaggaatgataagctgcaataagagccgcagaaa tattaggcccaaatgcagtatgcattctagag | 280 |
| Contig45_gene_30 | atgcaaatgaaggtggaggacatttaaagactatttgatgattataatcttaatagctttatttgtggtc tt | 281 |
| Contig45_gene_35 | atggataataaatcaaagcaggcattgcacttgcaataatcgttttagtggctgtcattggctgtttcattca | 282 |

FIG. 8-6

| | | |
|---|---|---|
| Contig45_gene_36 | ttaatgaaagcaat | 283 |
| Contig45_gene_60 | atgtttaaagtaagcaaaagcatattaatcgtttgttagtatcccttttcctattagttcacaagctagcg ct | 284 |
| Contig45_gene_64 | atgtggtatgatatgaaaagaagaaggttttattttaatattatctattgattttagcagctatag ca | 285 |
| Contig45_gene_89 | atgaaaattacacagttgcgggtgtaggatatgtaggctttcactgctgtctgcgtcaaaaacatgatg ttacagct | 286 |
| Contig45_gene_91 | atgaatttgatgaaaattacagttgcgggagtggatgtaggctttctattgctattctgcttgcccaga aacatgatgtaaccgca | 287 |
| Contig45_gene_93 | atggagataagatataaaatttattaaaagttttactatttttctgtttactcatcagttgcggattg cctcagca | 288 |
| Contig45_gene_100 | atgaagataagatataaaatttattaaaagttttactatttttctgtttactcatcagttgcggatttg cctcagca | 289 |
| Contig45_gene_106 | atgcaacgttcattatttgataaagttaaaacatcctatggatgcttccatctcctttttggattggta | 290 |
| Contig45_gene_116 | atgaaattaagaattcacatatcttactcgtttcattaatatccattttctattgttgagcataagcgag ctttctgca | 291 |
| Contig45_gene_159 | atgaattctaaaaagatagcaattgttcttggaataatattgctttcatttgcaattgtaggctctgcatcag ct | 292 |
| Contig45_gene_7 | atggatgaatgtaaacttgtattaatcgttttggcgctgtaggccaaggtgttgcacgtgcaatatccatga aaaggaaatgatcaatgagaagtttgcataagcctaaaagta | 293 |
| Contig47_gene_13 | atgatgaggaaacaaatatttggagtgttaatcgttttattttatcgttttttattcagcattcaacggtttcagca | 294 |
| Contig47_gene_57 | atgaataacaaaacgtatttgcttgtgatattattaacaatcattcttttattatctgtagttgctgtcagc | 295 |
| Contig47_gene_60 | atgttgaataaaaaaataataaatttattaacatttattttttaatattgtctattttcttcagcaagtgcatctg ca | 296 |
| Contig47_gene_62 | atgggagtattagctagtgttgctgagggcatatttttgaagcaggcatgatgctacttgtaca | 297 |
| Contig47_gene_98 | gtgtttcagtgagttaaataacttaagattggtagagtttttattgtctttttattttagttttattt cttgttcaattaattgtgttttgca | 298 |
| Contig47_gene_125 | atgggaggtgaaataataataatgaaaattaagttaattttcttttattgattttggcagtttagtctctgtatttg atgaaagcaatagc | 299 |
| Contig47_gene_140 | atggataagaaaatgattgttcagtgctttcttttattgattctaatcttcactgcaggaatggttatgca | 300 |
| Contig47_gene_146 | atgaaaatctcaagaataattgtattattaatgattctaatcttgttttaactgtttttagctatttttttagcttgtacta | 301 |
| Contig47_gene_160 | atgaaccatatgtaattctcataggaagcgcttcaggataggaaaatccacagttgcagctgaacttgcaa ct | 302 |

FIG. 8-7

| | | |
|---|---|---|
| Contig47_gene_197 | aaacattaaacattaagcacttggtg | 303 |
| Contig47_gene_208 | atgttaatatcagtcttggagtgattgtaattatcattatggtagttgcagct | 304 |
| Contig47_gene_253 | atgcaaccagaacaaacaaacaactatatgcagttgtattccttccatggggtcgtttctta | 305 |
| Contig47_gene_269 | atggaattaagtaaaagtgacaaatattaatcgtagtaggattatattctgtcttgcatta | 306 |
| Contig47_gene_304 | atgaaagtagcaattttaggtgctggctgttacagaactcacgcagctagtgaattacaaatttt | 307 |
| Contig47_gene_306 | ttgtcagttattctgattctgttttagcagttcaacggtagctgca | 308 |
| Contig47_gene_309 | atgaataagaaactaaaataatccttatatttattggcttaata | 309 |
| contig47_gene_309 | atgaaactaaaaatcttataatcttgtcaactgtaatattggctgttgtaatagttttatctgcttta tttatgtcaacatggcaat | 310 |
| Contig47_gene_349 | gtgcttgttttgcaataatatttctaggatattccatctccttaggaacaatcaa | 311 |
| Contig47_gene_353 | atggaattgaatgatgaaataataatttaaagttgcactgattactgcattggtcggaatgattggg | 312 |
| Contig47_gene_356 | atgaaaaatttatttcgacataaaagacaaagtagcagttgtaaccggtgctcttccggattaggttggcaaa tt | 313 |
| Contig47_gene_375 | ttgactttcaacaaccttagaataaacattaaagattgcatgtaatatttgtagtgtttacagtattgcttt tatctatttagctgtaagtgc | 314 |
| Contig47_gene_381 | atgaaattcaaaaaaatatttattcttgctaatagctcttattgcataatcagtgtctctgcagttgctg | 315 |
| Contig47_gene_391 | atggataaaaaaaatgacagtttttattggttgcccctattttgcctctctctgtgtaaggctca | 316 |
| Contig49_gene_3 | atggatagaaaggacatcataatactcgttctcataatcgttctcatatcactattggcattgggccttcata atcatcaagt | 317 |
| Contig49_gene_4 | atgacatctgagattatgattttaacaccaactgcagtggttttagcggcggacagtgcagttacaataagcg atataaaa | 318 |
| Contig49_gene_25 | atgaggaaaagatccttttcctaactttgatgatactaatctgttttacttaaacagcgtttgtgct | 319 |
| Contig49_gene_43 | atgagattaagataagacatatttgcaataaattagtttaattcttttattgtctttttatttaccatgttagttttgca | 320 |
| Contig49_gene_44 | atgttttattgcttattattaataagtctattaatcatccctataagttttgct | 321 |
| Contig49_gene_96 | ttgctaattgacttgctgttgtgactgtcatctgcaggtgtcttttacaattaactatgcaactcccacatatct | 322 |
| Contig49_gene_128 | gtggttttagttgtctgttgtgtagtgtgattgctctactgtcattccttattaaattatgatgaaactgtaaaataca ct | 323 |
| Contig49_gene_152 | atgataaaaaactctagcaattattgctattattgttatatcgttatagctcttgtagctgttggt | 324 |
| Contig49_gene_167 | atgaataataagacattattttatcattggttattcatatgtcttttattttaccatacctatggtatcagct | 325 |
| Contig49_gene_172 | atgataaaacagacaataaaaggacagataacagtcgaactgctcctttcttttaagcttt | 326 |
| Contig49_gene_175 | atgttaaatagaaaggctttgatttttttcattgatttgtttatttatgctatccattctgctgtttcagct | 327 |
| Contig49_gene_180 | atggataataagcgataattgtaattggaattgcattgattgtaattgtccttgcatgcttttgcttat | |

FIG. 8-8

| | | |
|---|---|---|
| Contig49_gene_183 | atgagttatttaataaggacatatatgaatattttattaattgtctttctcatcggaactttggctatga tgggttcagcaagtgcc | 328 |
| Contig49_gene_184 | atgaaaaacaaggcaatgtttttaatatctgcattattgatagcagttattctatctctcagtgctgtaagtg ctgcagatgatgctattgct | 329 |
| Contig49_gene_194 | atgaaatttaacaagagttaattgcaattttgtaattttgattgttgctttcagttccatatctgtcattg ca | 330 |
| Contig49_gene_208 | atggataaaaattattatcgtgcagtgttgcacttcttgttataattgttggtgct | 331 |
| Contig49_gene_226 | gtggaagtgataatatgtaaatataaaaactgttgcattagctgtt | 332 |
| Contig49_gene_239 | atgctgattatgcaattctgttttattgaccatgccagcgtaagtgcagcgaacttgaagacattcaag tcaca | 333 |
| Contig49_gene_246 | atgaataacactactaaaatattaattggagttcttatggactgctt | 334 |
| Contig55_gene_2 | atggaaacagaaaatttaattattgtaattcttttagttttaatagctatgccggaattttc | 335 |
| Contig55_gene_4 | atgttttttggttatattattattgcatttattgttataggaggatcttattcggtattgct | 336 |
| Contig55_gene_7 | atggctttgcttattctttgcaatgtcatgtgtctgcaagcaatgcaagtgataattggatgatgattaacca tttcagacagtaattcactagatctttgtatctacatcaaat | 337 |
| Contig55_gene_13 | atgaacaataaatactttttaggaataattataataattgcagtt | 338 |
| Contig55_gene_23 | atgctttaaatgataaatctgaactattaaaatcattatttcatttttgctaatagttctaattacaa gttttaattcagtttatgca | 339 |
| Contig55_gene_40 | atgaaaaataattcttggaacatgtatcttattcttgttgattagtgtcgcatatgca | 340 |
| Contig55_gene_45 | atgaaattaatttaaaaagagttatttgattttgatttgcatttcctcagcaagtatca tttcagca | 341 |

FIG. 9-1

| Gene Number | Optimised Codon Nucleotide Sequence | SEQ ID NO: |
|---|---|---|
| Contig40_gene_34 | atggtgctggcgctgagcattattctgctgagcagcattgcggcggagcgcg | 342 |
| Contig40_gene_35 | atgagcacctttattctggtgattattctggcgcattattctgattattgcg | 343 |
| Contig40_gene_39 | atggataacaaaaaaatttttgtgattgtggcgctgctgcgattgtggcgcagcgtgagcgcg | 344 |
| Contig40_gene_40 | atgaacaacaaaaaaatttttgcgcgattgcggcggctgcgattattgcgcgattgtgcgcgcagcgtgagcgcg | 345 |
| Contig40_gene_41 | atgaacgcgaaaaaaactgaccattctggcgcggcgctgcggcgattctggcgattgtggcggcagcgtgagcgcg | 346 |
| Contig40_gene_51 | atgattgctgctgctgacctttagcacccgtgcgcgattgatatgcgattgatgcaaacctgacc | 347 |
| Contig40_gene_54 | atgattattgcgattattttatgtataaccgcgtgcgcaacaaacgc | 348 |
| Contig40_gene_63 | atgaacaaagtgcagctgagcagcattctcgcgctgttctgttctgagcctgcgttctgagctgcggtgtgagcgcg | 349 |
| Contig40_gene_70 | atgcgcaaagaaattatttagcattctggtgattgcgattttgcgtattagcgtgattccgaccgcgttagc | 350 |
| Contig40_gene_72 | atgaacaaaaaaacgctttaaactgctgctgaccatttttattgcgtcgtttgcgctgattaacacctgcttttattctgaacgataacctgagc | 351 |
| Contig40_gene_75 | atggtgtgattctgtctgattacctgctgattctgagcgtgcgattctgagcctgcgaccattgattatagc | 352 |
| Contig40_gene_105 | atgaacattaacctgaaaaaaattacctttcgtgcctggtgctgtgctgctgattgcgctgattagcttaacagcattagcgcg | 353 |
| Contig40_gene_119 | atgaacaaccagaacaaatatgctgcattgtgctggcgggcggcatgagccgcgccgcatgggccag | 354 |
| Contig40_gene_161 | atggaagatcgcaaagcgaaattttattgtgtatgtggtggtgctgcctgctgcgtttattttgcagcagcaccgtgtttagcatgaccgggcctgagc | 355 |
| Contig40_gene_163 | atgaacattctgattaacggcacccggcgcgattgcattgcattgcgattctgattgtgctgtttatgggcgcgagcatgagcattagccaggc | 356 |
| Contig40_gene_164 | atgattattgtgaccaccattgctgcgtgattctgattgtgctgtttatggcctgttccgggcctgaccaacagc | 357 |
| Contig40_gene_165 | atgagcgatgtgggcaaaaacgcgataaaacgcgcgaaatttgcgaaattttgcgaaacccgcgttctggcgctgggcctgagcaacattgcggcg | 358 |
| Contig40_gene_169 | atgaaaagcgataaacgcgcaaacggcgaaattttgcgattttttgcattatctgtttctgcgcgcgcgtttag | 359 |
| Contig40_gene_179 | atgattaacggcattatgcattatgatcaaacagaaagtgattaccgcgtttgcattattctgtttctgcgcggcgttctgcgcggcgtttag | 360 |
| Contig40_gene_187 | atgttttaacaaaaaatggtgctggcattagcctgctgcgggtgattttttgcgagcatgtgcattgtgagcgcg | 361 |
| Contig40_gene_203 | atgaaaaccaacctgaaaaaaccaccattattctgcgcgctgcgattctgattctgagcattgcgcgat | 362 |
| Contig40_gene_228 | atgaacagcaaaggcaaatatctggtgctgtttctgattctgagcttttagcattattagcgcgagcgcttgc | 363 |
| Contig40_gene_231 | atgaaaaaaacctgagcctgaaaaaacattctgattctgagccctgattttctgttgtgctgagcattggcagcagctttgcg | 364 |

FIG. 9-2

| | | |
|---|---|---|
| Contig40_gene_232 | atgaaacgcaacacattttatttattctgctgtgtgaccctgtttctgattagcatgagcgtggtgagcgcg | 365 |
| Contig40_gene_248 | atgaaaaaaatgaaatggcgagctatattattctgattgcgagcgtgctggcgattctgtatgcg | 366 |
| Contig40_gene_251 | atgccgaaaattgcgaaactgtgaacaaactggcggatccgaaaacattccgcgtttgcggtgatt | 367 |
| Contig40_gene_252 | atgtttaactgcgcgattgtggttgtatctggcctgcctgcgattttgcagcctggcgaccgtgggccc gggcgtgaaagatccg | 368 |
| Contig40_gene_260 | atgtttgcgattgtgagcctgagcgcggtgagcgcgagcgatgattttagcagcagcctgcgatatcgagcgatag cgat | 369 |
| Contig40_gene_269 | atgaaacgcgctataaagtgctgtttctgctgcgattctgaccattattagcattaacgcgattagcgcg | 370 |
| Contig40_gene_296 | atgctgtttagcgtgattgcgaccgtgagcgcgacctgc | 371 |
| Contig40_gene_297 | atgtttattaaaattgccgcgatacccgtgattattctgctg | 372 |
| Contig40_gene_306 | atgaaagcggtgattccgcgcggcctggcaccgcttctgccggcgaccaaagcagccgaaagaaatgct gccggtgtatgataaaccgaccattcag | 373 |
| Contig40_gene_317 | atgattaaaaaccgatgtgctggtgattgcgcgggcccgcggcggcagcagcgcttgcgcgcgaaaggcgg c | 374 |
| Contig40_gene_346 | atgaagataaacctgctgaaaaaccgcaaaactgattctgattagcatttttctggtgatgcctgctgcgattagcgc ggtgagcgcg | 375 |
| Contig40_gene_349 | atgaaccgcaacaaaaattattgtgctgtgttgctgattgcggtgggctttaccatggccgggcgtgcgc g | 376 |
| Contig40_gene_352 | atgaaaaaagcgtgttaaaattctgattgcgctattctgatcctgattgcggtgcggtgagcgctgc | 377 |
| Contig40_gene_411 | atgaaaaaaaacattttctgctgctgattgcgctattctgattgcgcggtgatgcgggatccgctgacggctgc | 378 |
| Contig40_gene_431 | atgctgattgcgaaaacaaccgcaccgattaccatgccattgcattgcagcctgttgttattgcgcgtatcgc | 379 |
| Contig40_gene_448 | atgagcgaaaaacaccgcaccctgattactattctgattgtgaccattgcgcgcgtttattatt | 380 |
| Contig40_gene_466 | atgggcaaaattttaaaattgtgaccattattctgattgtgctgcgattctggggcgtgttatttatag cgatgccatagcgaa | 381 |
| Contig40_gene_483 | atggataaaaccattatttattgcggcggtggcgattctggtgatt | 382 |
| Contig40_gene_501 | atgaaactgaacaaatttttattagcattattttctgagcattagcgcgattagcgcg | 383 |
| Contig40_gene_553 | atgaaaaaaaattgcgatttattctggcattgcgttctggcgtttcgtgttattgcggcgagcagcgcg | 384 |
| Contig40_gene_636 | atgaacttttaacaaagcattattttctgctgtgttattgcgagcgtggcattgtggcggcg | 385 |
| Contig40_gene_721 | atgaaacgcagcattacctttaccgcgattattctgagcctgtgattctgttctggtgattgctatgcgagcgcg | 386 |
| Contig40_gene_730 | atgggcattaccttttaaaaatgtgaccgcgcgctggccaccctttagcgaaccgctgggcaactatct gagccagtttattccgtat | 387 |
| Contig40_gene_732 | atgatagcgcaaaaactgattctgtgaccgcgttctgcgattgtgagcattgcgagcgtgagcgcg | 388 |
| Contig40_gene_733 | atgaacgtgaacaaaaattttttctgctgtgattttattattagcattagcattgcgggcgtgtattgcgcgga | 389 |

FIG. 9-3

| | | |
|---|---|---|
| Contig40_gene_749 | tattcatcaggatagcgatctgaccgcg | 390 |
| Contig40_gene_750 | atgattctgcgctgttttgctttattgtgattggcagcgcgagcgcggcgagcgcggcg | 391 |
| Contig40_gene_762 | atgattagcctgctgctgattagcattgcgctggcgctgcagcggcgcatgagccgcgtgcagcgccatgagcccgaacggcctggtggcgcgcgtggcgtgcatga tctgcgattgat | 392 |
| Contig40_gene_766 | atgctgaaaaccaaactgtgcggcattagcctgcggcattagccgtgattgcggcgggcgtgctgggcgtgctgggcagccatgc g | 393 |
| Contig40_gene_769 | atggaaattgtgctgtcgtgcgtgaccggcagcgtggcggcgtggaaactggcgcgcgaatttaaacgcca gggc | 394 |
| Contig40_gene_787 | atgtggtggcgaccattatttttgcgagcagcctgtttgatgcgctgtatggctttaaaaac | 395 |
| Contig40_gene_815 | atgattctgcgcgattctgcgtggatcatgacccgcggtgagcgcg | 396 |
| Contig40_gene_824 | atgaacaaacgcattttctgatctgtatattgcgctgattttattagcctgctgagcttagcgcggtgagcgcg | 397 |
| Contig40_gene_828 | atgaatataacaacaaaactattttttctgctgctgatattccgcaggcgatttat | 398 |
| Contig40_gene_834 | atgaacagcaacaaaacctatgcggtgctgtgcggcctgctgcgattattctgacgcgattagcgc | 399 |
| Contig40_gene_835 | atgattaacaaacgcattagccgcgatctgctgattattctgtgttttctgattattggcctgagcgcggtgag cgcg | 400 |
| Contig40_gene_836 | atgatttaaaaagcgattccgctgtttgcgctgctgctgattctgttttattattggcagcagcgcg | 401 |
| Contig40_gene_837 | atgaaactgaaaaatttagcctgcgattctggtgatgttgcgcgattctggcgattctgcgcggtgagcgcg | 402 |
| Contig40_gene_841 | atgattctgattagcctgctgatctcgtgagcgcattattagcgcgttgctgtgcattgcggcgcgggcgcgtgaccgcg | 403 |
| Contig40_gene_847 | atggataacagcaacattattattagcgtgattattgctgctgaaattgctgcgcggggcggggcgtgaccgcg | 404 |
| Contig40_gene_848 | atggataacagcagcattctgattagcgtgattagcgcgattgatattgctgcgcggggcgtgaccgcg | 405 |
| Contig40_gene_867 | atgcgcaaagaaattctgattgcgggttattattgcgattattctgatttctgtgcgcggcgtgtttgcg | 406 |
| Contig40_gene_872 | atgctgattagcattgtgctgattatctgatttatcctgattgctgattctgcggcgcagcatctg | 407 |
| Contig40_gene_900 | atgaaagaaattgaagcgggcatgattagcgcgggcgcgtctgcccggctgctggcctg | 408 |
| Contig40_gene_906 | atgtttgaagcgggcatgattactgtgggcgcgcagcctgcgctcgtgcgggtgtgagcgtgagcggc | 409 |
| Contig40_gene_909 | atgaaaaactgaaaattattggcctgattctgattctgcgcggtgtgtgagcggc | 410 |
| Contig40_gene_930 | atgaaaccgctgattattaaaattgcattttgcaacaaaaaattttatttttacccctgatgattgtgatgct gctgagcctggcgctgagcggtgagcgcg | 411 |
| Contig40_gene_964 | atgagcattaaacgcattctgctgaccagcctgatgctgttatattttagcattagctttgtgagcgcg | 412 |
| Contig40_gene_975 | atggataaagtgggcattattggcgcggcagcctggcacgcgctgcgcagaccgtggcgaacaacgtg | 413 |
| Contig40_gene_982 | atgatttgcagcattcaggcgtgcagcgcgagctgcacgcgggtgtatgtgggcccg | 414 |
| Contig40_gene_996 | atgaaaattagccgcattattctgattctgctgctgttttgtgtttttgaattggcctgtttagcagcagctatac | 415 |

FIG. 9-4

| | | |
|---|---|---|
| Contig40_gene_1008 | cattgtgaacgcg | 416 |
| Contig40_gene_1021 | atgattctgattattagcctgctgttctgattagcctgctgcgcggcgagcgcg | 417 |
| Contig40_gene_1025 | atgaaactgtataaaaacagcattattctgctgattctgattctgagcattggcgcggcgcg | 418 |
| Contig40_gene_1029 | atgcggtgattctgattattctgtttagcctggcaccgtggcgagcgaaacattgtgatt | 419 |
| Contig40_gene_1036 | atgcgcaaccgaaagattatattatgaaaaccgattatctgattatctgatggcgctgctgctgattagcattgt gagccgattgcggcg | 420 |
| Contig40_gene_1074 | atgaacaacaaaaaaattttgtgcgggcctgcgattctgcgattgtgctgatggcagcgtgcg | 421 |
| Contig40_gene_1084 | atgaaaaaccatgaaaagcaaactgttattctgctgattattattagcattctgattattagcattagcagcgtgag cgcg | 422 |
| Contig40_gene_1088 | atgatgaaaatgaccaaaaaaaacctgttctgctgatttctgctgtgattctgatttatccattggcgcggtgag cgcg | 423 |
| Contig40_gene_1089 | atggtgattatgaacaacaaaaactgtttattgtgagcctgattatctgaccattggcgcggtgag cgcg | 424 |
| Contig40_gene_1093 | atgaaatttaacaaaaaccgcgcattagcgcgattagcattattctgttctgagcattagcatggcgtgag cgcg | 425 |
| Contig40_gene_1097 | atgtttattctgaaatttgaaattaaacgcagccctgattttattagcattctgcgattctgattctgagcattgg catggcgagcgcg | 426 |
| Contig40_gene_1098 | atgcaggcgattattccggtgaaagataacttctctgattctgattgtgaccaacatgaaaaaagcgatttaaacgcat tttatttgcctggtgctgctagccctgcctgattgccgcggtgagcgcg | 427 |
| Contig40_gene_1099 | atgaactttaaaaaactgctgatgattgctgattctgcgattctgctgctgtgctgctgagcgtttgctgctgagcgtgggctttagcaccgcgagcgc g | 428 |
| Contig40_gene_1104 | atgaaaattaaaagcgttttgtgattctgctgattgcctgttctgctgttaccattggcgagcgtggcgcg | 429 |
| Contig40_gene_1106 | atgaccgtgagcgtgtttattagcgcgagcgtttgttgcaacgtgctgagcaacgcgataacgc | 430 |
| Contig40_gene_1158 | atgaaagtgctgaaattgcgattattatgctgattctgattattagcctggcgcgggtgagcgcg | 431 |
| Contig40_gene_1176 | atgaacttaaaaacaaaggcagccgtgattctgattagcctgcctgttatttgcgatttattggcattggcatggcgag cgcg | 432 |
| Contig40_gene_1198 | atgggcaaattaaatttattctgctgggcgctgttctgattttgcggcattgcg | 433 |
| Contig40_gene_1215 | atggatagcaaaaattctgatgattgcggttgcgctgattgcgattgtggcgcgtgagcagctgagcagcgcg | 434 |
| Contig40_gene_1238 | atgaaactgaaaagcaaatatattattttgttctgcattctgtttagcattagcattagcaccgtgagcgcg | 435 |
| Contig40_gene_1247 | atgaactatagcattattattttttctgatgatgcgctgatggctgatgcgagcattcaggtgtgcgg | 436 |
| Contig40_gene_1254 | atgaaatttaacagccgcgtgctgctgagcctgctgttgtgctgaccattctgtgtgagcagcgtgggcgc g | 437 |

FIG. 9-5

| | | |
|---|---|---|
| Contig40_gene_1270 | atgaaaaaaaaaccaccattattctggtgattctgattgcgctgattgcgtgc | 438 |
| Contig40_gene_1274 | atgaaaaaacaaaagcctgattctgattagcctgattaccattattagcattgcagcgtgtggcg | 439 |
| Contig40_gene_1296 | atgcgcagcaccattctgcttattgcctgagcgcgagcaccgagccgagcctgaccacggccgc | 440 |
| Contig40_gene_1331 | atgctgctgattgctttattgcctggtggaagcgattctgatgtggcgctgtgtggaagatctggcgattag<br>cgtgcgcaaaagcccg | 441 |
| Contig40_gene_1350 | atgaacaaaaaaattattctgagcctgctgctgtgtggtggcgattagcgtgagcgcggtgcggcg | 442 |
| Contig40_gene_1351 | atgagcctgagcattttgtgctgatgtggcgcggcttattaacaaacgcattctgctgattttgtgtttct<br>gattttttattagcattgcagcgtgtggcg | 443 |
| Contig40_gene_1355 | atgaacacaaaaaattattatgagctttctgctggtgctgctgattgcgtgtgctgagcgtgagcgcggtgagcgcgcg | 444 |
| Contig40_gene_1364 | atgaaattcagcgcggcatttatattattctgacctgctgtgtgtttagcctgagcgcgagcgcgagcgcgcg | 445 |
| Contig40_gene_1367 | atgaactgaaagtgatcaggataaatgcctggctgcgcggcgtgtgctgattgctgcccggtgaacgcgagcat<br>tagcccgaaaac | 446 |
| Contig45_gene_8 | atgaacgcgccgcagcaaactgattattgcgattctgattgtgattattatt | 447 |
| Contig45_gene_20 | atgaaacgcagcagcaaaaataaaattgcgattattgcgattggcggcgcccggccgcatgatggcgattcgcgcggaaattct<br>gggcccgaacgcggtgcattctggaa | 448 |
| Contig45_gene_21 | atggcgaacgaaggcggcgccatctgaaaaccattctgatgatgattattctgcgttattattctgatttgcgcctg | 449 |
| Contig45_gene_30 | atggataacaaaattaaagcgggcattgcgctggcattgtgctggtgattgcttagctttattaa<br>cgaaagcaac | 450 |
| Contig45_gene_35 | atgtttaaagtgagcaaaagcattctgattgtgcctggtgtttctgctggtgagcaggcgagcgcg | 451 |
| Contig45_gene_36 | atgtgtatgatatgaaacgcgccgcgctttatctgattctgtttattattctgctgattctgcgggattgcg | 452 |
| Contig45_gene_60 | atgaaaattaccgtgccggggcgtgggctatgtgggcctggcctgagcctgctgctgcgcagaaacatgatgtgac | 453 |
| Contig45_gene_64 | atgaacctgatgaaattaccgtgcggcgtgggctgggctatgggcctgagcattgcgattctgctggcgcagaaaca<br>tgatgtgaccgcg | 454 |
| Contig45_gene_89 | atgaaattcgctataaaacctgctgaaagtgttaccattgttctggtgctgctgattagctgcggcttgcgag | 455 |
| Contig45_gene_91 | atgaaaattcgctataaaacctgctgaaagtgttaccattgttctggtgctgctgattagctgcggcttgcgag<br>cgcg | 456 |
| Contig45_gene_93 | atgaaaattcgctataaaacctgctgaaagtgttaccattgttctggtgctgctgattagctgcggctttgcgag<br>cgcg | 457 |
| Contig45_gene_100 | atgcagcgcagcctgttgataagtgaaaaccagcctgtgatgctgcgagcttttttgcctgtg | 458 |
| Contig45_gene_106 | atgaaattaaaaacagcaccatattctgctgtgagcctgattagcattttctgctgagcattagcgcggcgagcgcg | 459 |
| Contig45_gene_116 | atgaacagcaaaaaattgctgcttgtgctggcattatctgcgatttggcgagcttgtgggcagcgcgagcgcg | 460 |
| Contig45_gene_159 | atgatgaatgcaaactggtgctgattggctttggcgcgtggcgcgcaggggcgtggcgcgcgattagcgcggcgagcgcgattagcgcggcgagcgcg | 461 |

FIG. 9-6

| | | |
|---|---|---|
| | agaaatgattaacgaaaaattggcattagcctgaaagtg | |
| Contig47_gene_7 | atgatgcgcaaaaccattttttggcgtgattttattgtgtttattctgtttagcattagcaccgtgagcgcg | 462 |
| Contig47_gene_13 | atgaacaaacagaacgtgtttgcgtttgcgcctgctgattctgctgaccattatctgctgagcgtggcggtggc | 463 |
| Contig47_gene_57 | atgctgaacaaaaaattattattttctgaccttattctgattctgagcattagcagcgcgagcgcgagcgcg | 464 |
| Contig47_gene_60 | atgggcgtgctgcgagcgtggcggggcgcattttttttgaagcgggcatgattgcgacctgcacc | 465 |
| Contig47_gene_62 | atgtttagcgtgagcctgaacaaactgaaaattggccgcgtgtttatttgcctgtttatctgtgtttattagctg cagcattaactgcgtgtttgcg | 466 |
| Contig47_gene_98 | atgggcggcgaaattattaacaacgaaaaactgaaactgattctgattctgacc | 467 |
| Contig47_gene_125 | atggataaaaaaatgattgtgagcgtggcgtgtttctgctctgctgcgttcgggcgtggcgctggtgagcgtgtttgatga aagcaacagc | 468 |
| Contig47_gene_140 | atgaaaattagccgcattattgtgctgctgatgattctgattctgattttaccgcgcatgtgtatgcg | 469 |
| Contig47_gene_146 | atgatagcaaaaaaattctgtgattggcgtggcctgagcgcggcattggcaaaagcaccgtggcgagcagcgtgagcgcg | 470 |
| Contig47_gene_160 | atgaaaccgtatgtgattctgattggcagcgcgcattggcaaaagcaccgtggcggaactggcgaaaac cctgaacattaaacatctggtg | 471 |
| Contig47_gene_197 | atgctgattagcgtgctgggcgtgggcgtgattgtgattattattggtggtgcggcg | 472 |
| Contig47_gene_208 | atggcgacccgcaccaaacagacacattgccgcctgtatagctttcatggcgccgctttctg | 473 |
| Contig47_gene_253 | atgaaactgagcaacgcgataaaatatctgattgtgtggcattattttgcctggcgctg | 474 |
| Contig47_gene_269 | atgaaagtgcgattctgggcgcgggcgcgtctatcgcaccatgcgagcgcattaccaacttt | 475 |
| Contig47_gene_304 | atgagcgtgattctgattctgtttctgtatattctgctggcgctgatt | 476 |
| Contig47_gene_306 | atgaacaaaaaactgaaaattattgcgcgaccgtgattctggcggttggtgattgtgctgagcgcgtttatttta | 477 |
| Contig47_gene_309 | atgaaaccaaaaaactgattattgcgaccgcgcgattctggcgtgtggcaacaaccag tgtgaacatgggcaac | 478 |
| Contig47_gene_349 | atgctgttgctggcgttgcgattatttttctgggctatagcattagcctggtgggcatgattggc | 479 |
| Contig47_gene_353 | atgaactgaacgatgaattatttttaaagtggcgctgattaccgcgctgttgggcatgattggc | 480 |
| Contig47_gene_356 | atgaaaactatttttgatatattaaagataaagtggcggtggtgaccggcgagcagcgcctggcctgcagatt | 481 |
| Contig47_gene_375 | atgaccttaacaacctgcgcattaacattaaagattgcattgtgatttgtgtttaccgtgctgctgag cattctgcggtgagcgcg | 482 |
| Contig47_gene_381 | atgaaatttaaaaaaatatctgtgtttattctgtgattgcgctgattgcattattgagcgtggcggtggcg | 483 |
| Contig47_gene_391 | atgataaaaaaatgaccgtgctgtgttgtgcgcttttgcctgctgctgggcagc | 484 |
| Contig49_gene_3 | atggatcgcaaagatattattctggtgctgattattattagcctgctgccgctgggcctgcataacca tcaggtg | 485 |
| Contig49_gene_4 | atgaccagcgaattatgattctgaccccgaccgcggtggtgctggcggcggataagcgcggtgaccattagcgatat taaa | 486 |

FIG. 9-7

| | | |
|---|---|---|
| Contig49_gene_25 | atgcgcaaaaaattctgtttctgaccctgatgattctgatttgcttaccctgaacagcgtgtgcg | 487 |
| Contig49_gene_43 | atgcgcctgcgctatttttgcgattattagcctgattctgatttttctggtgccggtgagctttgcg | 488 |
| Contig49_gene_44 | atgtttattggcctgctgctggtgattgcctgctgtgattattccgattagctttgcg | 489 |
| Contig49_gene_96 | atgctgattggcctgctggtgattgcgcgggcgtgttttatttcagtttaactatgcgaccccgacctatctg | 490 |
| Contig49_gene_128 | atggtgctggtggcggtggtggtgcgattattgcagcaccgcgttctgctgaactatgatgaaaccgtgaaatatacc | 491 |
| Contig49_gene_152 | atggataaaaaacctgcgattattgtgattgtgattgcgcgtgggc | 492 |
| Contig49_gene_167 | atgaacaacaaaacctgtttattattggcctgttatttgcctgctgctgttaccattccgatggtgagcgcg | 493 |
| Contig49_gene_172 | atgattaaaaccgataacaaaggccagattaccgtgaactgctgctgctgctgagcttt | 494 |
| Contig49_gene_175 | atgctgaaccgcaaagccgctgattttagcctgtgtgctgtttatgctgagcattagcgcggtgagcgcg | 495 |
| Contig49_gene_180 | atggataacaaagcgattattggcattgtgattgcgctgattgtgctggcgtgtttgcgtat | 496 |
| Contig49_gene_183 | atgagctattttaacaaagccatatttggaacattctgctgatttgcctgctgattgccacctggcagcgcggatggg cagcgcgagcgcg | 497 |
| Contig49_gene_184 | atgaaaaacaaagcgatgtttctgattagcgcgctgctgatttgcggtgattctgagcctgagcgcggtgagcgcggc ggatgatgcgattgcg | 498 |
| Contig49_gene_194 | atgaaatttaacacaaaagcctgattattgcgattttgtgattgcgcgtttagcagcattagcgtgattgcg | 499 |
| Contig49_gene_208 | atgataaaaaaatattattggcgcgcggtggtgctgctgctggtgattattgtgggcg | 500 |
| Contig49_gene_226 | atgaaggcgataacatgtgaacattaaaaccgtgacctgcgctgg | 501 |
| Contig49_gene_239 | atgctgattatgcgattctgctgctgctgaccatgcgagcgtgagcgagcgaactgaagatattcaggtgac c | 502 |
| Contig49_gene_246 | atgaacaacaccacaaaaaatctctgattggcgtgctgatggcctgctg | 503 |
| Contig55_gene_2 | atgaaaaccgaaaacctgtgattattgtgattgcgctgctgattgcgatggcgggcatttt | 504 |
| Contig55_gene_4 | atgtttctgattctgctgtgtttgcgtttattgtgcgcgcagctatagcgtgtttgcg | 505 |
| Contig55_gene_7 | atggcgctgctgatctgatgcgcgatgagcgcgtgagctgcgtgcaacgcgagcgatacctgatgatcgtgatgaccattag cgatagcaacagcctgatctggtgagcaacagcaac | 506 |
| Contig55_gene_13 | atgaacaacaaatattctgggcattattttctgcgtg | 507 |
| Contig55_gene_23 | atgctgaacgatacaagcgaactgctgaaagcctgagcattctgtttctgcgtgttgctgattaccagctt taacagcgtgtatgcg | 508 |
| Contig55_gene_40 | atgaaaaaattctggcactgcattctgttctgatagcgtgctgtatgcg | 509 |
| Contig55_gene_45 | atgaaattaacctgaaacgtgattctggcattctgattctgattgcattgcagcgcgagcattattag cgcg | 510 |
| For consensus SEQ ID | aaa aaa ctg att att att ctg ctg ctg att ctg att ctg ctg agc att | 511 |

FIG. 9-8

| NO:117, optimised coding sequence: | | |
|---|---|---|
| For consensus SEQ ID NO:119, predicted coding sequence | AAA AAA ATT ATT ATT ATT TTA TTA TTA ATT TTA TTA ATT TCA ATT | 512 |
| For consensus SEQ ID NO:119, optimised coding sequence | AAA AAA ATT ATT ATT ATT CTG CTG CTG ATT CTG CTG ATT AGC ATT | 513 |

CELL-PERMEABILISING PEPTIDES AND POLYPEPTIDES FOR MICROBIAL CELLS

RELATED APPLICATIONS

This is a national phase application of PCT/NZ2008/000247, filed Sep. 25, 2008, which claims the benefit of U.S. Provisional Application No. 60/975,104, filed Sep. 25, 2007, U.S. Provisional Application No. 60/989,840, filed Nov. 22, 2007, and U.S. Provisional Application No. 60/989,841, filed Nov. 22, 2007, the contents of all of which are incorporated by reference herein in their entirety.

FIELD OF THE INVENTION

The invention relates to compositions and methods for delivering inhibitory molecules into microbial cells, in particular, methanogen cells. Specifically, the invention relates to signal peptides and polypeptides comprising these peptides, as well as polynucleotides which encode these peptides or polypeptides. The invention also relates to expression vectors and host cells for producing these peptides or polypeptides. The invention further relates to methods for detecting, targeting, permeabilising, and inhibiting microbial cells, especially methanogen cells, using the disclosed peptides or polypeptides, polynucleotides, expression vectors, and host cells.

BACKGROUND OF THE INVENTION

In New Zealand, agricultural activity accounts for the majority of greenhouse gas emissions. Therefore, reducing agricultural emissions of greenhouse gases is important for meeting New Zealand's obligations under the Kyoto Protocol. The Protocol requires reduction of greenhouse gases to 1990 levels by the end of the first commitment period (2008-2012). To this end, agricultural sector groups and the New Zealand government established the Pastoral Greenhouse Gas Research Consortium (PGGRC) to identify means for reducing New Zealand's agricultural greenhouse gas emissions.

An important part of the PGGRC's activities has been research into reducing methane emissions from New Zealand's grazing ruminants. Mitigating methane emissions from ruminants is of commercial interest for two reasons. First, failure to meet commitments under the Kyoto Protocol will force the government to purchase carbon credits. This is currently estimated to cost $350 million. Second, methane production results in the loss of 8-12% of the gross energy produced in the rumen. This energy could be used, instead, to improve ruminant productivity.

Methane is produced in the rumen by microbes called methanogens which are part of the phylum Euryarchaeota within the kingdom Archaea. Most methanogens grow on $CO_2$ and $H_2$ as their sole energy source, but some can use acetate or methyl compounds for growth. Several different genera of methanogenic archaea exist in the rumen, but species of the genus *Methanobrevibacter*, especially *M. ruminantium*, and *M. smithii* are thought to be the predominant methanogens in New Zealand ruminants. *M. ruminantium* is currently the subject of a genome sequencing project funded by the PGGRC. The project is the first genome sequencing of a rumen methanogen and it aims to build a better understanding of the biology of *Methanobrevibacter* to discover targets for inhibition of methane formation.

Reducing methane production in the rumen requires the inhibition of methanogens or the inactivation of their methanogenesis pathway. A means of inhibiting methane production is to deliver specific inhibitory molecules into methanogen cells. This may be achieved, for example, by coupling inhibitory molecules to cell-permeabilising peptides. In microbial cells, signal peptides mediate the translocation of extracellular proteins from the inside to the outside of the cell and are suitable for the transport of inhibitory molecules. Therefore, it would be useful to identify signal peptides that have the ability to permeabilise methanogen cells and deliver inhibitors.

Signal peptides, or signal sequences, are typically included in precursor proteins secreted from prokaryotic and eukaryotic cells. The signal peptides are part of a cell-permeabilising extension at the N-terminus of the precursor. The primary amino acid sequence of signal peptides is not conserved apart from the cleavage site for signal peptidase (von Heijne, 1985). Yet, signal peptides do share structural similarities. Signal peptides typically include one to five positively charged N-terminal amino acid residues (n-region) followed by 10 to 15 hydrophobic amino acid residues (h-region). A glycine or proline residue is usually located within the hydrophobic domain and a threonine and/or serine residue(s) form a polar domain (c-region) near the cleavage site (Inouye and Halegoua, 1980; Vlasuk et al., 1983, von Heijne, 1985).

A loop model for signal peptide translocation has been proposed (Inouye et al., 1977; Inouye and Halagoua, 1980) whereby the positively charged N-terminus of the signal peptide interacts with the negatively charged inner surface of the cell membrane. The hydrophobic domain is then drawn into the hydrophobic lipid bilayer of the membrane by forming a loop. The loop eventually includes the cleavage site, which is exposed to the signal peptidase for removal of the signal peptide. One of the barriers to inhibiting or limiting methane formation is the ability to deliver inhibitory compounds into methanogen cells. Thus, there is a need to identify signal peptides that are able to attach to cell membranes and to transport molecules across the lipid bilayer, as useful carriers for cell inhibitors.

SUMMARY OF THE INVENTION

The invention features an isolated signal peptide or polypeptide comprising this peptide, which comprises at least one amino acid sequence selected from the group consisting of SEQ ID NO:1-172. In a particular aspect, the peptide or polypeptide comprises at least one amino acid sequence KKLIIILLLLILLLSI of SEQ ID NO:117, or at least one amino acid sequence KKIIIILLLLILLLISI of SEQ ID NO:119. In another aspect, the peptide or polypeptide comprises a fragment, for example, comprising at least one amino acid sequence comprising amino acids 3-14, 3-16, or 2-16 of SEQ ID NO:117, or at least one amino acid sequence comprising amino acids 3-15, 3-17, or 2-17 of SEQ ID NO:119. In a further aspect, the peptide or polypeptide comprises a fragment comprising at least one conserved core sequence of SEQ ID NO:1-172, as disclosed herein. In a still further aspect, the peptide or polypeptide is encoded by at least a fragment of a polynucleotide selected from the group consisting of SEQ ID NO:173-341 or SEQ ID NO:342-533.

The invention also features an isolated polynucleotide comprising a coding sequence for at least one signal peptide or a polypeptide comprising this peptide. In one aspect, the polynucleotide comprises a coding sequence for at least one amino acid sequence selected from the group consisting of SEQ ID NO:1-172. In a particular aspect, the polynucleotide comprises a coding sequence for at least one amino acid sequence KKLIIILLLLILLLSI of SEQ ID NO:117, or a coding sequence for at least one amino acid sequence KKII-IILLLLILLLISI of SEQ ID NO:119. In another aspect, the polynucleotide comprises a fragment of a coding sequence, for example, a coding sequence for at least one amino acid sequence comprising amino acids 3-14, 3-16, or 2-16 of SEQ ID NO:117, or a coding sequence for at least one amino acid sequence comprising amino acids 3-15, 3-17, or 2-17 of SEQ ID NO:119. In a further aspect, the polynucleotide comprises a fragment of a coding sequence, for example, a nucleotide sequence encoding at least one conserved core sequence of SEQ ID NO:1-172, as disclosed herein.

In an additional aspect, the invention features an isolated polynucleotide comprising a nucleic acid sequence selected from the group consisting of SEQ ID NO:173-341 or SEQ ID NO:342-533. In a particular aspect, the polynucleotide comprises the nucleic acid sequence of SEQ ID NO:531, 532, or 533. In another aspect, the polynucleotide is a fragment or an oligonucleotide, for example, comprising the nucleic acid sequence extending from nucleotide 7-42, 7-48, or 4-48 of SEQ ID NO:531, 532, or 533. In addition, the invention encompasses an isolated polynucleotide, or fragment thereof, which hybridizes to any one of the nucleic acid sequences of SEQ ID NO:173-341 or SEQ ID NO:342-533. The invention further encompasses an isolated polynucleotide comprising the complement, reverse complement, reverse sequence, or fragments thereof, of any one of the nucleic acid sequences encoding a signal peptide or a polypeptide comprising this peptide.

The invention features an expression vector comprising a polynucleotide which comprises a coding sequence for at least one signal peptide or a polypeptide comprising this peptide. In one aspect, the expression vector comprises a coding sequence for at least one amino acid sequence selected from the group consisting of SEQ ID NO:1-172. In a particular aspect, the expression vector comprises a coding sequence for at least one amino acid sequence KKLIIILLLLILLLSI of SEQ ID NO:117, or a coding sequence for at least one amino acid sequence KKIIIILLLLILLLISI of SEQ ID NO:119. In another aspect, the expression vector comprises a coding sequence for at least one amino acid sequence extending from amino acid 3-14, 3-16, or 2-16 of SEQ ID NO:117, or a coding sequence for at least one amino acid sequence comprising amino acids 3-15, 3-17, or 2-17 of SEQ ID NO:119. In yet another aspect, the invention features a host cell, for example, a microbial host cell, comprising at least one expression vector.

The invention specifically features an antibody directed to a peptide, polypeptide, or polynucleotide as disclosed herein. In certain aspects, the antibody is directed to at least one signal peptide sequence selected from the group consisting of SEQ ID NO: 1-172, or a modified sequence thereof. In alternate aspects, the antibody is directed to at least a fragment of a signal peptide sequence, for example, a conserved core sequence of a sequence selected from the group consisting of SEQ ID NO: 1-172. In a further aspect, the antibody binds to a polypeptide comprising a signal peptide sequence of any one of SEQ ID NO: 1-172. In alternate aspects, the antibody is directed to at least a fragment of a polynucleotide selected from the group consisting of SEQ ID NO:173-341 or SEQ ID NO:342-533, or a complement, or modified sequence thereof. In another aspect, the antibody includes one or more fusions or conjugates with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein.

The invention also features modified signal peptides and polypeptides comprising these peptides, and antibodies directed to these peptides or polypeptides, including biologically active alterations, fragments, variants, and derivatives described herein. Also featured are polynucleotides encoding these modified peptides or polypeptides, as well as alterations, fragments, variants, and derivatives of the disclosed polynucleotides, expression vectors comprising these nucleic acid sequences, and host cells comprising these vectors. In specific aspects, the compositions and methods of the invention employ these modified polynucleotides, polypeptides, or antibodies, or corresponding expression vectors or host cells. In particular aspects, the peptides or polypeptides are produced as fusions or conjugates with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein.

The invention additionally features a composition comprising an isolated signal peptide (e.g., at least one of SEQ ID NO:1-172, or a modified sequence thereof) or polypeptide comprising this peptide, or an antibody directed to this peptide or polypeptide. Also featured is a composition comprising an isolated polynucleotide (e.g., at least one of SEQ ID NO:173-341 or SEQ ID NO:342-533, or a complement, or modified sequence thereof). Further featured is a composition that includes an expression vector, or host cell comprising an expression vector, in accordance with the invention. The composition can include any one of the biologically active alterations, fragments, variants, and derivatives described herein. The compositions can further include at least one cell inhibitor, and can be formulated, for example, as pharmaceutical compositions or as food supplements, in particular, ruminant feed components.

In a particular aspect, the invention features a composition of the invention as part of a kit for detecting and/or measuring, or targeting, permeabilising, and/or inhibiting microbial cells, especially methanogen cells, in accordance with the disclosed methods. The kits comprise: a) at least one composition as set out herein; and b) optionally, instructions for use, for example, in targeting or permeabilising cells or inhibiting cell growth or replication for methanogens or other microbes. In specific aspects, the peptide or polypeptide comprises at least one amino acid sequence selected from the group consisting of SEQ ID NO:1-172, or a modified sequence thereof.

The invention features a method for producing a signal peptide or a polypeptide comprising this peptide, the method comprising: a) culturing an expression vector or host cell comprising an expression vector, which comprises a coding sequence for at least one signal peptide or polypeptide comprising this peptide under conditions suitable for the expression of the peptide or polypeptide; and b) recovering the peptide or polypeptide from the culture. Also featured are methods for producing the disclosed compositions. In particular aspects, the peptide or polypeptide comprises at least one amino acid sequence selected from the group consisting of SEQ ID NO:1-172, or a modified sequence thereof.

The invention also features a method for producing a signal peptide or polypeptide comprising this peptide, which includes a fusion or conjugate with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein. Such method comprises: a) culturing an expression vector or host cell comprising an expression vector, which comprises a coding sequence for at least one peptide or polypeptide under conditions suitable for the expression of the peptide or polypeptide; b) forming the fusion or conjugate (e.g., by expression of the fused sequence or chemical conjugation to the cell inhibitor); and c) recovering the fusion or conjugate. In particular aspects, the signal peptide or polypeptide comprises at least one amino acid sequence selected from the group consisting of SEQ ID NO:1-172, or a modified sequence thereof.

The invention features a method of permeabilising a microbial cell, in particular, a methanogen cell, comprising: a) optionally, producing or isolating at least one signal peptide or a polypeptide comprising this peptide; and b) contacting the cell with the signal peptide or polypeptide. In a particular aspect, the peptide or polypeptide comprises at least one amino acid sequence selected from the group consisting of SEQ ID NO: 1-172, or a modified sequence thereof. In further aspects, the peptide or polypeptide comprises a fusion or conjugate with at least one cell inhibitor, for example, one or more anti-methanogenesis compounds (e.g., bromoethanesulphonic acid), antibodies and antibody fragments, lytic enzymes, peptide nucleic acids, antimicrobial peptides, or other antibiotics as described in detail herein.

The invention also features a method of inhibiting a microbial cell (e.g., inhibiting growth or replication); in particular, a methanogen cell, comprising: a) optionally, producing or isolating at least one signal peptide or polypeptide comprising this peptide, which further comprises at least one cell inhibitor; and b) contacting the cell with the signal peptide or polypeptide. In a particular aspect, the peptide or polypeptide comprises at least one amino acid sequence selected from the group consisting of SEQ ID NO: 1-172, or a modified sequence thereof. In a further aspect, the cell inhibitor is selected from anti-methanogenesis compounds (e.g., bromoethanesulphonic acid), antibodies and antibody fragments, lytic enzymes, peptide nucleic acids, antimicrobial peptides, and other antibiotics as described in detail herein.

The invention also features a method of inhibiting a microbial cell (e.g., inhibiting growth or replication), in particular, a methanogen cell, comprising: a) optionally, producing or isolating at least one signal peptide or polypeptide comprising this peptide, which further comprises at least one cell inhibitor; and b) contacting the cell with the signal peptide or polypeptide. In a particular aspect, the peptide or polypeptide comprises at least one amino acid sequence selected from the group consisting of SEQ ID NO: 1-172, or a modified sequence thereof. In a further aspect, the cell inhibitor is selected from anti-methanogenesis compounds (e.g., bromoethanesulphonic acid), antibodies and antibody fragments, lytic enzymes, peptide nucleic acids, antimicrobial peptides, and other antibiotics as described in detail herein.

The invention also features a method of detecting and/or measuring the levels of a signal peptide, or a corresponding polypeptide or polynucleotide, comprising: 1) contacting a sample from a subject with an antibody directed to a signal peptide (e.g., at least one of SEQ ID NO:1-172, or a modified sequence thereof) or a corresponding polypeptide or polynucleotide; and 2) determining the presence or levels of the antibody complex formed with the signal peptide or a corresponding polypeptide or polynucleotide in the sample. Such methods can also be used for detecting and/or measuring the levels of a microbial cell, in particular, a methanogen cell.

The invention features, as well, a method of detecting and/or measuring the levels of a signal sequence polynucleotide (e.g., a signal peptide coding sequence, or a corresponding polypeptide coding sequence), comprising: 1) contacting a sample from a subject with a complementary polynucleotide (e.g., a sequence complementary to any one of SEQ ID NO:173-341, or modified sequence thereof); and 2) determining the presence or levels of the hybridization complex formed with the signal sequence polynucleotide in the sample. Such methods can also be used for detecting and/or measuring the levels of a microbial cell, in particular, a methanogen cell.

In particular aspects, the methods of the invention utilize in vivo or in vitro expression components. In other aspects, the methods employ peptides or polypeptides produced by recombinant, synthetic, or semi-synthetic means, or peptides or polypeptides produced by endogenous means.

Other aspects and embodiments of the invention are described herein below.

BRIEF DESCRIPTION OF THE DRAWINGS

This invention is described with reference to specific embodiments thereof and with reference to the figures.

FIGS. 1A-1C: Comparison of Methanobacteriales genomes (FIG. 1A); *M. ruminantium* genome statistics (FIG. 1B); Genes predicted to be involved in methanogenesis in Methanobacteriales species (FIG. 1C).

FIG. 2: *Methanobrevibacter ruminantium* signal peptide alignment. The core conserved region of each peptide is shown in bold.

FIG. 6: *M. ruminantium* genes and corresponding signal peptide scores.

FIG. 7: *M. ruminantium* genes and corresponding signal peptides.

FIG. 8: Coding sequences for signal peptides from FIG. 7.

FIG. 9: Coding sequences for signal peptides from FIG. 7, with codons optimized for expression in *E. coli*.

DETAILED DESCRIPTION OF THE INVENTION

Definitions

Figure 1C:
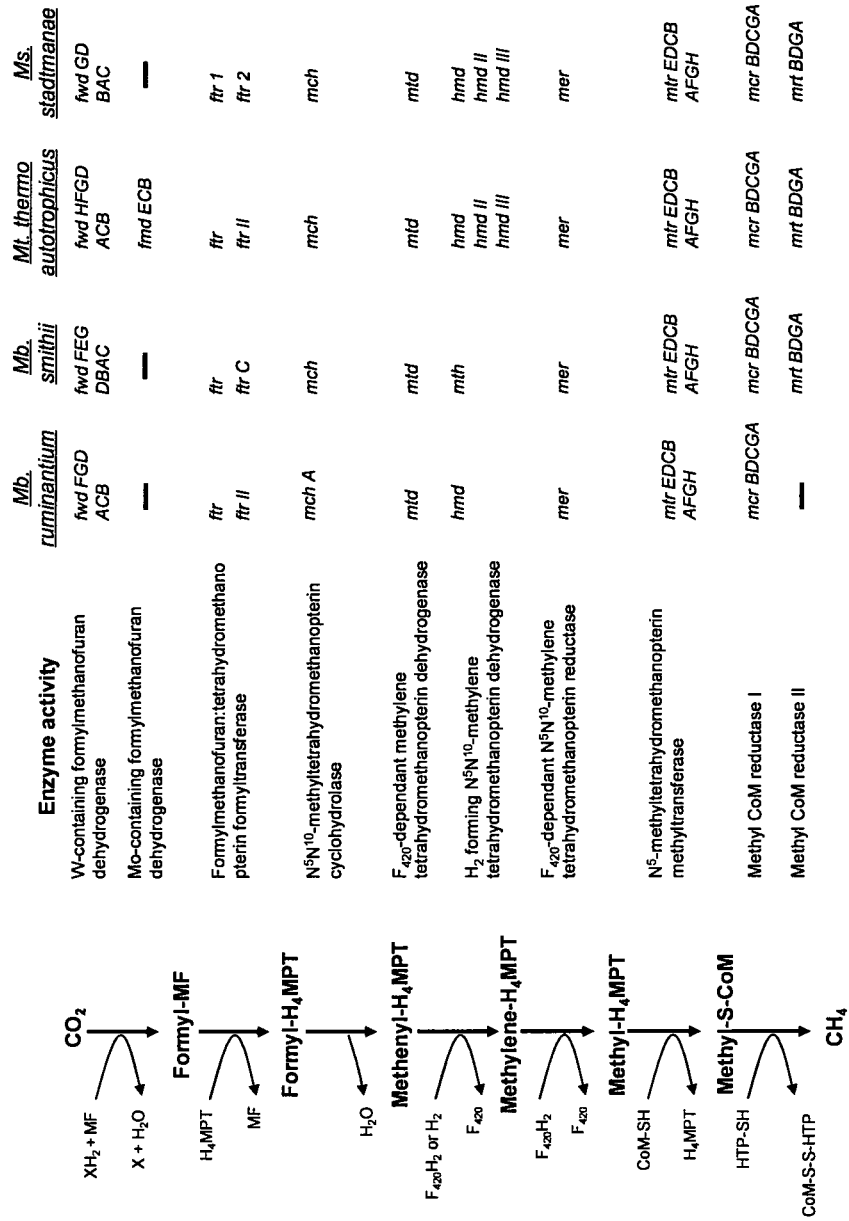

"Altered" nucleic acid sequences encoding signal peptides, as used herein, include those with deletions, insertions, or substitutions of different nucleotides resulting in a polynucleotide that encodes the same or functionally equivalent peptides. The encoded peptide may also be "altered" and contain deletions, insertions, or substitutions of amino acid residues which produce a silent change and result in a functionally equivalent peptide. Deliberate amino acid substitutions may be made on the basis of similarity in polarity, charge, solubility, hydrophobicity, hydrophilicity, and/or the amphipathic nature of the residues as long as the biological activity (e.g., cell-association or cell-permeabilisation) or immunogenic activity of the peptide is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring, recombinant, synthetic, or semi-synthetic molecules. The sequences of the invention (e.g., SEQ ID NO:1-172) comprise at least 5, 6, 7, 8, 9, 10, 11, 12, 15, 17, 19, or 22 amino acids, preferably at least 5 to 10, 5 to 15, 10 to 15, 12 to 15, 15 to 17, 17 to 19, or 17 to 22 amino acids, and, preferably, retain the biological activity (e.g., cell-association or cell-permeabilisation) or the immunological activity (e.g., at least one antibody binding site) of the original sequence. Where "amino acid sequence" is recited herein to refer to an amino acid sequence of a naturally occurring peptide or polypeptide molecule, amino acid sequence, and like terms, are not meant to limit the amino acid sequence to the complete, native amino acid sequence associated with the full length molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

The term "antibody" should be understood in the broadest possible sense and is intended to include intact monoclonal antibodies and polyclonal antibodies. It is also intended to cover fragments and derivatives of antibodies so long as they exhibit the desired biological activity. Antibodies encompass immunoglobulin molecules and immunologically active portions of immunoglobulin (Ig) molecules, i.e., molecules that contain an antigen binding site that specifically binds (immunoreacts with) an antigen. These include, but are not limited to, polyclonal, monoclonal, chimeric, single chain, Fc, Fab, Fab', and $Fab_2$ fragments, and a Fab expression library.

Antibody molecules relate to any of the classes IgG, IgM, IgA, IgE, and IgD, which differ from one another by the nature of heavy chain present in the molecule. These include subclasses as well, such as IgG1, IgG2, and others. The light chain may be a kappa chain or a lambda chain. Reference herein to antibodies includes a reference to all classes, subclasses, and types. Also included are chimeric antibodies, for example, monoclonal antibodies or fragments thereof that are specific to more than one source, e.g., one or more mouse, human, or ruminant sequences. Further included are camelid antibodies or nanobodies. It will be understood that each reference to "antibodies" or any like term, herein includes intact antibodies, as well as any fragments, alterations, derivatives, or variants thereof.

The terms "biologically active" or "functional," as used herein, refer to a peptide or polypeptide retaining one or more structural, immunogenic, or biochemical functions (e.g., cell-association or cell-permeabilisation) of a naturally occurring sequence. As one example, a functional sequence can comprise at least one of the core conserved regions disclosed herein.

The terms "cell inhibitor" or "inhibitor," as used herein, refer to agents that decrease or block the growth or replication of microbial cells, especially methanogen cells. A cell inhibitor can act to decrease or block, for example, cellular division. An inhibitor can decrease or block, for example, DNA synthesis, RNA synthesis, protein synthesis, or post-translational modifications. An inhibitor can also decrease or block the activity of enzymes involved in the methanogenesis pathway. An inhibitor can also target a cell for recognition by immune system components. Inhibition of a cell also includes cell killing and cell death, for example, from lysis, apoptosis, necrosis, etc. Useful inhibitors include, but are not limited to, anti-methanogenesis compounds (e.g., bromoethanesulphonic acid), antibodies and antibody fragments, lytic enzymes, peptide nucleic acids, antimicrobial peptides, and other antibiotics as described in detail herein.

The terms "complementary" or "complementarity," as used herein, refer to the natural binding of polynucleotides under permissive salt and temperature conditions by base-pairing. For the sequence A-G-T, the complementary sequence is T-C-A, the reverse complement is A-C-T and the reverse sequence is T-G-A. Complementarity between two single-stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

The term "derivative", as used herein, refers to the chemical modification of a nucleic acid encoding a signal peptide, or a nucleic acid complementary thereto. Such modifications include, for example, replacement of hydrogen by an alkyl, acyl, or amino group. In preferred aspects, a nucleic acid derivative encodes a peptide which retains the biological or immunological function of the natural molecule. A derivative peptide is one which is modified by glycosylation, pegylation, or any similar process which retains one or more biological function (e.g., cell-association or cell-permeabilisation) or immunogenic function of the sequence from which it was derived.

The term "homology", as used herein, refers to a degree of complementarity. There may be partial homology (i.e., less than 100% identity) or complete homology (i.e., 100% identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction.

The term "hybridization", as used herein, refers to any process by which a strand of nucleic acid binds with a complementary strand through base pairing.

An "insertion" or "addition", as used herein, refers to a change in an amino acid or nucleotide sequence resulting in the addition of one or more amino acid residues or nucleotides, respectively, as compared to the naturally occurring molecule.

A "methanogen," as used herein, refers to microbes that produce methane gas, which include *Methanobrevibacter, Methanothermobacter, Methanomicrobium, Methanobacterium,* and *Methanosarcina*. Specific methanogens include, but are not limited to, *Methanobrevibacter ruminantium, Methanobrevibacter smithii, Methanobrevibacter acididurans, Methanobrevibacter thaueri, Methanobacterium bryantii, Methanobacterium formicicum, Methanothermobacter* marburgensis, *Methanothermobacter wolfeii*, *Methanosphaera stadtmanae*, *Methanomicrobium mobile*, *Methanosarcina barkeri*, *Methanosarcina mazei*, *Methanococcoides burtonii*, and *Methanolobus taylorii*. The *Methanobrevibacter ruminantium* strain M1$^T$ is publicly available in depositories at the Leibniz Institute DSMZ-German Collection of Microorganisms and Cell Cultures; Braunschweig, Germany (DSM No. DSM1093) and at the American Type Culture Collection (ATCC; Manassas, Va., USA) (ATCC No. 35063). All methanogen genera and species are encompassed by this term.

"Microbial" cells as used herein, refers to naturally-occurring or genetically modified microbial cells including archaebacteria such as methanogens, halophiles, and thermoacidophiles, and eubacteria, such as cyanobacteria, spirochetes, proteobacteria, as well as gram positive and gram negative bacteria.

The term "modified" refers to altered sequences and to sequence fragments, variants, and derivatives, as described herein.

"Nucleic acid sequence" or "nucleotide sequence" as used herein, refers to a sequence of a polynucleotide, oligonucleotide, or fragments thereof, and to DNA or RNA of natural, recombinant, synthetic, or semi-synthetic origin which may be single or double stranded, and can represent the sense or antisense strand, and coding or non-coding regions. The sequences of the invention most preferably include polypeptide coding sequences (e.g., SEQ ID NO:173-341 or 342-533, or complements, or modified sequences thereof) that comprise at least 15, 18, 21, 24, 27, 30, 33, 36, 39, 45, 51, 57, or 66 nucleotides, preferably at least 15 to 30, 15 to 45, 30 to 45, 36 to 45, 45 to 51, 51 to 57, or 51 to 66 nucleotides, or at least 100 nucleotides, or at least 1000 nucleotides. It will be understood that each reference to a "nucleic acid sequence" or "nucleotide sequence" herein, will include the native, full-length sequence (e.g., SEQ ID NO:173-341 or 342-533), as well as any complements, fragments, alterations, derivatives, or variants, thereof.

The term "oligonucleotide" refers to a nucleic acid sequence comprising at least 6, 8, 10, 12, 15, 18, 21, 25, 27, 30, or 36 nucleotides, or at least 12 to 36 nucleotides, or at least 15 to 30 nucleotides (e.g., at least a fragment of SEQ ID NO:173-341 or 342-533, or a complement thereof), which can be used in PCR amplification, sequencing, or hybridization assays. As used herein, oligonucleotide is substantially equivalent to the terms "amplimers," "primers," "oligomers," "oligos," and "probes," as commonly defined in the art.

The term "polynucleotide," when used in the singular or plural, generally refers to any nucleic acid sequence, e.g., any polyribonucleotide or polydeoxyribonucleotide, which may be unmodified RNA or DNA or modified RNA or DNA. This includes, without limitation, single and double stranded DNA, DNA including single and double stranded regions, single and double stranded RNA, and RNA including single and double stranded regions, hybrid molecules comprising DNA and RNA that may be single stranded or, more typically, double stranded or include single and double stranded regions. Also included are triple-stranded regions comprising RNA or DNA or both RNA and DNA. Specifically included are mRNAs, cDNAs, and genomic DNAs, and any fragments thereof. The term includes DNAs, and RNAs that contain one or more modified bases, such as tritiated bases, or unusual bases, such as inosine. The polynucleotides of the invention can encompass coding or non-coding sequences, or sense or antisense sequences, or iRNAs such as siRNAs. It will be understood that each reference to a "polynucleotide" or like term, herein, will include the full length sequences as well as any complements, fragments, alterations, derivatives, or variants thereof.

"Peptide nucleic acid" or "PNA" as used herein, refers to an antisense molecule or anti-gene agent which comprises bases linked via a peptide backbone.

The term "ruminant," as used herein, refers to animals that have a rumen as a special type of digestive organ. Ruminants include, but are not limited to, cattle, sheep, goats, buffalo, moose, antelope, caribou, and deer.

"Signal peptides," as used herein, refers to the isolated peptides of the invention obtained from any species, preferably microbial, from any source whether natural, synthetic, semi-synthetic, or recombinant. Specifically, a signal peptide can be obtained from methanogen cells, such as *Methanobrevibacter* cells, in particular, *M. ruminantium*, or *M. smithii* cells. For recombinant production, a signal peptide of the invention can be obtained from microbial or eukaryotic cells, for example, *Escherichia*, *Streptomyces*, *Bacillus*, *Salmonella*, yeast, insect cells such as *Drosophila*, animal cells such as COS and CHO cells, or plant cells. It will be understood that each reference to a "peptide," herein, will include the full length sequence (e.g., SEQ ID NO:1-172), as well as any alterations, fragments, derivatives, or variants, thereof.

The terms "stringent conditions" or "stringency," as used herein, refer to the conditions for hybridization as defined by the nucleic acid, salt, and temperature. These conditions are well known in the art and may be altered in order to identify or detect identical or related polynucleotide sequences. See, e.g., Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "subject" includes human and non-human animals. Non-human animals include, but are not limited to, birds and mammals, such as ruminants, and in particular, mice, rabbits, cats, dogs, pigs, sheep, goats, cows, and horses.

The terms "substantially purified" or "isolated" as used herein, refer to nucleic or amino acid sequences that are removed from their cellular, recombinant, or synthetic environment, and are at least 60% free, preferably 75% free, and most preferably at least 90% free or at least 99% free from other components with which they are associated in a cellular, recombinant, or synthetic environment.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of a peptide or polypeptide, as used herein, refers to an amino acid sequence that is altered by one or more amino acids. A variant polynucleotide is altered by one or more nucleotides. A variant may result in "conservative" changes, wherein a substituted amino acid has similar structural or chemical properties, e.g., replacement of leucine with isoleucine. More rarely, a variant may result in "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunogenic activity may be found using computer programs well known in the art, for example, LASERGENE software (DNASTAR).

The invention also encompasses variants which retain at least one biological activity (e.g., cell association or cell permeabilisation) or functional activity of the peptide or polypeptide. A preferred variant is one having at least 80%, and more preferably at least 90%, sequence identity to a disclosed sequence. A most preferred variant is one having at least 95%, at least 97%, at least 98%, at least 99%, at least 99.5%, at least 99.8%, or at least 99.9% sequence identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100. A useful alignment program is AlignX (Vector NTI).

DESCRIPTION OF THE INVENTION

Methane is produced in the foregut of ruminants by methanogens which act as terminal reducers of carbon in the rumen system. The multi-step methanogenesis pathway is well elucidated, mainly from the study of non-rumen methanogens, but the adaptations that allow methanogens to grow and persist in the rumen are not well understood. *Methanobrevibacter ruminantium* is a prominent methanogen in New Zealand ruminants. As described herein, the draft genome sequence of *M. ruminantium* shows a size of approximately 3.0 Mb and a GC content of 33.68%. As an important finding, the *M. ruminantium* genome was found to include signal peptide sequences for use in targeting and permeabilising cells. The invention therefore encompasses signal peptides, including those comprising SEQ ID NO:1-172, as well as polypeptides comprising these peptides, and alterations, fragments, variants, and derivatives thereof.

The invention encompasses the use of these peptides or polypeptides for targeting and permeabilising microbial cells, especially methanogen cells. The invention further encompasses the use of the peptides or polypeptides for the inhibition of growth or replication of such cells. The peptides and polypeptides of the present invention may be expressed and used in various assays to determine their biological activity. The peptides and polypeptides may be used for large-scale synthesis and isolation protocols, for example, for commercial production. Such peptides and polypeptides may be used to raise antibodies, to isolate corresponding amino acid sequences, and to quantitatively determine levels of the amino acid sequences.

The polypeptides of the present invention may also be used as compositions, for example, pharmaceutical compositions, and as food supplements, e.g., feed components for ruminants. The peptides and polypeptides of the present invention also have health benefits. For example, in heath-related aspects, inhibitors of methanogens can be used to restore energy to the subject that is normally lost as methane. In particular aspects, slow-release ruminal devices can be used in conjunction with the peptides, polypeptides, and compositions (e.g., pharmaceutical compositions and food supplements) of the invention.

The peptides and polypeptides of the present invention comprise at least one sequence selected from the group consisting of: (a) peptides or polypeptides comprising at least one amino acid sequence selected from the group consisting of SEQ ID NO:1-172, or alterations, fragments, variants, or derivatives thereof; (b) peptides or polypeptides comprising a functional domain (e.g., core conserved region disclosed herein) of at least one amino acid sequence selected from the group consisting of SEQ ID NO:1-172, or alterations, fragments, variants, or derivatives thereof; and (c) peptides or polypeptides comprising at least a specified number of contiguous residues of at least one amino acid sequence selected from the group consisting of SEQ ID NO:1-172, or alterations, fragments, variants, or derivatives thereof. All of these sequences are collectively referred to herein as peptides and polypeptides of the invention. In one embodiment, the invention encompasses an isolated peptide or polypeptide comprising the amino acid sequence of at least one of SEQ ID NO:1-172.

The invention also encompasses polynucleotides that encode at least one signal peptide, including those of SEQ ID NO:1-172, as well as polypeptides comprising these peptides, and alterations, fragments, variants, or derivatives thereof.

The invention encompasses the use of these polynucleotides for preparing expression vectors and host cells for targeting and permeabilising microbial cells, especially methanogen cells. The invention further encompasses the use of the polynucleotides for the inhibition of growth or replication of such cells. The isolated polynucleotides of the present invention also have utility in genome mapping, in physical mapping, and in cloning of genes of more or less related bacteria. Probes designed using the polynucleotides of the present invention may be used to detect the presence and examine the expression patterns of genes in any organism having sufficiently homologous DNA and RNA sequences in their cells, using techniques that are well known in the art, such as slot blot techniques or microarray analysis. Primers designed using the polynucleotides of the present invention may be used for sequencing and PCR amplifications.

The polynucleotides of the present invention may also be used as compositions, for example, pharmaceutical compositions, and as food supplements, e.g., feed components for ruminants. The polynucleotides of the present invention also have health benefits. For such benefits, the polynucleotides can be presented as expression vectors or host cells comprising expression vectors. In particular aspects, slow-release ruminal devices can be used in conjunction with the polynucleotides, vectors, host cells, and compositions (e.g., pharmaceutical compositions and food supplements) of the invention.

The polynucleotides of the present invention comprise at least one sequence selected from the group consisting of: (a) sequences comprising a coding sequence for at least one amino acid sequence selected from the group consisting of SEQ ID NO:1-172, or alterations, fragments, variants, or derivatives thereof; (b) complements, reverse sequences, and reverse complements of a coding sequence for at least one amino acid sequence selected from the group consisting of SEQ ID NO:1-172, or alterations, fragments, variants, or derivatives thereof; (c) open reading frames contained in the coding sequence for at least one amino acid sequence selected from the group consisting of SEQ ID NO:1-172, or their alterations, fragments, variants, or derivatives; (d) functional domains (e.g., core conserved regions disclosed herein) of a coding sequence for at least one amino acid sequence selected from the group consisting of SEQ ID NO:1-172, or alterations, fragments, variants, or derivatives thereof; and (e) sequences comprising at least a specified number of contiguous residues of a coding sequence for at least one amino acid sequence selected from the group consisting of SEQ ID NO:1-172, or alterations, fragments, variants, or derivatives thereof. Oligonucleotide probes and primers are also provided. All of these polynucleotides and oligonucleotide probes and primers are collectively referred to herein, as polynucleotides of the invention. In one embodiment, the invention encompasses an isolated polynucleotide comprising a coding sequence for at least one amino acid sequence selected from the group consisting of SEQ ID NO:1-172.

It will be appreciated by those skilled in the art that as a result of the degeneracy of the genetic code, a multitude of nucleotide sequences encoding the peptides of the invention, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to naturally occurring amino acid sequences, and all such variations are to be considered as being specifically disclosed.

Nucleotide sequences which encode signal peptides or polypeptides, or their modified sequences, are preferably capable of hybridizing to the nucleotide sequence of the naturally occurring sequence under appropriately selected conditions of stringency. However, it may be advantageous to produce nucleotide sequences encoding a peptide or its derivatives possessing a substantially different codon usage. Codons may be selected to increase the rate at which expression of the peptide occurs in a particular prokaryotic or eukaryotic host in accordance with the frequency with which particular codons are utilized by the host. For example, codons can be optimized for expression in E. coli, e.g., as provided by SEQ ID NO:342-533. Other reasons for substantially altering the nucleotide sequence encoding peptides and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode the peptides or polypeptides, or their modified sequences, entirely by synthetic chemistry. After production, the synthetic sequence may be inserted into any of the many available expression vectors and cell systems using reagents that are well known in the art. Moreover, synthetic chemistry may be used to introduce mutations into a sequence encoding a peptide or polypeptide, or any alterations, variants, derivatives, or fragments thereof. Also encompassed by the invention are polynucleotide sequences that are capable of hybridizing to the claimed nucleotide sequences, and in particular, those shown in SEQ ID NO:173-341 or 342-533, or their complements, under various conditions of stringency as taught in Wahl, G. M. and S. L. Berger (1987; Methods Enzymol. 152:399-407) and Kimmel, A. R. (1987; Methods Enzymol. 152:507-511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, Ohio), Taq polymerase (Perkin Elmer), thermostable T7 polymerase Amersham Pharmacia Biotech (Piscataway, N.J.), or combinations of polymerases and proofreading exonucleases such as those found in the ELONGASE Amplification System marketed by Life Technologies (Gaithersburg, Md.). Preferably, the process is automated with machines such as the Hamilton Micro Lab, 2200 (Hamilton, Reno, Nev.), Peltier Thermal Cycler (PTC200; MJ Research, Watertown, Mass.) the ABI Catalyst and 373 and 377 DNA Sequencers (Perkin Elmer), or the Genome Sequencer 20™ (Roche Diagnostics).

The nucleic acid sequences encoding the peptides may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and Sequence NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotides or fragments thereof which encode peptides or polypeptides may be used in recombinant DNA molecules to direct expression of the peptides, polypeptides, or modified sequences thereof, in appropriate host cells. Due to the inherent degeneracy of the genetic code, other DNA sequences which encode substantially the same or a functionally equivalent amino acid sequence may be produced, and these sequences may be used to clone and express signal peptides or polypeptides. The nucleotide sequences of the present invention can be engineered using methods generally known in the art in order to alter amino acid-encoding sequences for a variety of reasons, including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, introduce mutations, and so forth.

In another embodiment of the invention, natural, modified, or recombinant nucleic acid sequences encoding peptides or polypeptides may be ligated to a heterologous sequence to encode a fusion protein. For example, it may be useful to encode a chimeric sequence that can be recognized by a commercially available antibody. A fusion protein may also be engineered to contain a cleavage site located between the peptide or polypeptide of the invention and the heterologous protein sequence, so that the peptide or polypeptide may be cleaved and purified away from the heterologous moiety.

In another embodiment, sequences encoding peptides or polypeptides may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the peptide or polypeptide itself may be produced using chemical methods to synthesize the amino acid sequence, or a fragment thereof. For example, peptide synthesis can be performed using various solid-phase techniques (Roberge, J. Y. et al. (1995) Science 269:202-204; Merrifield J. (1963) J. Am. Chem. Soc. 85:2149-2154) and automated synthesis may be achieved, for example, using the ABI 431A Peptide Synthesizer (Perkin Elmer). Various fragments of peptides or polypeptides may be chemically synthesized separately and combined using chemical methods to produce the full length molecule.

The newly synthesized peptide or polypeptide may be isolated by preparative high performance liquid chromatography (e.g., Creighton, T. (1983) Proteins Structures and Molecular Principles, WH Freeman and Co., New York, N.Y.). The composition of the synthetic peptides or polypeptides may be confirmed by amino acid analysis or sequencing (e.g., the Edman degradation procedure; Creighton, supra). Additionally, the amino acid sequence of the peptide or polypeptide, or any part thereof, may be altered during direct synthesis and/or combined using chemical methods with sequences from other proteins, or any part thereof, to produce a modified molecule.

In order to express a biologically active peptides, the nucleotide sequences encoding the peptide or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding the peptide and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding the peptides of the invention. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. For bacteria, useful plasmids include pET, pRSET, pTrcHis2, and pBAD plasmids from Invitrogen, pET and pCDF plasmids from Novagen, and Director™ plasmids from Sigma-Aldrich. For methanogens, useful plasmids include, but are not limited to pME2001, pMV15, and pMP1. In particular, *Escherichia coli* can be used with the expression vector pET. The invention is not limited by the expression vector or host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector.

In bacterial systems, a number of expression vectors may be selected depending upon the use intended for the peptide. For example, when large quantities of peptide are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding a peptide may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503-5509); and the like.

pGEX vectors (Promega, Madison, Wis.) may also be used to express foreign peptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor Xa protease cleavage sites so that the cloned peptide of interest can be released from the GST moiety at will. In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

Specific initiation signals may also be used to achieve more efficient translation of sequences encoding the peptides of the invention. Such signals include the ATG initiation codon and adjacent sequences. In cases where sequences encoding a peptide, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed peptide or polypeptide in the desired fashion. Such modifications of the sequence include, but are not limited to, acetylation, carboxylation, glycosylation, phosphorylation, lipidation, and acylation. Post-translational processing which cleaves a "prepro" form, of the peptide or polypeptide may also be used to facilitate correct insertion, folding, and/or function. Different host cells which have specific cellular machinery and characteristic mechanisms for post-translational activities are available from the American Type Culture Collection (ATCC; Bethesda, Md.) and may be chosen to ensure the correct modification and processing of the sequence. Specific host cells include, but are not limited to, methanogen cells, such as *Methanobrevibacter* cells, in particular, *M. ruminantium*, or *M. smithii* cells. Host cells of interest include, for example, *Rhodotorula, Aureobasidium, Saccharomyces, Sporobolomyces, Pseudomonas, Erwinia* and *Flavobacterium*; or such other organisms as *Escherichia, Lactobacillus, Bacillus, Streptomyces*, and the like. Specific host cells include *Escherichia coli*, which is particularly suited for use with the present invention, *Saccharomyces cerevisiae, Bacillus thuringiensis, Bacillus subtilis, Streptomyces lividans*, and the like.

There are several techniques for introducing nucleic acids into eukaryotic cells cultured in vitro. These include chemical methods (Feigner et al., Proc. Natl. Acad. Sci., USA, 84:7413 7417 (1987); Bothwell et al., Methods for Cloning and Analysis of Eukaryotic Genes, Eds., Jones and Bartlett Publishers Inc., Boston, Mass. (1990), Ausubel et al., Short. Protocols in Molecular Biology, John Wiley and Sons, New York, N.Y. (1992); and Farhood, Annal. NY Acad. Sci., 716:23 34 (1994)), use of protoplasts (Bothwell, supra) or electrical pulses (Vatteroni et al., Mutn. Res: 291:163 169 (1993); Sabelnikov, Prog. Biophys. Mol. Biol., 62: 119 152 (1994); Bothwell et al., supra; and Ausubel et al., supra), use of attenuated viruses (Davis et al., J. Virol. 1996, 70(6), 3781 3787; Brinster et al. J. Gen. Virol. 2002, 83(Pt 2), 369 381; Moss, Dev. Biol. Stan., 82:55 63 (1994); and Bothwell et al., supra), as well as physical methods (Fynan et al., supra; Johnston et al., Meth. Cell Biol., 43(Pt A):353 365 (1994); Bothwell et al., supra; and Ausubel et al., supra).

Successful delivery of nucleic acids to animal tissue can be achieved by cationic liposomes (Watanabe et al., Mol. Reprod. Dev., 38:268 274 (1994)), direct injection of naked DNA or RNA into animal muscle tissue (Robinson et al., Vacc., 11:957 960 (1993); Hoffman et al., Vacc. 12:1529 1533; (1994); Xiang et al., Virol., 199:132 140 (1994); Webster et al., Vacc., 12:1495 1498 (1994); Davis et al., Vacc., 12:1503 1509 (1994); Davis et al., Hum. Molec. Gen., 2:1847 1851 (1993); Dalemans et al. Ann NY Acad. Sci. 1995, 772, 255 256. Conry, et al. Cancer Res. 1995, 55(7), 1397-1400), and embryos (Naito et al., Mol. Reprod. Dev., 39:153 161 (1994); and Burdon et al., Mol. Reprod. Dev., 33:436 442 (1992)), intramuscular injection of self replicating RNA vaccines (Davis et al., J-Virol 1996, 70(6), 3781 3787; Balasuriya et al. Vaccine 2002, 20(11 12), 1609 1617) or intradermal injection of DNA using "gene gun" technology (Johnston et al., supra).

A variety of protocols for detecting and measuring the expression of the peptides or polypeptides of the invention, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay can be used with monoclonal antibodies reactive to two non-interfering epitopes on the peptide or polypeptide, but a competitive binding assay can also be used. These and other assays are described, among other places, in Hampton, R. et al. (1990; Serological Methods, a laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences encoding the peptide, or any polypeptides comprising this peptide, or any modified sequences thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and US Biochemical. Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Expression vectors or host cells transformed with expression vectors may be cultured under conditions suitable for the expression and recovery of the peptide or polypeptide from culture. The culture can comprise components for in vitro or in vivo expression. In vitro expression components include those for rabbit reticulocyte lysates, *E. coli* lysates, and wheat germ extracts, for example, Expressway™ or RiPs systems from Invitrogen, Genelator™ systems from iNtRON Biotechnology, EcoPro™ or STP3™ systems from Novagen, TNT® Quick Coupled systems from Promega, and EasyXpress systems from QIAGEN. The peptide or polypeptide produced from culture may be secreted or contained intracellularly depending on the sequence and/or the vector used. As will be understood by those of skill in the art, expression vectors which encode the peptides or polypeptide are preferably designed to contain signal-sequences which direct secretion of the peptide through a prokaryotic or eukaryotic cell membrane.

Other constructions may include an amino acid domain which will facilitate purification of the peptide or polypeptide. Such domains include, but are not limited to, metal chelating peptides such as histidine-tryptophan (e.g., 6X-HIS (SEQ ID. NO: 514) modules that allow purification on immobilized metals, protein A domains that allow purification on immobilized immunoglobulin, and the domain utilized in the FLAG® extension/affinity purification system (Immunex Corp., Seattle, Wash.). Useful epitope tags include 3XFLAG®, HA, VSV-G, V5, HSV, GST, GFP, MBP, GAL4, and β-galactosidase. Useful plasmids include those comprising a biotin tag (e.g., PinPoint™ plasmids from Promega), calmodulin binding protein (e.g., pCAL plasmids from Stratagene), streptavidin binding peptide (e.g., InterPlay™ plasmids from Stratagene), a c-myc or FLAG® tag (e.g., Immunoprecipitation plasmids from Sigma-Aldrich), or a histidine tag (e.g., QIAExpress plasmids from QIAGEN).

To facilitate purification, a cleavable linker sequence can be used, such as those specific for Factor Xa or enterokinase (Invitrogen, San Diego, Calif.). For example, the vector can include one or more linkers between the purification domain and the peptide or polypeptide. In one aspect, the expression vector can provide for expression of a fusion protein comprising the peptide or polypeptide of the invention and a nucleic acid encoding 6 histidine residues (SEQ ID NO: 514) preceding a thioredoxin or an enterokinase cleavage site. The histidine residues facilitate purification on IMAC (immobilized metal ion affinity chromatography as described in Porath, J. et al. (1992) Prot. Exp. Purif. 3: 263-281) while the enterokinase cleavage site provides a means for purifying the peptide or polypeptide from the fusion protein. A discussion of vectors which contain fusion proteins is provided in Kroll, D. J. et al. (1993; DNA Cell Biol. 12:441-453).

Antibodies of the invention may be produced using methods which are generally known in the art, for example, for use in purification or diagnostic techniques. In particular, purified peptides, polypeptides, or polynucleotides may be used to produce antibodies in accordance with generally known protocols. Such antibodies may include, but are not limited to, polyclonal, monoclonal, chimeric, and single chain antibodies, Fab fragments, and fragments produced by a Fab expression library. Neutralizing antibodies, (i.e., those which inhibit function) are especially preferred for use with the invention.

For the production of antibodies, various hosts including goats, rabbits, rats, mice, humans, and others, may be immunized by injection with a peptide, polypeptide, polynucleotide, or any fragment thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, polypeptides, or fragments used to induce antibodies have an amino acid sequence comprising at least five amino acids and more preferably at least 10 amino acids. It is also preferable that they are identical to a portion of the amino acid sequence of the natural protein, and they may contain the entire amino acid sequence of a small, naturally occurring molecule. Short stretches of amino acids may be fused with those of another protein such as keyhole limpet hemocyanin and antibody produced against the chimeric molecule.

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell. Biol. 62:109-120). Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

In addition, techniques can be used for the production of "chimeric antibodies", e.g., the combining of antibody genes to obtain a molecule with appropriate antigen specificity and biological activity (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce specific single chain antibodies.

Antibodies with related specificity, but of distinct idiotypic composition, may be generated by chain shuffling from random combinatorial immunoglobin libraries (Burton D. R. (1991) Proc. Natl. Acad. Sci. 88:11120-3).

Those of skill in the art to which the invention relates will appreciate the terms "diabodies" and "triabodies". These are molecules which comprise a heavy chain variable domain (VH) connected to a light chain variable domain (VL) by a short peptide linker that is too short to allow pairing between the two domains on the same chain. This promotes pairing with the complementary domains of one or more other chains and encourages the formation of dimeric or trimeric molecules with two or more functional antigen binding sites. The resulting antibody molecules may be monospecific or multispecific (e.g., bispecific in the case of diabodies). Such antibody molecules may be created from two or more antibodies using methodology standard in the art to which the invention relates; for example, as described by Todorovska et al. (Design and application of diabodies, triabodies and tetrabodies for cancer targeting. J. Immunol. Methods. 2001 Feb. 1; 248 (1-2):47-66).

Antibody fragments which contain specific binding sites may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse, W. D. et al. (1989) Science 254: 1275-1281).

Various immunoassays may be used for screening to identify antibodies having binding specificity. Numerous protocols for competitive binding or immunoradiometric assays using either polyclonal or monoclonal antibodies with established specificities are well known in the art. Such immunoassays typically involve the measurement of complex formation between a peptide, polypeptide, or polynucleotide and its specific antibody. A two-site, monoclonal-based immunoassay utilizing monoclonal antibodies reactive to two non-interfering epitopes is preferred, but a competitive binding assay may also be employed (Maddox, supra).

The signal peptides described herein have the ability to enter cells and are therefore useful as carrier molecules for the delivery of inhibitory molecules into microbial cells. The chemistry for coupling compounds to amino acids is well developed and a number of different molecule types could be linked to the signal peptide. The most common coupling methods rely on the presence of free amino (alpha-amino or Lys), sufhydryl (Cys), or carboxylic acid groups (Asp, Glu, or alpha-carboxyl). Coupling methods can be used to link the peptide to the cell inhibitor via the carboxy- or amino-terminal residue. In some cases, a sequence includes multiple residues that may react with the chosen chemistry. This can be used to produce multimers, comprising more than one cell inhibitor. Alternatively, the peptide or polypeptide can be shortened or chosen so that reactive residues are localized at either the amino or the carboxyl terminus of the sequence.

For example, a reporter molecule such as fluorescein can be specifically incorporated at a lysine residue (Ono et al., 1997) using N-α-Fmoc-Nε-1-(4,4-dimethyl-2,6 dioxocyclohex-1-ylidene-3-methylbutyl)-L-lysine during peptide synthesis. Following synthesis, 5- and 6-carboxyfluorescein succinimidyl esters can be coupled after 4,4-dimethyl-2,6 dioxocyclohex-1-ylidene is removed by treatment with hydrazine. Therefore coupling of an inhibitory molecule to the signal peptide or polypeptide can be accomplished by inclusion of a lysine residue to the permeabilising sequence, then reaction with a suitably derivatised cell inhibitor.

EDC (1-ethyl-3-(3-dimethylaminopropyl) carbodiimide hydrochloride) or the carbodiimide coupling method can also be used. Carbodiimides can activate the side chain carboxylic groups of aspartic and glutamic acid as well as the carboxyl-terminal group to make them reactive sites for coupling with primary amines. The activated peptides are mixed with the cell inhibitor to produce the final conjugate. If the cell inhibitor is activated first, the EDC method will couple the cell inhibitor through the N-terminal alpha amine and possibly through the amine in the side-chain of Lys, if present in the sequence.

m-Maleimidobenzoyl-N-hydroxysuccinimide ester (MBS) is a heterobifunctional reagent that can be used to link peptides to cell inhibitors via cysteines. The coupling takes place with the thiol group of cysteine residues. If the chosen sequence does not contain Cys it is common to place a Cys residue at the N- or C-terminus to obtain highly controlled linking of the peptide to the cell inhibitor. For synthesis purposes, it may be helpful for the cysteine to be placed at the N-terminus of the peptide. MBS is particularly suited for use with the present invention.

Glutaraldehyde can be used as a bifunctional coupling reagent that links two compounds through their amino groups. Glutaraldehyde provides a highly flexible spacer between the peptide and cell inhibitor for favorable presentation. Glutaraldehyde is a very reactive compound and will react with Cys, Tyr, and His to a limited extent. The glutaraldehyde coupling method is particularly useful when a peptide contains only a single free amino group at its amino terminus. If the peptide contains more than one free amino group, large multimeric complexes can be formed.

In one aspect, the peptides or polypeptides of the invention can be fused (e.g., by in-frame cloning) or linked (e.g., by chemical coupling) to cell inhibitors such as antimicrobial agents. Included among these are antimicrobial peptides, for example, bactericidal/permeability-increasing protein, cationic antimicrobial proteins, lysozymes, lactoferrins, and cathelicidins (e.g., from neutrophils; see, e.g., Hancock and Chapple, 1999, Antimicrob. Agents Chemother. 43:1317-1323; Ganz and Lehrer, 1997, Curr. Opin. Hematol. 4:53-58; Hancock et al., 1995, Adv. Microb. Physiol. 37:135-175). Antimicrobial peptides further include defensins (e.g., from epithelial cells or neutrophils) and platelet microbiocidal proteins (see, e.g., Hancock and Chapple, 1999, Antimicrob. Agents Chemother 43:1317-1323). Additional antimicrobial peptides include, but are not limited to, gramicidin S, bacitracin, polymyxin B, tachyplesin, bactenecin (e.g., cattle bactenecin), ranalexin, cecropin A, indolicidin (e.g., cattle indolicidin), and nisin (e.g., bacterial nisin).

Also included as antimicrobial agents are ionophores, which facilitate transmission of an ion, (such as sodium), across a lipid barrier such as a cell membrane. Two ionophore compounds particularly suited to this invention are the RUMENSIN™ (Eli Lilly) and Lasalocid (Hoffman LaRoche). Other ionophores include, but are not limited to, salinomycin, avoparcin, aridcin, and actaplanin. Other antimicrobial agents include Monensin™ and azithromycin, metronidazole, streptomycin, kanamycin, and penicillin, as well as, generally, β-lactams, aminoglycosides, macrolides, chloramphenicol, novobiocin, rifampin, and fluoroquinolones (see, e.g., Horn et al., 2003, Applied Environ. Microbiol. 69:74-83; Eckburg et al., 2003, Infection Immunity 71:591-596; Gijzen et al., 1991, Applied Environ. Microbiol. 57:1630-1634; Bonelo et al., 1984, FEMS Microbiol. Lett. 21:341-345; Huser et al., 1982, Arch. Microbiol. 132:1-9; Hilpert et al., 1981, Zentbl. Bakteriol. Mikrobiol. Hyg. 1 Abt Orig. C 2:21-31).

Particularly useful inhibitors are compounds that block or interfere with methanogenesis, including bromoethanesulphonic acid, e.g., 2-bromoethanesulphonic acid (BES) or a salt thereof, for example, a sodium salt. Sodium molybdate (Mo) is an inhibitor of sulfate reduction, and can be used with bromoethanesulphonic acid. Other anti-methanogenesis compounds include, but are not limited to, nitrate, formate, methyl fluoride, chloroform, chloral hydrate, sodium sulphite, ethylene and unsaturated hydrocarbons, acetylene, fatty acids such as linoleic and cis-oleic acid, saturated fatty acids such as behenic and stearic acid, and, also lumazine (e.g., 2,4-pteridinedione). Additional compounds include 3-bromopropanesulphonate (BPS), propynoic acid, and ethyl 2-butynoate.

Further included as antimicrobial agents are lytic enzymes, including lysozyme, endolysin, lysozyme, lysin, phage lysin, muralysin, muramidase, and virolysin. Useful enzymes exhibit the ability to hydrolyse specific bonds in the bacterial cell wall. Particular lytic enzymes include, but are not limited to, glucosaminidases, which hydrolyse the glycosidic bonds between the amino sugars (e.g., N-acetylmuramic acid and N-acetylglucosamine) of the peptidoglycan, amidases, which cleave the N-acetylmuramoyl-L-alanine amide linkage between the glycan strand and the cross-linking peptide, and endopeptidases, which hydrolyse the interpeptide linkage (e.g., cysteine endopeptidases) and endoisopeptidases that attack pseudomurein of methanogens from the family Methanobacteriaceae.

Additionally, PNAs are included as antimicrobial agents. PNAs are peptide-nucleic acid hybrids in which the phosphate backbone has been replaced by an achiral and neutral backbone made from N-(2-aminoethyl)-glycine units (see, e.g., Eurekah Bioscience Collection. PNA and Oligonucleotide Inhibitors of Human Telomerase. G. Gavory and S. Balasubramanian, Landes Bioscience, 2003). The bases A, G, T, C are attached to the amino nitrogen on the backbone via methylenecarbonyl linkages (P. E. Nielsen et al., Science 1991. 254: 1497-1500; M. Egholm et al., Nature 1993. 365: 566-568). PNAs bind complementary sequences with high specificity, and higher affinity relative to analogous DNA or RNA (M. Egholm et al., supra). PNA/DNA or PNA/RNA hybrids also exhibit higher thermal stability compared to the corresponding DNA/DNA or DNA/RNA duplexes (M. Egholm et al., supra). PNAs also possess high chemical and biological stability, due to the unnatural amide backbone that is not recognized by nucleases or proteases (V. Demidov et al., Biochem Pharmacol 1994. 48: 1310-1313). Typically, PNAs are at least 5 bases in length, and include a terminal lysine. PNAs may be pegylated to further extend their lifespan (Nielsen, P. E. et al. (1993) Anticancer Drug Des. 8:53-63).

In one particular aspect, the peptides or polypeptides of the invention can be fused (e.g., by in-frame cloning) or linked (e.g., by chemical coupling) to cell inhibitors such as antibodies or fragments thereof. The antibodies or antibody fragments can be directed to microbial cells, or particularly methanogen cells, or one or more cell components. For example, cell surface proteins, e.g., receptors can be targeted. Included are immunoglobulin molecules and immunologically active portions of immunoglobulin (Ig) molecules, i.e., molecules that contain an antigen binding site that specifically binds (immunoreacts with) an antigen.

The peptides or polypeptides of the invention find particular use in targeting a microbial cell, in particular, a methanogen cell. In certain aspects, the peptides and polypeptides can be used to bind to the cell wall or membrane and/or permeabilise the cell. As such, the peptides or polypeptides can be used for transient or extended attachment to the cell, or to penetrate the cell wall or membrane and/or accumulate in the intracellular environment. It is understood that the peptides, polypeptides, as well as the corresponding polynucleotides, expression vectors, host cells, and antibodies of the invention, can be used to target various microbes, for example, *Methanobrevibacter ruminantium*, which is a common methanogen in ruminants, and *Methanobrevibacter smithii*, which is a common methanogen in humans. To effect targeting, the microbial cell can be contacted with the signal peptide or polypeptide comprising the peptide, as isolated from one or more natural sources, or produced by expression vectors and/or host cells, or synthetic or semi-synthetic chemistry as described in detail herein. In particular aspects, the peptide or polypeptide is delivered to subjects as composition described in detail herein, for example, through use of a slow-release device for ruminants.

In certain embodiments, the polypeptide is fused or linked to a cell inhibitor, for example, an anti-methanogenesis compound (e.g., bromoethanesulphonic acid), an antibody or antibody fragment, lytic enzyme, peptide nucleic acid, antimicrobial peptide, or other antibiotic. The peptide-inhibitor or polypeptide-inhibitor is delivered to subjects as a composition to inhibit growth or replication of microbial cells, in particular, methanogen cells. The composition comprises, for example: a) an isolated signal peptide or polypeptide comprising this peptide, or an alteration, fragment, variant, or derivative thereof; b) an isolated polynucleotide, or an alteration, fragment, variant, or derivative thereof; c) an expression vector comprising this polynucleotide; or d) a host cell comprising this expression vector. The compositions of the invention can be specifically packaged as part of kits for targeting, permeabilising, and/or inhibiting microbial cells, especially methanogen cells, in accordance with the disclosed methods. The kits comprise at least one composition as set out herein and instructions for use in permeabilising cells or inhibiting cell growth or replication for methanogens or other microbes.

As an additional embodiment, the invention relates to a pharmaceutical composition in conjunction with a pharmaceutically acceptable carrier, for use with any of the methods discussed above. Such pharmaceutical compositions may comprise a signal peptide or polypeptide comprising this peptide, in combination with a cell inhibitor. Alternatively, the pharmaceutical compositions may comprise an expression vector or host cell as described in detail herein. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a subject alone, or in combination with other agents, drugs (e.g., antimicrobial drugs), or hormones.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.). The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilising agents may be added, such as the cross-linked polyvinyl pyrrolidone, agar, alginic acid, or a salt thereof, such as sodium alginate.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use. After pharmaceutical compositions have been prepared, they can be placed in an appropriate container and labeled for treatment of an indicated condition. For administration of a composition of the invention, such labeling would include amount, frequency, and method of administration.

Pharmaceutical compositions suitable for use in the invention include compositions wherein the active ingredients are contained in an effective amount to achieve the intended purpose. For any compound, the therapeutically effective dose can be estimated initially either in cell assays, e.g., in microbial cells, or in particular, in methanogen cells, or in animal models, usually mice, rabbits, dogs, or pigs, or in ruminant species such as sheep, cattle, deer, and goats. The animal model may also be used to determine the appropriate concentration range and route of administration. Such information can then be used to determine useful doses and routes for administration in a subject. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for polynucleotides than for peptides or polypeptides. Similarly, delivery of polynucleotides or polypeptides will be specific to particular cells, conditions, locations, etc.

Peptide- and polypeptide-based therapeutics are widely-known, and methods of manufacture of such compositions are well-established in the art. Exemplary peptide and polypeptide therapeutics and their manufacture are described, for example, for denileukin difitox, octreotide, vapreotide, lanreotide, RC-3940 series peptides, decapeptyl, lupron, zoladex, cetrorelix (see, e.g., Lu et al., 2006, AAPS J 8:E466-472), hemocidins, staphopains (see, e.g., Dubin et al., 2005, Acta Biochemica Polonica, 52:633-638), as well as indolicidin, defensins, lantibiotics, microcidin B17, histatins, and maganin (see, e.g., Yeaman and Yount, 2003, Pharmacol Rev 55:27-55). General guidance for peptide and polypeptide therapeutics can also be found in Degim et al., 2007, Curr Pharm Des 13:99-117 and Shai et al., 2006, Curr Prot Pept Sci, 7:479-486. Recently approved peptide-based drugs include Hematide™ (synthetic peptide-based erythropoiesis-stimulating agent, Affymax, Inc.), Exenatide (synthetic exendin-4, Amylin/Eli Lilly), Natrecor (nesiritide, natriuretic peptide, Scios), Plenaxis (abarelix, Praecis Pharmaceuticals), and SecreFlo (secretin, Repligen).

The exact dosage will be determined by the practitioner, in light of factors related to the subject that requires treatment. Dosage and administration are adjusted to provide sufficient levels of the active agent or to maintain the desired effect. Factors which may be taken into account include the severity of the disease state, general health of the subject, age, weight, and gender of the subject, diet, time, and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Particularly useful for the compositions of the invention (e.g., pharmaceutical compositions) are slow release formulas or mechanisms. For example, intra-ruminal devices include, but are not limited to, Time Capsule™ Bolus range by Agri-Feeds Ltd., New Zealand, originally developed within AgResearch Ltd., New Zealand, as disclosed in WO 95/19763 and NZ 278977, and CAPTEC by Nufarm Health & Sciences, a division of Nufarm Ltd., Auckland, New Zealand, as disclosed in AU 35908178, PCT/AU81/100082, and Laby et al., 1984, Can. J. Anim. Sci. 64 (Suppl.), 337-8, all of which are incorporated by reference herein. As a particular example, the device can include a spring and plunger which force the composition against a hole in the end of a barrel.

As a further embodiment, the invention relates to a composition for a water supplement, e.g., drenching composition, or food supplement, e.g., ruminant feed component, for use with any of the methods discussed above. In particular aspects, the food supplement comprises at least one vegetable material that is edible, and a peptide or polypeptide of the invention. Alternatively, the food supplement comprises at least one vegetable material that is edible, and a polypetide or peptide, or a polynucleotide encoding a peptide or polypeptide disclosed herein, for example, as an expression vector or host cell comprising the expression vector. In particular, the composition further includes a cell inhibitor, as fused or linked to the resultant sequence. The preferred vegetable material include any one of hay, grass, grain, or meal, for example, legume hay, grass hay, corn silage, grass silage, legume silage, corn grain, oats, barley, distillers grain, brewers grain, soy bean meal, and cotton seed meal. In particular, grass silage is useful as a food composition for ruminants. The plant material can be genetically modified to contain one or more components of the invention, e.g., one or more polypeptides or peptides, polynucleotides, or vectors.

In another embodiment, antibodies which specifically bind the peptides, polypeptides, or polynucleotides of the invention may be used to determine the presence of microbes, especially methanogens, or in assays to monitor levels of such microbes. The antibodies useful for diagnostic purposes may be prepared in the same manner as those described above. Diagnostic assays include methods which utilize the antibody and a label to detect a peptide or polypeptide in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols for measuring levels of a peptide, polypeptide, or polynucleotide are known in the art (e.g., ELISA, RIA, FACS, and blots), and provide a basis for determining the presence or levels of a microbe, especially a methanogen. Normal or standard levels established by combining body fluids or cell extracts taken from normal subjects, e.g., normal humans or ruminants, with the antibody under conditions suitable for complex formation. The amount of standard complex formation may be quantified by various methods, but preferably by photometric means. Quantities of peptide, polypeptide, or polynucleotide expressed in subject, control, and treated samples (e.g., samples from treated subjects) are compared with the standard values. Deviation between standard and subject values establishes the parameters for determining the presence or levels of the microbe.

In a particular embodiment of the invention, the polynucleotides may be used for diagnostic purposes using particular hybridization and/or amplification techniques. The polynucleotides which may be used include oligonucleotides, complementary RNA and DNA molecules, and PNAs. The polynucleotides may be used to detect and quantitate gene expression in samples in which expression may be correlated with the presence or levels of a microbe. The diagnostic assay may be used to distinguish between the absence, presence, and alteration of microbe levels, and to monitor levels during therapeutic intervention.

In one aspect, hybridization with PCR probes may be used to identify nucleic acid sequences, especially genomic sequences, which encode the peptides or polypeptides of the invention. The specificity of the probe, whether it is made from a highly specific region, e.g., 10 unique nucleotides in the 5' regulatory region, or a less specific region, e.g., in the 3' coding region, and the stringency of the hybridization or amplification (maximal, high, intermediate, or low) will determine whether the probe identifies only naturally occurring sequences, alleles, or related sequences. Probes may also be used for the detection of related sequences, and should preferably contain at least 50% of the nucleotides from any of the coding sequences. The hybridization probes of the subject invention may be DNA or RNA and derived from the nucleotide sequence of SEQ ID NO:173-341 or 342-533, or complements, or modified sequences thereof, or from genomic sequences including promoter, enhancer elements, and introns of the naturally occurring sequence.

Means for producing specific hybridization probes for DNAs include the cloning of nucleic acid sequences into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}$P or $^{35}$S, or enzymatic labels, such as alkaline phosphatase coupled to the probe via avidin/biotin coupling systems, and the like. The polynucleotides may be used in Southern or northern analysis, dot blot, or other membrane-based technologies; in PCR technologies; or in dipstick, pin, ELISA assays, or microarrays utilizing fluids or tissues from subject biopsies to detect the presence or levels of a microbe. Such qualitative or quantitative methods are well known in the art.

In a particular aspect, the nucleic acid sequences may be useful in various assays labelled by standard methods, and added to a fluid or tissue sample from a subject under conditions suitable for hybridization and/or amplification. After a suitable incubation period, the sample is washed and the signal is quantitated and compared with a standard value. If the amount of signal in the test sample is significantly altered from that of a comparable control sample, the presence of altered levels of nucleotide sequences in the sample indicates the presence or levels of the microbe. Such assays may also be used to evaluate the efficacy of a particular treatment regimen in animal studies, in clinical trials, or in monitoring the treatment of a subject.

In order to provide a basis for the diagnosis of the presence or levels of a microbe, a normal or standard profile for expression is established. This may be accomplished by combining body fluids or cell extracts taken from normal subjects, with a polynucleotide or a fragment thereof, under conditions suitable for hybridization and/or amplification. Standard levels may be quantified by comparing the values obtained from normal subjects with those from an experiment where a known amount of a substantially purified polynucleotide is used. Standard values obtained from normal samples may be compared with values obtained from samples from subjects treated for microbial growth. Deviation between standard and subject values is used to establish the presence or levels of the microbe.

Once the microbe is identified and a treatment protocol is initiated, hybridization and/or amplification assays may be repeated on a regular basis to evaluate whether the level of expression in the subject begins to decrease relative to that which is observed in the normal subject. The results obtained from successive assays may be used to show the efficacy of treatment over a period ranging from several days to months.

Particular diagnostic uses for oligonucleotides designed from the nucleic acid sequences may involve the use of PCR. Such oligomers may be chemically synthesized, generated enzymatically, or produced in vitro. Oligomers will preferably consist of two nucleotide sequences, one with sense orientation (5'.fwdarw.3') and another with antisense orientation (3'.fwdarw.5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate expression include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 229-236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotides described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents. In one embodiment, the microarray is prepared and used according to methods known in the art such as those described in PCT application WO 95/11995 (Chee et al.), Lockhart, D. J. et al. (1996; Nat. Biotech. 14: 1675-1680) and Schena, M. et al. (1996; Proc. Natl. Acad. Sci. 93: 10614-10619).

In one aspect, the oligonucleotides may be synthesized on the surface of the microarray using a chemical coupling procedure and an ink jet application apparatus, such as that described in PCT application WO95/251116 (Baldeschweiler et al.). In another aspect, a "gridded" array analogous to a dot or slot blot (HYBRIDOT apparatus, Life Technologies) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including multichannel pipettors or robotic instruments; Brinkmann, Westbury, N.Y.) and may contain 8, 24, 96, 384, 1536 or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs are appropriate probes. Therefore, in one aspect, mRNA is used to produce cDNA which, in turn and in the presence of fluorescent nucleotides, is used to produce fragments or antisense RNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and oligolabeling kits (Amersham Pharmacia Biotech) well known in the area of hybridization technology.

In another embodiment of the invention, the peptides or polypeptides of the invention or functional or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the peptide or polypeptide and the agent being tested, may be measured.

One technique for drug screening which may be used provides for high throughput screening of compounds having suitable binding affinity to the peptide or polypeptide of interest as described in published PCT application WO 84/03564. In this method, large numbers of different small test compounds are synthesized on a solid substrate, such as plastic pins or some other surface. The test compounds are reacted with the peptide or polypeptide, or fragments thereof, and washed. Bound peptide or polypeptide is then detected by methods well known in the art. Purified peptide or polypeptide can also be coated directly onto plates for use in the aforementioned drug screening techniques. Alternatively, non-neutralizing antibodies can be used to capture the peptide and immobilize it on a solid support.

In another technique, one may use competitive drug screening assays in which neutralizing antibodies capable of binding the peptide or polypeptide specifically compete with a test compound for binding to the peptide or polypeptide. In this manner, the antibodies can be used to detect the presence of a test compound which shares one or more antigen binding sites with the antibody.

EXAMPLES

The examples described herein are for purposes of illustrating embodiments of the invention. Other embodiments, methods, and types of analyses are within the scope of persons of ordinary skill in the molecular diagnostic arts and need not be described in detail hereon. Other embodiments within the scope of the art are considered to be part of this invention.

Example 1

Materials and Methods

Genome Size Estimation

*Methanobrevibacter ruminantium* strain M1$^T$ (DSM1093) was grown on BY+ medium (basal medium, Joblin et al., 1990) which consists of [g/l] NaCl (1), $KH_2PO_4$ (0.5), $(NH_4)_2SO_4$ (0.25), $CaCL_2.2H_2O$ (0.13), $MgSO_4.7H_2O$ (0.2), $K_2HPO_4$ (1), clarified rumen fluid (300 ml) $dH_2O$ (360 ml), $NaHCO_3$ (5), resazurin (0.2 ml) L-cysteine-HCl (0.5), yeast extract (2), and Balch's trace elements solution (10 ml) (added trace elements; Balch et al., 1979) which consists of (g/l) nitrilotriacetic acid (1.5), $MgSO_4.7H_2O$ (3), $MnSO_4.H_2O$ (0.5), NaCl (1), $FeSO_4.7H_2O$ (0.1), $CoCl_2.6H_2O$ (0.1), $CaCl_2$ (0.1), $ZnSO_4.7H_2O$ (0.1), $CuSO_4.5H_2O$ (0.01), $AlK(SO_4)_2.12H_2O$ (0.01), $H_3BO_3$ (0.01), $Na_2MoO_4.2H_2O$ (0.01), $NiSO_4.6H_2O$ (0.03), $Na_2SeO_3$ (0.02), and $Na_2Wo_4.2H_2O$ (0.02). Genomic DNA was extracted using a freeze-grinding method. Cells were harvested by centrifugation, and the cell pellet was placed in a pre-chilled mortar, frozen with liquid nitrogen, and gently ground to a fine powder using a pre-chilled, sterilised mortar and pestle. Cell homogenates were imbedded in agarose plugs and subsequent manipulations were carried out in the plugs to reduce the physical shearing of genomic DNA. Digests were performed with restriction endonucleases and DNA fragments were separated using pulsed-field gel electrophoresis (PFGE).

DNA Cloning and Sequencing

The DNA of the *M. ruminantium* genome was sequenced by Agencourt Biosciences Corporation (Massachusetts, USA) using a random shotgun cloning approach (Fleischmann et al., 1995) and by Macrogen Corporation (Rockville, Md., USA) using pyrosequencing. Libraries of *M. ruminantium* DNA were constructed in *Escherichia coli* by random physical disruption of genomic DNA and separation of fragments by gel electrophoresis. Large fragments in the 40 Kb range were retrieved from the gel and used to generate a large insert fosmid library. DNA fragments in the 2 to 4 Kb range were recovered and used to generate a small insert plasmid library. Clones resulting from both large and small insert libraries were grown, their fosmid or plasmid DNA recovered and sequenced using high throughput sequencing technology. Sufficient clones were sequenced to give, theoretically, 8 fold coverage of the *M. ruminantium* genome. Pyrosequencing was performed on randomly sheared genomic DNA fragments to give a final theoretical 10 fold coverage.

Sequence Assembly and Analysis

DNA sequences were aligned to find sequence overlaps and assembled into contiguous (contig) sequences using Paracel Genome Assembler (Paracel Inc, CA, USA) and the Staden package (Staden et al., 1998) in combination with sequence from both standard and inverse PCRs. Contigs were analysed using the open reading frame (ORF) finder GLIMMER (Gene Locator Interpolated Markov Model ER Salzberg et al., 1998) and each ORF was analysed by BLAST (Basic Local Alignment Search Tool (Altschul et al., 1997) against the National Center for Biotechnology Information (NCBI) non-redundant nucleotide and protein databases.

The contigs from the 8 fold draft phase sequence were joined at random by artificial linking of sequences to generate a "pseudomolecule" and submitted to The Institute for Genomic Research (TIGR, DC, USA) for autoannotation. The contigs assembled from the 10 fold pyrosequencing were reanalysed using GLIMMER and ORFs were autoannotated using GAMOLA (Global Annotation of Multiplexed On-site Blasted DNA sequences; Alternann and Klaenhammer, 2003). Automated annotations were subsequently verified manually. ORFs were categorised by function using the clusters of orthologous proteins (COG) database (threshold 1 e-02) (Tatusov et al., 2001).

Protein motifs were determined by HMMER (hypertext transfer protocol://hmmer.wustl.edu) using PFAM HMM and TIGRFAM libraries, with global and local alignment (hypertext transfer protocol://pfam.wustl.edu) and standard and fragment-mode TIGRFAM HMMs models (hypertext transfer protocol://www.tigr.org/TIGRFAMs) respectively (threshold 1 e-02). tRNAs were identified by using TRNASCAN-SE (Lowe and Eddy, 1997) and nucleotide repeats were identified using the KODON software package (Applied Maths, Austin, Tex., USA) and REPUTER (Kurtz and Schleiermacher, 1999). Genome atlas visualizations were constructed using GENEWIZ (Jensen et al., 1999). Pathway reconstructions from the predicted *M. ruminantium* ORFeome were carried out in conjunction with the KEGG (Kyoto Encyclopedia of Genes and Genomes, Kanehisa et al., 2004) on-line database using in-house developed software (PathwayVoyager; Alternann and Klaenhammer, 2005).
Signal Peptide Identification To date there is no signal peptide model for archaea. There are simply too few experimentally verified secretory proteins available for Archaea to train a specific model. For this reason, open reading frames (ORF) sequences were analysed for the presence of signal peptides using SignalP Version 3.0 (Bendtsen et al., 2004) trained against the Gram-positive, Gram-negative and Eukaryotic models. SignalP-HMM (hidden markov models) was used to discriminate between signal peptide and non signal peptide ORFs whereas SignalP-NN (neural networks) was utilised for the prediction of cleavage sites as described by Emanuelsson et al., 2007.

SignalP predicts the presence and location of signal peptide cleavage sites in amino acid sequences from different organisms. The method incorporates a prediction of cleavage sites and a signal peptide/non-signal peptide prediction based on a combination of several artificial neural networks and hidden Markov models. The signal peptide sequences identified from the Gram+ve dataset were aligned and a consensus sequence calculated using the AlignX program of Vector NTI (version 9.1.0, Invitrogen Corporation). The conserved hydrophobic core was identified by analysis of amino acid hydrophobicity.

Figure 3A:
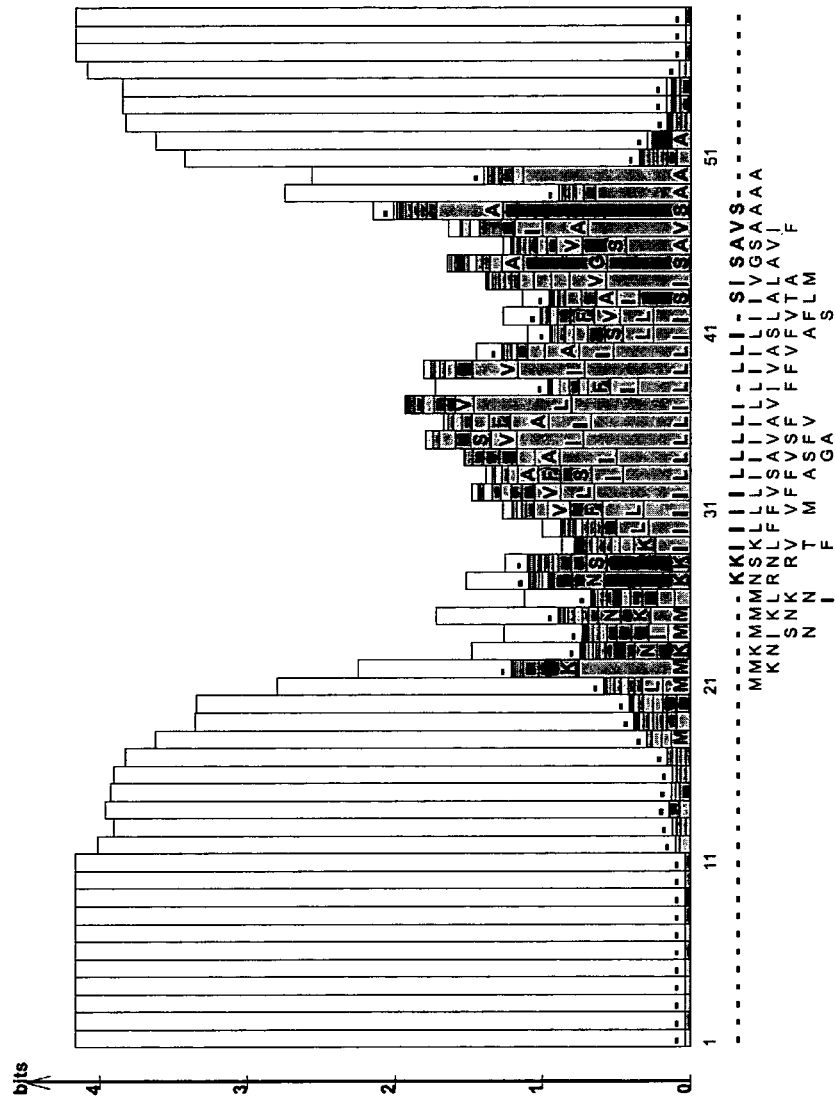
FIG. 3A: Protein sequence logo of 102 sequences created using LogoBar.
Figure 3B:
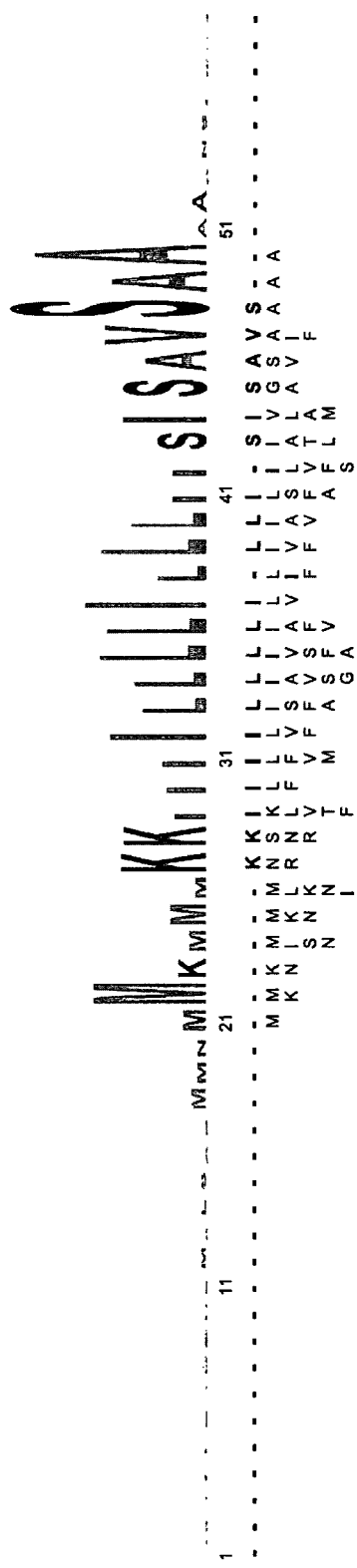
FIG. 3B: Protein sequence logo of 102 sequences created using LogoBar, showing the most conserved amino acid residues.

A consensus dataset was identified from all three SignalP models and the corresponding signal peptide sequences were aligned using ClustalW (Larkin et al., 2007) and edited using BioEdit (hypertext transfer protocol://world wide web.m-bio.ncsu.edu/BioEdit/bioedit.html). A protein sequence logo (FIG. 3A) was created using LogoBar (Perez-Bercoff et al., 2006) to represent the information present in this multiple sequence alignment. In this study ORFs containing a signal peptide and three or more transmembrane domains were considered membrane proteins and were excluded from further analyses. The best Y-score from each of the three models was taken as the putative cleavage site (FIG. 6). Optimised codon usage (FIG. 9) was calculated using an in house perl script: opt_codons.pl (Alternann, E) based on *Escherichia coli* K12 codon table.
Peptide Synthesis and Fluorescein Labelling The core consensus peptide was synthesised commercially using Invitrogen's custom peptide service (Invitrogen NZ Ltd). The peptide was synthesised using Fmoc chemistry on a small scale (10-12 mg) and was HPLC purified to >95% purity. The peptide was labeled at the N-terminal lysine (K) with fluorescein.
Cell-Permeabilisation Assay The entry of the labeled peptide into *M. ruminantium* cells was followed by fluorescence assay. A culture of *M. ruminantium* was grown in 10 ml of BY+ medium and collected by centrifugation at 10,000×g for 10 min at 4° C. The cells were transferred to a 1.5 ml polypropylene Eppendorf tube and washed in 1 ml of TE buffer (10 mM Tris-HCl, 1 mM ethylenediamine tetraacetic acid, pH 8) and collected by centrifugation in a microcentrifuge at 13,000×g for 10 min at 4° C. The cells (approximately $1\times10^8$) were resuspended in a total volume of 200 μl of TE buffer and 20 μg of fluorescein-labeled peptide was added. The mixture was incubated for 30 minutes at 37° C. and then centrifuged at 13,000×g for 10 min at 4° C. The fluid above the cell pellet was retained and constituted the supernatant fraction. The cell pellet was washed 3 times with 2000 of TE buffer by repeatedly resuspending the cells in buffer, and centrifuging at 13,000×g for 10 min at 4° C.

The washes were pooled and constituted the cell wash fraction. The cell pellet remaining after the third wash was resuspended in 200 μl TE buffer containing 1% sodium dodecyl sulphate. The cells were centrifuged at 13,000×g for 10 min at 4° C. to pellet the cells and the fluid above the cell pellet was collected and constituted the cell-associated fraction. The remaining cell pellet was frozen in liquid $N_2$ and cells were physically disrupted by grinding the frozen pellet with a glass rod. The resulting cell homogenate was centrifuged at 20,000×g for 30 min at 4° C. The fluid over the pellet was collected and represented the intracellular fraction, while the remaining pelleted material was resuspended in TE buffer and represented the cell wall/membrane fraction. The fluorescence in each of these fractions was measured by sealing a sample of each fraction in a glass capillary and measuring the emitted fluorescence at 510-533 nm against fluorescein-labeled peptide standards using the fluorescence detector (Channel 1) of a Lightcycler (Roche).

Example 2

Experimental Results

Size estimation of the *M. ruminantium* genome by restriction enzyme digestion of genomic DNA and sizing of fragments via PFGE, indicated a single chromosome of approximately 2.5-2.9 Mb. Initial sequencing of large and small insert clones (6 fold draft coverage) and assembly of the sequence into contigs indicated that a 40 Kb region of the genome was highly over-represented (>20 fold), particularly within the small insert library. Because of this large sequence bias, additional sequencing was carried out (2 fold theoretical genome coverage) for only large insert clones yielding a final 8 fold coverage from Sanger sequencing. The 8 fold draft phase sequence was assembled into 756 contigs which were linked via 105 scaffolds. Further pyrosequencing was carried out to an additional ~10 fold coverage and incorporation of these sequences into the assembly resulted in the contig number dropping to 27. Subsequent gap closure using inverse and long range PCR techniques reduced the contig number to 14.

The combined length of the 14-contig sequence indicate that the genome is slightly larger (2,937,347 bp) than the size estimated by PFGE (FIG. 1A) and significantly larger than its closest relative, *M. smithii* (1.9 Mb). The % G+C of 32.64% is close to the reported 27.5% to 31.6% range reported for *M. ruminantium* strains (Balch et al, 1979). Analysis of the sequence predicts 2,239 ORFs and the total number of hits to protein families (TIGRFam and PFam) and Clusters of Orthologous Groups (COGs) are reported in FIG. 1B. All of the genes predicted to be involved in methanogenesis from $H_2$+$CO_2$ and formate are present (FIG. 1C) However, the draft sequence of *M. ruminantium* lacks a methyl coenzyme reductase II (mcr II or mrt) system. In other methanogens, the mcrII cluster encodes an isoenzyme of the methyl CoM reductase I enzyme which is up-regulated during growth at high partial pressures of $H_2$ (Reeve et al., 1997). $H_2$ is used rapidly in the rumen and does not accumulate to high levels, so *M. ruminantium* appears to be adapted to use low levels of $H_2$ via the mcr I system only.

A total of 169 signal peptide containing ORFs were identified in the genome of *M. ruminantium*. (FIG. 7). Of these, 102 signal peptides were identified by all three SignalP models and the amino acid sequences of these signal peptides were aligned (FIG. 2) and a protein sequence logo created (FIG. 3A). A 17 hydrophobic amino acid core sequence was identified (KKIIIILLLLILLLISI; SEQ ID NO:119). SignalP-HMM calculates the probability of whether the sequence contains a signal peptide. This signal peptide probability is a value between 0 and 1, with 0.5 being defined as a cut-off to distinguish between signal peptide and non-signal peptide for this analysis. The SignalP-NNY score gives the best estimate of where a SP is cleaved (FIG. 6). The Y-score is defined as the geometric average of the C-score (raw cleavage site score) and a smoothed slope of the S-score (signal peptide score) generated by SignalP-NN. The Y-score is a value between 0 and 1 with higher scores indicative of a good cleavage site prediction.

Figures 3C, 3D, 4:
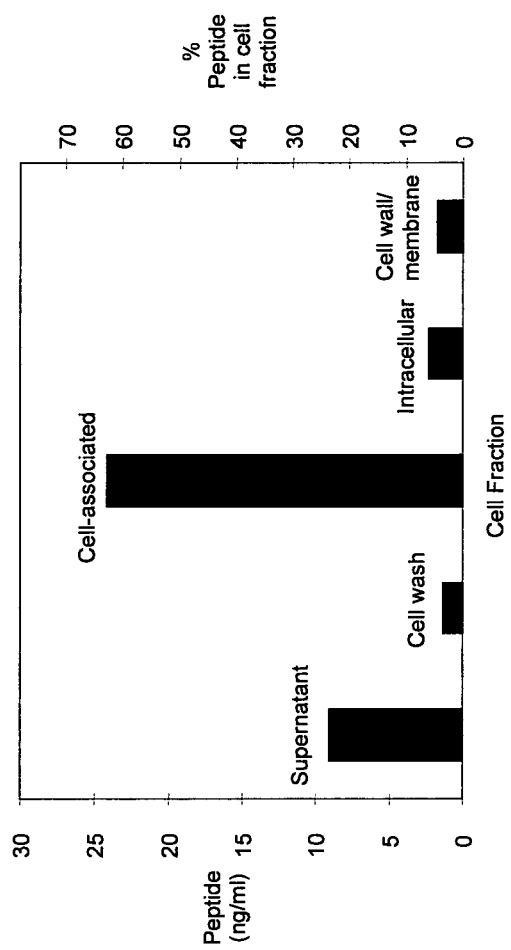
FIG. 3C: Core consensus signal peptide sequence for *M. ruminantium*.
FIG. 3D: Amino acid sequence of a *M. ruminantium* cell-permeabilising peptide with an N-terminal lysine-fluorescein addition.
FIG. 4: Permeabilisation of *M. ruminantium* cells with fluorescein-labelled peptide.
Figure 5:
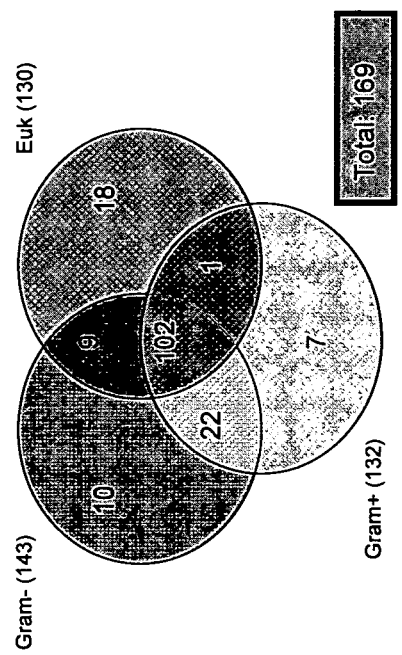
FIG. 5: Venn diagram showing signal peptide predictions of SignalP 3.0-HMM using three different models for *M. ruminantium* signal M1093 orfeome

A consensus amino acid sequence (FIG. 3C) was synthesised and conjugated to the fluorescent tag fluorescein via an additional N-terminal lysine residue (FIG. 3D) making the final length of the peptide 17 amino acids. The purified FITC-peptide was tested for permeabilisation of *M. ruminantium* cells (FIG. 4). In the *M. ruminantium* cell-permeabilising assay 23.5% of the peptide remained in the supernatant unattached to cells after 30 minutes at 37° C. A further 3.4% of the peptide could be removed from the cells by 3 washings with buffer. Approximately 62.9% of the peptide was recovered after a 1% SDS extraction of the cells indicating that the majority of peptide was cell-associated. Of the remaining peptide, 5.8% was found within the intracellular fraction and 4.4% was associated with cell wall/membrane fraction. Therefore 5.8% of the initial peptide (equivalent of 1.16 μg) was able to bind to *M. ruminantium* and cross the cell membrane to enter the cell cytoplasm which represents approximately $2.3\times10^6$ peptide molecules per cell.

Example 3

Overview

*Methanobrevibacter ruminantium* was chosen for genome sequencing because of its prevalence in the rumen under a variety of dietary conditions (based on cultivation and molecular detection data), the availability of cultures, its amenity to routine growth in the laboratory, and the relatively large amount of previous studies and background literature available for this organism. A significant number of the sequences within the *M. ruminantium* have been assigned a function, and have thereby allowed, a detailed picture of this organism's lifestyle within the rumen. *M. ruminantium*'s dependence on simple substrates ($H_2$+$CO_2$, formate) and its interaction with the rumen environment via surface proteins and exopolysaccharides are important targets for inhibition. The sequence data elucidates the metabolism of this organism and how it interacts with other microbes, and points to conserved systems and components among methanogens that can be inactivated to prevent or reduce methane formation in the rumen.

REFERENCES

Alternann E, Klaenhammer T R (2005) PathwayVoyager: pathway mapping using the Kyoto Encyclopedia of Genes and Genomes (KEGG) database. *BMC Genomics* 6:60-66.

Alternann, E., and T. R. Klaenhammer. 2003. GAMOLA: a new local solution for sequence annotation and analyzing draft and finished prokaryotic genomes. Omics 7:161-169.

Altschul S F, Madden T L, Schaffer A A, Zhang J, Zhang Z, Miller W, Lipman D J (1997) Gapped BLAST and PSI-BLAST: a new generation of protein database search programs. *Nucleic Acids Research* 25, 3389-3402.

Balch W E, Fox G E, Magrum L J, Woese C R, Wolfe R S (1979) Methanogens: reevaluation of a unique biological group. *Microbiological Reviews* 43, 260-296.

Baresi, L. and Bertani, G. 1984. Isolation of a bacteriophage for a methanogenic bacterium. In *Abstracts of the Annual Meeting of the American Society for Microbiology. Washington D.C.: American Society for Microbiology, p.* 133.

Bendtsen, J. D., Nielsen, H., von Heijne, G. and Brunak, S. 2004. Improved prediction of signal peptides: SignalP 3.0. J Mol. Biol. 16(4):783-95.

Bickle, T. A. and D. H. Kruger. 1993. Biology of DNA restriction. Microbiol. Rev. 57:434-450.

Bult C J, et al. (1996) Complete genome sequence of the methanogenic archaeon, *Methanococcus jannaschii. Science* 273, 1058-1073.

Coutinho P M, Henrissat B (1999) Carbohydrate-active enzymes: an integrated database approach. In 'Recent Advances in Carbohydrate Bioengineering' (Eds H J Gilbert, G Davies, B Henrissat and B Svensson) pp. 3-12 (The Royal Society of Chemistry, Cambridge) (Carbohydrate Active Enzymes database, http://www.cazy.org/).

Delcher A L, Harmon D, Kasif S, White O, Salzberg S L (1999) Improved microbial gene identification with GLIMMER. *Nucleic Acids Research* 27, 4636-4641.

Emanuelsson, O., Brunak, S., von Heijne, G. and Nielsen, H. 2007. Locating proteins in the cell using TargetP, SignalP and related tools. Nat. Protoc. 2(4):953-71.

Fleischmann et al., 1995. Whole-genome random sequencing and assembly of *Haemophilus influenzae* Rd Science 269: 496-512.

Fricke W F, Seedorf H, Henne A, Kruer M, Liesegang H, Hedderich R, Gottschalk G, Thauer R K (2006) The genome sequence of *Methanosphaera stadtmanae* reveals why this human intestinal archaeon is restricted to methanol and $H_2$ for methane formation and ATP synthesis. *Journal of Bacteriology* 188, 642-658.

Galagan et al. 2002. The genome of *Methanosarcina acetivorans* reveals extensive metabolic and physiological diversity. Genome Res. 12:532-542.

Godde J S, Bickerton A (2006) The repetitive DNAe called CRISPRs and their associated genes: evidence of horizontal transfer among prokaryotes. *Journal of Molecular Evolution* 62, 718-729.

Haft D H, Selengut J, Mongodin E F, Nelson K E (2005) A guild of 45 CRISPR-associated (Cas) protein families and multiple CRISPR/Cas subtypes exist in prokaryotic genomes. *PLoS Computational Biology* 1:474-483

Hamilton, P. T. and J. N. Reeve. 1985. Sequence divergence of an archaebacterial gene cloned from a mesophilic and a thermophilic methanogen. J. Mol. Evol. 22:351-360.

Jansen R, Embden J D, Gaastra W, Schouls L M (2002) Identification of genes that are associated with DNA repeats in prokaryotes. *Molecular Microbiology* 43, 1565-1575.

Jansen R, van Embden J D, Gaastra W, Schouls L M (2002) Identification of a novel family of sequence repeats among prokaryotes. *OMICS: A journal of integrative biology* 6, 23-33.

Jensen, L. J., Friis, C. and Ussery, D. W. 1999 Three views of microbial genomes. Res. Microbiol. 150, 773-777.

Joblin K N, Naylor G E, Williams A G (1990) Effect of *Methanobrevibacter smithii* on xylanolytic activity of anaerobic ruminal fungi. *Applied and Environmental Microbiology* 56, 2287-2295.

Kanehisa M, Goto S, Kawashima S, Okuno Y, Hattori M (2004) The KEGG resource for deciphering the genome. *Nucleic Acids Research* 32, D277-D280.

Kiener, A., Konig, H., Winter, J. and Leisinger, T. 1987. Purification and use of *Methanobacterium wolfei* pseudomurein endopeptidase for lysis of *Methanobacterium thermoautotrophicum*. J. Bacterial. 169, 1010-1016.

Knox, M. R. and Harris, J. E. 1986. Isolation and characterisation of a bacteriophage of *Methanobrevibacter smithii*. In *Abstracts of the XIV International Congress on Microbiology*. Manchester: International Union of Microbiological Societies.

Kurtz S, Schleiermacher C (1999) REPuter: fast computation of maximal repeats in complete genomes. *Bioinformatics* 15, 426-427.

Larkin, M. A., Blackshields, G., Brown, N. P., Chema, R., McGettigan, P. A., McWilliam, H., Valentin, F., Wallace, I. M., Wilm, A., Lopez, R., Thompson, J. D., Gibson, T. J. and Higgins, D. G. Clustal W and Clustal X version 2.0. Bioinformatics 23(21):2947-8.

Lowe T M, Eddy S R (1997) tRNAscan-SE: a program for improved detection of transfer RNA genes in genomic sequence. *Nucleic Acids Research* 25, 955-964.

Loenen, W. and N. Murray. 1986. Modification enhancement by restriction alleviation protein (Ra1) of bacteriophage lambda. J. Mol. Biol. 190:11-22.

Lucchini, S., F. Desiere, and H. Brussow. 1999. Comparative genomics of *Streptococcus thermophilus* phage species supports a modular evolution theory. J. Virol. 73:8647-8656.

Luo, Y. N., Pfister, P., Leisinger, T. and Wasserfallen, A. 2002. Pseudomurein endoisopeptidases PeiW and PeiP, two moderately related members of a novel family of proteases produced in *Methanothermobacter* strains. FEMS Microbiol. Lett. 208, 47-51.

Makarova, K. S., Aravind, L. and Koonin, E. V. 1999. A superfamily of archaeal, bacterial, and eukaryotic proteins homologous to animal transglutaminases. Protein Sci. 8, 1714-1719.

Makarova K S, Grishin N V Shabalina, S A, Wolf Y I, Koonin E V (2006) A putative. RNA-interference-based immune system in prokaryotes: computational analysis of the predicted enzymatic machinery, functional analogies with eukaryotic RNAi, and hypothetical mechanisms of action. *Biology Direct* 1:7-32.

New Zealand Statistics 2005 (www.stats.govt.nz)

New Zealand's Greenhouse Gas Inventory 1990-2004. The National Inventory Report and Common Reporting Format. (2006) Ministry for the Environment. hypertext transfer protocol://www.mfe.govt.nz/publications/climate/nir-apr06/nir-apr06.pdf.

Nielsen, H. Engelbrecht, J. Brunak S, and von Heijne, G. 1997 Identification of prokaryotic and eukaryotic signal peptides and prediction of their cleavage sites. Prot. Eng., 10:1-6.

Ono, M., Wada, Y., Wu, Y., Nemori, R., Jinbo, Y., Wang, H., Lo, K. M., Yamaguchi, N., Brunkhorst, B., Otomo, H. et al. (1997) FP-21399 blocks HIV envelope protein mediated membrane fusion and concentrates in lymph nodes. Nat. Biotechnol. 15, 343-348.

Pérez-Bercoff, A., Koch, J. and Burglin, T. R. 2006. LogoBar: bar graph visualization of protein logos with gaps. Bioinformatics 22(1):112-4.

Rawlings, N. D., Morton, F. R. and Barrett, A. J. 2006. MEROPS: the peptidase database. Nucleic Acids Res. 34, D270-D272.

Reeve J N, Nolling J Morgan R M, Smith D R (1997) Methanogenesis: genes, genomes and who's on first? *Journal of Bacteriology* 179, 5975-5986.

Samuel B S, Hansen E E, Manchester J K, Coutinho P M, Henrissat B, Fulton R, Latreille P, Kim K, Wilson R K, Gordon J I (2007) Genomic adaptations of *Methanobrevibacter smithii* to the human gut. *Proceedings of the National Academy of Sciences USA* 104, 10643-10648.

Salzberg et al., 1998. Microbial gene identification using interpolated Markov models. Nucleic Acids Res. 26:544-8.

Smith et al., 1997. Complete genome sequence of *Methanobacterium thermoautotrophicum* deltaH: functional analysis and comparative genomics J. Bacteriol. 179:7135-7155.

Smith P H, Hungate R E (1958) Isolation and characterization of *Methanobacterium ruminantium* n. sp. *Journal of Bacteriology* 75, 713-718.

Staden R, Beal K F, Bonfield J K (1998) The Staden Package. *Methods in Molecular Biology Bioinformatics Methods and Protocols* 132, 115-130.

Tatusov R L, Natale D A, Garkavtsev I V, Tatusova T A, Shankavaram U T, Rao B S, Kiryutin B, Galperin M Y, Fedorova N D, Koonin E V (2001) The COG database: new developments in phylogenetic classification of proteins from complete genomes *Nucleic Acids Research* 29, 22-28.

von Heijne, G. 1985. Signal sequences: The limits of variation *J. Mol. Biol.* 184, 99-105.

All publications and patents mentioned in the above specification are herein incorporated by reference.

Where the foregoing description reference has been made to integers having known equivalents thereof, those equivalents are herein incorporated as if individually set forth.

Although the invention has been described in connection with specific preferred embodiments, it should be understood that the invention as claimed should not be unduly limited to such specific embodiments.

It is appreciated that further modifications may be made to the invention as described herein without departing from the spirit and scope of the invention.

What we claim is:

1. An isolated polypeptide or isolated peptide comprising an amino acid sequence selected from the group consisting of SEQ ID NO: 117, 118, and 119.

2. An isolated polypeptide or isolated peptide which comprises: a) an amino acid sequence sharing at least 90% identity with SEQ ID NO:117; b) an amino acid sequence sharing at least 95% identity with SEQ ID NO:118; or c) an amino acid sequence sharing at least 90% identity with SEQ ID NO:119.

3. An isolated polypeptide or isolated peptide which comprises: a) at least 15 amino acids of SEQ ID NO:117 or 118; or b) at least 15 amino acids of SEQ ID NO:119.

4. A conjugate molecule or fusion molecule which comprises the isolated polypeptide or isolated peptide of any one of claims 1 to 3.

5. A method of permeabilising a microbial cell, comprising contacting the cell with the isolated polypeptide or isolated peptide of any one of claims 1 to 3.

6. The method of claim 5, wherein the cell is a methanogen.

7. The method of claim 6, wherein the cell is *Methanobrevibacter ruminantium*.

8. The method of claim 7, wherein the cell is *Methanobrevibacter ruminantium* strain M1$^T$ (DSM1093).

9. A method of permeabilising a microbial cell, comprising contacting the cell with the conjugate molecule or the fusion molecule of claim 4.

10. The method of claim 9, wherein the cell is a methanogen.

11. The method of claim 10, wherein the cell is *Methanobrevibacter ruminantium*.

12. The method of claim 11, wherein the cell is *Methanobrevibacter ruminantium* strain M1$^T$ (DSM1093).

13. The conjugate molecule or fusion molecule of claim 4, which further comprises an anti-methanogenesis compound, an antibody or antibody fragment, a lytic enzyme, a peptide nucleic acid, an antimicrobial peptide, or an antibiotic.

14. The method of claim 5, further comprising producing or isolating the polypeptide or peptide of any one of claims 1 to 3.

15. The method of claim 9, further comprising producing or isolating the conjugate molecule or fusion molecule of claim 4.

* * * * *

SEQUENCE LISTING

```
<160> NUMBER OF SEQ ID NOS: 514

<210> SEQ ID NO 1
<211> LENGTH: 18
<212> TYPE: PRT
<213> ORGANISM: Methanobrevibacter ruminantium

<400> SEQUENCE: 1

Met Val Leu Ala Leu Ser Ile Ile Leu Leu Ser Ser Ile Ala Ala Ala
1               5                   10                  15

Ser Ala
```

```
<210> SEQ ID NO 2
<211> LENGTH: 18
<212> TYPE: PRT
<213> ORGANISM: Methanobrevibacter ruminantium

<400> SEQUENCE: 2

Met Ser Thr Phe Ile Leu Val Ile Ile Ile Leu Gly Ile Ile Leu Ile
1               5                   10                  15

Ile Ala

<210> SEQ ID NO 3
<211> LENGTH: 25
<212> TYPE: PRT
<213> ORGANISM: Methanobrevibacter ruminantium

<400> SEQUENCE: 3

Met Asp Asn Lys Lys Ile Phe Val Ile Val Ala Leu Ala Leu Leu Ala
1               5                   10                  15

Ile Val Ala Val Gly Ser Val Ser Ala
            20                  25

<210> SEQ ID NO 4
<211> LENGTH: 25
<212> TYPE: PRT
<213> ORGANISM: Methanobrevibacter ruminantium

<400> SEQUENCE: 4

Met Asn Asn Lys Lys Ile Phe Ala Ile Ala Ala Leu Ala Ile Ile Ala
1               5                   10                  15

Ile Val Ala Val Gly Ser Val Ser Ala
            20                  25

<210> SEQ ID NO 5
<211> LENGTH: 25
<212> TYPE: PRT
<213> ORGANISM: Methanobrevibacter ruminantium

<400> SEQUENCE: 5

Met Asn Ala Lys Lys Leu Thr Ile Leu Ala Ala Leu Ala Ile Leu Ala
1               5                   10                  15

Ile Val Ala Val Gly Ser Val Ser Ala
            20                  25

<210> SEQ ID NO 6
<211> LENGTH: 22
<212> TYPE: PRT
<213> ORGANISM: Methanobrevibacter ruminantium

<400> SEQUENCE: 6

Met Ile Cys Cys Val Leu Leu Thr Phe Ser Thr Val Ser Ala Ile Asp
1               5                   10                  15

Met Asp Gly Asn Leu Thr
            20

<210> SEQ ID NO 7
<211> LENGTH: 16
<212> TYPE: PRT
<213> ORGANISM: Methanobrevibacter ruminantium

<400> SEQUENCE: 7

Met Ile Ile Ala Ile Ile Phe Met Tyr Asn Arg Val Arg Asn Lys Arg
1               5                   10                  15
```

```
<210> SEQ ID NO 8
<211> LENGTH: 25
<212> TYPE: PRT
<213> ORGANISM: Methanobrevibacter ruminantium

<400> SEQUENCE: 8

Met Asn Lys Val Gln Leu Ser Ser Ile Leu Ala Leu Val Leu Ile Leu
1               5                   10                  15

Phe Leu Ser Leu Ala Val Val Ser Ala
            20                  25

<210> SEQ ID NO 9
<211> LENGTH: 24
<212> TYPE: PRT
<213> ORGANISM: Methanobrevibacter ruminantium

<400> SEQUENCE: 9

Met Arg Lys Glu Ile Ile Ser Ile Leu Val Ile Ala Ile Ile Ala Ile
1               5                   10                  15

Ser Val Ile Pro Thr Ala Phe Ser
            20

<210> SEQ ID NO 10
<211> LENGTH: 30
<212> TYPE: PRT
<213> ORGANISM: Methanobrevibacter ruminantium

<400> SEQUENCE: 10

Met Asn Lys Lys Arg Phe Lys Leu Leu Leu Thr Ile Phe Ile Ala Phe
1               5                   10                  15

Ala Leu Ile Asn Thr Cys Phe Ile Leu Asn Asp Asn Leu Ser
            20                  25                  30

<210> SEQ ID NO 11
<211> LENGTH: 22
<212> TYPE: PRT
<213> ORGANISM: Methanobrevibacter ruminantium

<400> SEQUENCE: 11

Met Met Val Ile Leu Leu Ile Thr Leu Leu Ser Val Pro Ile Leu Ser
1               5                   10                  15

Leu Thr Ile Asp Tyr Ser
            20

<210> SEQ ID NO 12
<211> LENGTH: 28
<212> TYPE: PRT
<213> ORGANISM: Methanobrevibacter ruminantium

<400> SEQUENCE: 12

Met Asn Ile Asn Leu Lys Lys Ile Thr Phe Leu Cys Leu Val Leu Val
1               5                   10                  15

Leu Ile Gly Leu Ile Ser Phe Asn Ser Ile Ser Ala
            20                  25

<210> SEQ ID NO 13
<211> LENGTH: 22
<212> TYPE: PRT
<213> ORGANISM: Methanobrevibacter ruminantium
```

```
<400> SEQUENCE: 13

Met Asn Asn Gln Asn Lys Tyr Ser Cys Ile Val Leu Ala Gly Gly Met
1               5                   10                  15

Ser Arg Arg Met Gly Gln
            20

<210> SEQ ID NO 14
<211> LENGTH: 33
<212> TYPE: PRT
<213> ORGANISM: Methanobrevibacter ruminantium

<400> SEQUENCE: 14

Met Glu Asp Arg Lys Ala Lys Phe Ile Val Tyr Val Val Cys Leu
1               5                   10                  15

Leu Ala Phe Ile Cys Ser Ser Thr Val Phe Ser Met Thr Gly Gly Leu
            20                  25                  30

Ser

<210> SEQ ID NO 15
<211> LENGTH: 23
<212> TYPE: PRT
<213> ORGANISM: Methanobrevibacter ruminantium

<400> SEQUENCE: 15

Met Asn Ile Leu Ile Asn Gly Thr Gly Ala Ile Gly Ile Gly Leu Gly
1               5                   10                  15

Ala Ser Met Ile Ser Gln Gly
            20

<210> SEQ ID NO 16
<211> LENGTH: 27
<212> TYPE: PRT
<213> ORGANISM: Methanobrevibacter ruminantium

<400> SEQUENCE: 16

Met Ile Ile Val Thr Thr Ile Cys Val Ile Leu Ile Leu Ile Val Leu
1               5                   10                  15

Phe Tyr Gly Leu Phe Pro Gly Leu Thr Asn Ser
            20                  25

<210> SEQ ID NO 17
<211> LENGTH: 21
<212> TYPE: PRT
<213> ORGANISM: Methanobrevibacter ruminantium

<400> SEQUENCE: 17

Met Ser Asp Val Gly Lys Thr Val Ile Thr Thr Ile Ile Thr Leu Val
1               5                   10                  15

Thr Thr Ala Phe Gly
            20

<210> SEQ ID NO 18
<211> LENGTH: 27
<212> TYPE: PRT
<213> ORGANISM: Methanobrevibacter ruminantium

<400> SEQUENCE: 18

Leu Lys Ser Asp Lys Arg Ala Lys Phe Ala Ile Phe Phe Ser Ile Ala
1               5                   10                  15

Ile Leu Ala Leu Gly Leu Ser Asn Ile Ala Ala
            20                  25
```

```
<210> SEQ ID NO 19
<211> LENGTH: 36
<212> TYPE: PRT
<213> ORGANISM: Methanobrevibacter ruminantium

<400> SEQUENCE: 19

Met Ile Asn Gly Ile Met Asp Lys Gln Lys Val Ile Thr Ala Phe Gly
1               5                   10                  15

Ile Ile Leu Phe Leu Ala Ala Ala Phe Ser Pro Phe Val Val Leu Pro
            20                  25                  30

Ile Leu Gly Val
        35

<210> SEQ ID NO 20
<211> LENGTH: 25
<212> TYPE: PRT
<213> ORGANISM: Methanobrevibacter ruminantium

<400> SEQUENCE: 20

Met Phe Asn Lys Lys Met Val Leu Ala Ile Ser Leu Leu Ala Val Ile
1               5                   10                  15

Phe Ala Ser Met Cys Ile Val Ser Ala
            20                  25

<210> SEQ ID NO 21
<211> LENGTH: 28
<212> TYPE: PRT
<213> ORGANISM: Methanobrevibacter ruminantium

<400> SEQUENCE: 21

Met Lys Thr Asn Leu Lys Lys Thr Thr Ile Ile Leu Ala Leu Leu Met
1               5                   10                  15

Ala Ile Leu Ile Leu Ser Ile Gly Ala Ile Ser Ala
            20                  25

<210> SEQ ID NO 22
<211> LENGTH: 26
<212> TYPE: PRT
<213> ORGANISM: Methanobrevibacter ruminantium

<400> SEQUENCE: 22

Met Asn Ser Lys Gly Lys Tyr Leu Val Leu Phe Leu Ile Leu Ile Leu
1               5                   10                  15

Ser Phe Ser Ile Ile Ser Ala Ser Phe Ala
            20                  25

<210> SEQ ID NO 23
<211> LENGTH: 28
<212> TYPE: PRT
<213> ORGANISM: Methanobrevibacter ruminantium

<400> SEQUENCE: 23

Met Lys Lys Asn Leu Ser Leu Lys Asn Ile Leu Ile Leu Ser Leu Ile
1               5                   10                  15

Phe Leu Phe Val Leu Ser Ile Gly Ser Ser Phe Ala
            20                  25

<210> SEQ ID NO 24
<211> LENGTH: 24
<212> TYPE: PRT
<213> ORGANISM: Methanobrevibacter ruminantium
```

-continued

```
<400> SEQUENCE: 24

Met Lys Arg Asn Ile Tyr Phe Ile Ile Leu Leu Val Thr Leu Phe Leu
1               5                   10                  15

Ile Ser Met Ser Val Val Ser Ala
            20

<210> SEQ ID NO 25
<211> LENGTH: 22
<212> TYPE: PRT
<213> ORGANISM: Methanobrevibacter ruminantium

<400> SEQUENCE: 25

Met Lys Lys Met Glu Met Ala Ser Tyr Ile Ile Leu Ile Ala Ser Val
1               5                   10                  15

Leu Ala Ile Leu Tyr Ala
            20

<210> SEQ ID NO 26
<211> LENGTH: 24
<212> TYPE: PRT
<213> ORGANISM: Methanobrevibacter ruminantium

<400> SEQUENCE: 26

Met Pro Lys Ile Ala Lys Leu Trp Asn Lys Leu Ala Asp Pro Lys Asn
1               5                   10                  15

Ile Pro Arg Leu Phe Ala Val Ile
            20

<210> SEQ ID NO 27
<211> LENGTH: 31
<212> TYPE: PRT
<213> ORGANISM: Methanobrevibacter ruminantium

<400> SEQUENCE: 27

Met Phe Asn Leu Ala Ile Trp Val Tyr Leu Gly Leu Ala Leu Ala Ile
1               5                   10                  15

Phe Gly Ser Leu Ala Thr Val Trp Gly Pro Gly Val Lys Asp Pro
            20                  25                  30

<210> SEQ ID NO 28
<211> LENGTH: 27
<212> TYPE: PRT
<213> ORGANISM: Methanobrevibacter ruminantium

<400> SEQUENCE: 28

Leu Phe Ala Ile Val Ser Leu Ser Ala Val Ser Ala Ser Asp Asp Phe
1               5                   10                  15

Ser Ser Ser Leu Ala Asp Asp Ser Asp Ser Asp
            20                  25

<210> SEQ ID NO 29
<211> LENGTH: 24
<212> TYPE: PRT
<213> ORGANISM: Methanobrevibacter ruminantium

<400> SEQUENCE: 29

Met Lys Arg Arg Tyr Lys Val Leu Phe Leu Leu Ala Ile Leu Thr Ile
1               5                   10                  15

Ile Ser Ile Asn Ala Ile Ser Ala
            20

<210> SEQ ID NO 30
```

```
<211> LENGTH: 13
<212> TYPE: PRT
<213> ORGANISM: Methanobrevibacter ruminantium

<400> SEQUENCE: 30

Met Leu Phe Ser Val Ile Ala Thr Val Ser Ala Thr Cys
1               5                   10

<210> SEQ ID NO 31
<211> LENGTH: 14
<212> TYPE: PRT
<213> ORGANISM: Methanobrevibacter ruminantium

<400> SEQUENCE: 31

Met Phe Ile Lys Ile Arg Arg Asp Thr Leu Ile Ile Leu Leu
1               5                   10

<210> SEQ ID NO 32
<211> LENGTH: 35
<212> TYPE: PRT
<213> ORGANISM: Methanobrevibacter ruminantium

<400> SEQUENCE: 32

Met Lys Ala Val Ile Pro Ala Ala Gly Leu Gly Thr Arg Phe Leu Pro
1               5                   10                  15

Ala Thr Lys Ala Gln Pro Lys Glu Met Leu Pro Val Tyr Asp Lys Pro
            20                  25                  30

Thr Ile Gln
        35

<210> SEQ ID NO 33
<211> LENGTH: 26
<212> TYPE: PRT
<213> ORGANISM: Methanobrevibacter ruminantium

<400> SEQUENCE: 33

Met Ile Lys Thr Asp Val Leu Val Ile Gly Ala Gly Pro Ala Gly Ser
1               5                   10                  15

Ser Ala Ala Arg Phe Ala Ala Lys Gly Gly
            20                  25

<210> SEQ ID NO 34
<211> LENGTH: 29
<212> TYPE: PRT
<213> ORGANISM: Methanobrevibacter ruminantium

<400> SEQUENCE: 34

Met Glu Asp Asn Leu Leu Lys Asn Arg Lys Leu Ile Leu Ile Ser Ile
1               5                   10                  15

Phe Leu Val Ser Leu Leu Ala Ile Ser Ala Val Ser Ala
            20                  25

<210> SEQ ID NO 35
<211> LENGTH: 26
<212> TYPE: PRT
<213> ORGANISM: Methanobrevibacter ruminantium

<400> SEQUENCE: 35

Met Asn Arg Asn Lys Ile Ile Val Leu Leu Val Leu Leu Ile Ala Val
1               5                   10                  15

Val Gly Phe Thr Met Gly Pro Ala Cys Ala
            20                  25
```

```
<210> SEQ ID NO 36
<211> LENGTH: 24
<212> TYPE: PRT
<213> ORGANISM: Methanobrevibacter ruminantium

<400> SEQUENCE: 36

Met Lys Lys Ser Val Phe Lys Ile Leu Ile Ala Leu Ala Leu Ile Leu
1               5                   10                  15

Leu Ala Val Ser Ile Val Ser Ser
            20

<210> SEQ ID NO 37
<211> LENGTH: 21
<212> TYPE: PRT
<213> ORGANISM: Methanobrevibacter ruminantium

<400> SEQUENCE: 37

Met Lys Lys Asn Ile Phe Leu Ile Ala Ile Ile Leu Ile Ala Val Val
1               5                   10                  15

Ala Val Ser Gly Cys
            20

<210> SEQ ID NO 38
<211> LENGTH: 22
<212> TYPE: PRT
<213> ORGANISM: Methanobrevibacter ruminantium

<400> SEQUENCE: 38

Met Leu Ile Ala Leu Leu Gly Leu Ser Ala Val Ala Ala Val Asp Ala
1               5                   10                  15

Asp Pro Leu Thr Asp Asn
            20

<210> SEQ ID NO 39
<211> LENGTH: 18
<212> TYPE: PRT
<213> ORGANISM: Methanobrevibacter ruminantium

<400> SEQUENCE: 39

Met Ser Glu Asn Asn Arg Thr Leu Ile Thr Ile Gly Ile Gly Ala Phe
1               5                   10                  15

Ile Ile

<210> SEQ ID NO 40
<211> LENGTH: 31
<212> TYPE: PRT
<213> ORGANISM: Methanobrevibacter ruminantium

<400> SEQUENCE: 40

Met Gly Lys Ile Phe Lys Ile Val Thr Ile Ile Leu Ile Val Ile Ala
1               5                   10                  15

Leu Ala Ile Leu Gly Val Phe Ile Tyr Ser Asp Gly His Ser Glu
            20                  25                  30

<210> SEQ ID NO 41
<211> LENGTH: 16
<212> TYPE: PRT
<213> ORGANISM: Methanobrevibacter ruminantium

<400> SEQUENCE: 41

Met Asp Lys Lys Thr Ile Ile Ile Ala Ala Val Ala Ile Leu Val Ile
1               5                   10                  15
```

```
<210> SEQ ID NO 42
<211> LENGTH: 24
<212> TYPE: PRT
<213> ORGANISM: Methanobrevibacter ruminantium

<400> SEQUENCE: 42

Met Lys Leu Asn Lys Phe Phe Ile Ile Ser Ile Ile Leu Ile Ile Phe
1               5                   10                  15

Leu Ser Ile Ser Ala Ile Ser Ala
            20

<210> SEQ ID NO 43
<211> LENGTH: 24
<212> TYPE: PRT
<213> ORGANISM: Methanobrevibacter ruminantium

<400> SEQUENCE: 43

Met Lys Lys Lys Ile Ala Ile Ile Leu Gly Ile Ala Leu Leu Ala Phe
1               5                   10                  15

Leu Val Ile Gly Ala Ser Ser Ala
            20

<210> SEQ ID NO 44
<211> LENGTH: 24
<212> TYPE: PRT
<213> ORGANISM: Methanobrevibacter ruminantium

<400> SEQUENCE: 44

Met Asn Phe Asn Lys Lys Ile Leu Leu Ile Ile Ala Leu Val Phe Ile
1               5                   10                  15

Ala Ser Val Gly Ile Val Ala Ala
            20

<210> SEQ ID NO 45
<211> LENGTH: 23
<212> TYPE: PRT
<213> ORGANISM: Methanobrevibacter ruminantium

<400> SEQUENCE: 45

Met Lys Arg Ser Ile Ile Phe Leu Thr Ile Ile Leu Ser Leu Phe Leu
1               5                   10                  15

Val Ile Gly Tyr Ala Ser Ala
            20

<210> SEQ ID NO 46
<211> LENGTH: 32
<212> TYPE: PRT
<213> ORGANISM: Methanobrevibacter ruminantium

<400> SEQUENCE: 46

Val Gly Ile Thr Phe Thr Ala Ile Ile Thr Gly Ala Leu Gly Gly Thr
1               5                   10                  15

Thr Phe Ser Glu Pro Leu Gly Asn Tyr Leu Ser Gln Phe Ile Pro Tyr
            20                  25                  30

<210> SEQ ID NO 47
<211> LENGTH: 25
<212> TYPE: PRT
<213> ORGANISM: Methanobrevibacter ruminantium

<400> SEQUENCE: 47

Met Asp Ser Lys Lys Leu Ile Leu Val Thr Ala Leu Ala Phe Leu Ala
1               5                   10                  15
```

Ile Val Ser Ile Ala Ser Val Ser Ala
            20                  25

<210> SEQ ID NO 48
<211> LENGTH: 35
<212> TYPE: PRT
<213> ORGANISM: Methanobrevibacter ruminantium

<400> SEQUENCE: 48

Met Asn Val Asn Lys Lys Ile Phe Leu Leu Val Ile Phe Ile Ile Ser
1               5                   10                  15

Ile Ser Ile Ala Gly Val Tyr Cys Ala Asp Ile His Gln Asp Ser Asp
            20                  25                  30

Leu Thr Ala
        35

<210> SEQ ID NO 49
<211> LENGTH: 20
<212> TYPE: PRT
<213> ORGANISM: Methanobrevibacter ruminantium

<400> SEQUENCE: 49

Met Ile Leu Ala Leu Phe Cys Phe Ile Val Ile Gly Ser Ala Ser Ala
1               5                   10                  15

Ala Asp Phe Lys
        20

<210> SEQ ID NO 50
<211> LENGTH: 18
<212> TYPE: PRT
<213> ORGANISM: Methanobrevibacter ruminantium

<400> SEQUENCE: 50

Met Ile Ser Leu Leu Leu Ile Ser Ile Leu Ala Ile Ser Ala Ala Ser
1               5                   10                  15

Ala Ala

<210> SEQ ID NO 51
<211> LENGTH: 30
<212> TYPE: PRT
<213> ORGANISM: Methanobrevibacter ruminantium

<400> SEQUENCE: 51

Met Glu Glu Lys Ile Ala Leu Ala Ala Cys Ser Gly Met Ser Pro Asn
1               5                   10                  15

Gly Leu Val Ala Arg Val Ala Val His Asp Leu Ala Ile Asp
            20                  25                  30

<210> SEQ ID NO 52
<211> LENGTH: 26
<212> TYPE: PRT
<213> ORGANISM: Methanobrevibacter ruminantium

<400> SEQUENCE: 52

Met Leu Lys Thr Lys Leu Cys Gly Ile Ser Leu Lys Asn Pro Leu Met
1               5                   10                  15

Leu Ala Ala Gly Val Leu Gly Ser His Ala
            20                  25

<210> SEQ ID NO 53
<211> LENGTH: 27
<212> TYPE: PRT
<213> ORGANISM: Methanobrevibacter ruminantium

<400> SEQUENCE: 53

Met Glu Ile Val Leu Cys Val Thr Gly Ser Val Ala Ala Val Glu Thr
1               5                   10                  15

Val Lys Leu Ala Arg Glu Phe Lys Arg Gln Gly
            20                  25

<210> SEQ ID NO 54
<211> LENGTH: 21
<212> TYPE: PRT
<213> ORGANISM: Methanobrevibacter ruminantium

<400> SEQUENCE: 54

Met Val Val Ala Thr Ile Ile Phe Ala Ser Ser Leu Phe Asp Ala Leu
1               5                   10                  15

Tyr Gly Phe Lys Asn
            20

<210> SEQ ID NO 55
<211> LENGTH: 18
<212> TYPE: PRT
<213> ORGANISM: Methanobrevibacter ruminantium

<400> SEQUENCE: 55

Met Ile Leu Ala Ile Leu Leu Ala Val Gly Met Thr Leu Thr Ala Val
1               5                   10                  15

Ser Ala

<210> SEQ ID NO 56
<211> LENGTH: 25
<212> TYPE: PRT
<213> ORGANISM: Methanobrevibacter ruminantium

<400> SEQUENCE: 56

Met Asn Lys Arg Ile Phe Leu Tyr Ile Ala Leu Ile Phe Ile Ile Ser
1               5                   10                  15

Leu Leu Ser Phe Ser Ala Val Ser Ala
            20                  25

<210> SEQ ID NO 57
<211> LENGTH: 23
<212> TYPE: PRT
<213> ORGANISM: Methanobrevibacter ruminantium

<400> SEQUENCE: 57

Met Lys Tyr Asn Lys Lys Ile Phe Phe Leu Phe Leu Leu Leu Cys Leu
1               5                   10                  15

Ile Ile Pro Gln Ala Ile Tyr
            20

<210> SEQ ID NO 58
<211> LENGTH: 25
<212> TYPE: PRT
<213> ORGANISM: Methanobrevibacter ruminantium

<400> SEQUENCE: 58

Met Asn Ser Asn Lys Thr Tyr Ala Val Leu Gly Leu Leu Leu Leu Leu
1               5                   10                  15

Ile Leu Ser Ile Gly Ala Ile Ser Ala
            20                  25

<210> SEQ ID NO 59

```
<211> LENGTH: 27
<212> TYPE: PRT
<213> ORGANISM: Methanobrevibacter ruminantium

<400> SEQUENCE: 59

Met Ile Asn Lys Arg Ile Ile Ser Leu Ser Leu Leu Ile Ile Leu Val
1               5                   10                  15

Phe Leu Ile Ile Gly Leu Ser Ala Val Ser Ala
            20                  25

<210> SEQ ID NO 60
<211> LENGTH: 25
<212> TYPE: PRT
<213> ORGANISM: Methanobrevibacter ruminantium

<400> SEQUENCE: 60

Met Asp Phe Lys Lys Ala Ile Pro Leu Phe Ala Leu Leu Leu Leu Ile
1               5                   10                  15

Leu Phe Ile Ile Gly Ser Ser Ser Ala
            20                  25

<210> SEQ ID NO 61
<211> LENGTH: 25
<212> TYPE: PRT
<213> ORGANISM: Methanobrevibacter ruminantium

<400> SEQUENCE: 61

Met Lys Leu Lys Lys Phe Ser Val Ile Leu Ala Val Leu Leu Val Ala
1               5                   10                  15

Ile Leu Ala Ile Gly Ala Val Ser Ala
            20                  25

<210> SEQ ID NO 62
<211> LENGTH: 18
<212> TYPE: PRT
<213> ORGANISM: Methanobrevibacter ruminantium

<400> SEQUENCE: 62

Met Ile Leu Ile Ser Leu Ile Leu Val Ile Leu Ser Ile Ser Cys Val
1               5                   10                  15

Ser Ala

<210> SEQ ID NO 63
<211> LENGTH: 22
<212> TYPE: PRT
<213> ORGANISM: Methanobrevibacter ruminantium

<400> SEQUENCE: 63

Met Asp Asn Ser Asn Ile Ile Ser Val Ile Ile Val Leu Cys Ile
1               5                   10                  15

Ala Ala Gly Val Thr Ala
            20

<210> SEQ ID NO 64
<211> LENGTH: 22
<212> TYPE: PRT
<213> ORGANISM: Methanobrevibacter ruminantium

<400> SEQUENCE: 64

Met Asp Asn Ser Ser Ile Leu Ile Ser Val Ile Ile Val Leu Cys Ile
1               5                   10                  15

Ala Ala Gly Val Thr Ala
            20
```

<210> SEQ ID NO 65
<211> LENGTH: 22
<212> TYPE: PRT
<213> ORGANISM: Methanobrevibacter ruminantium

<400> SEQUENCE: 65

Met Arg Lys Glu Ile Leu Ile Ala Ala Ile Ala Ile Ile Leu Ile Leu
1               5                   10                  15

Cys Gly Gly Val Phe Ala
            20

<210> SEQ ID NO 66
<211> LENGTH: 18
<212> TYPE: PRT
<213> ORGANISM: Methanobrevibacter ruminantium

<400> SEQUENCE: 66

Met Leu Ile Ser Ile Val Leu Ile Ser Leu Ile Ala Leu Gly Ala Val
1               5                   10                  15

Ser Ala

<210> SEQ ID NO 67
<211> LENGTH: 21
<212> TYPE: PRT
<213> ORGANISM: Methanobrevibacter ruminantium

<400> SEQUENCE: 67

Met Lys Glu Ile Ala Ile Tyr Leu Ile Leu Ile Ile Ile Val Leu Ile
1               5                   10                  15

Ala Ala Gln His Leu
            20

<210> SEQ ID NO 68
<211> LENGTH: 21
<212> TYPE: PRT
<213> ORGANISM: Methanobrevibacter ruminantium

<400> SEQUENCE: 68

Leu Phe Glu Ala Gly Met Ile Ala Leu Pro Thr Gly Leu Pro Gly Leu
1               5                   10                  15

Ala Leu Leu Gly Leu
            20

<210> SEQ ID NO 69
<211> LENGTH: 22
<212> TYPE: PRT
<213> ORGANISM: Methanobrevibacter ruminantium

<400> SEQUENCE: 69

Met Lys Asn Trp Lys Ile Ile Gly Leu Ile Leu Ile Ile Leu Leu Ala
1               5                   10                  15

Val Val Ser Val Ser Gly
            20

<210> SEQ ID NO 70
<211> LENGTH: 34
<212> TYPE: PRT
<213> ORGANISM: Methanobrevibacter ruminantium

<400> SEQUENCE: 70

Met Lys Pro Leu Ile Ile Lys Ile Ser Ile Phe Cys Asn Lys Lys Ile
1               5                   10                  15

-continued

Phe Ile Phe Thr Leu Met Ile Val Met Leu Leu Ser Leu Ala Ala Val
            20                  25                  30

Ser Ala

<210> SEQ ID NO 71
<211> LENGTH: 25
<212> TYPE: PRT
<213> ORGANISM: Methanobrevibacter ruminantium

<400> SEQUENCE: 71

Met Ser Ile Lys Arg Ile Leu Leu Thr Ser Leu Met Leu Phe Ile Ile
1               5                   10                  15

Ile Phe Ser Ile Ser Phe Val Ser Ala
            20                  25

<210> SEQ ID NO 72
<211> LENGTH: 24
<212> TYPE: PRT
<213> ORGANISM: Methanobrevibacter ruminantium

<400> SEQUENCE: 72

Met Asp Lys Val Gly Ile Ile Gly Ala Gly Ser Leu Gly Thr Ala Leu
1               5                   10                  15

Ala Gln Thr Val Ala Asn Asn Val
            20

<210> SEQ ID NO 73
<211> LENGTH: 19
<212> TYPE: PRT
<213> ORGANISM: Methanobrevibacter ruminantium

<400> SEQUENCE: 73

Leu Ile Cys Ser Ile Gln Ala Cys Ser Ala Ser Cys Thr Ala Val Tyr
1               5                   10                  15

Val Gly Pro

<210> SEQ ID NO 74
<211> LENGTH: 30
<212> TYPE: PRT
<213> ORGANISM: Methanobrevibacter ruminantium

<400> SEQUENCE: 74

Met Lys Ile Ser Arg Ile Ile Leu Ile Leu Leu Leu Phe Val Val Phe
1               5                   10                  15

Phe Glu Ile Gly Leu Phe Ser Ser Tyr Thr Ile Val Asn Ala
            20                  25                  30

<210> SEQ ID NO 75
<211> LENGTH: 20
<212> TYPE: PRT
<213> ORGANISM: Methanobrevibacter ruminantium

<400> SEQUENCE: 75

Met Ile Leu Ile Ile Ser Leu Phe Leu Ile Ser Leu Leu Ala Ile Gly
1               5                   10                  15

Ala Ala Ser Ala
            20

<210> SEQ ID NO 76
<211> LENGTH: 24
<212> TYPE: PRT
<213> ORGANISM: Methanobrevibacter ruminantium

<400> SEQUENCE: 76

Met Lys Leu Tyr Lys Asn Ser Ile Ile Leu Leu Ile Leu Ile
1               5                   10                  15
Leu Ser Ile Gly Ala Ala Ala Ala
                20

<210> SEQ ID NO 77
<211> LENGTH: 22
<212> TYPE: PRT
<213> ORGANISM: Methanobrevibacter ruminantium

<400> SEQUENCE: 77

Leu Ala Val Ile Leu Ile Ile Leu Phe Ser Leu Gly Thr Val Ala Ala
1               5                   10                  15
Ser Glu Asn Ile Val Ile
                20

<210> SEQ ID NO 78
<211> LENGTH: 31
<212> TYPE: PRT
<213> ORGANISM: Methanobrevibacter ruminantium

<400> SEQUENCE: 78

Met Arg Asn Pro Lys Asp Tyr Ile Met Lys Thr Asp Tyr Leu Ile Ile
1               5                   10                  15
Leu Met Ala Leu Leu Leu Ile Ser Ile Val Ser Pro Ile Ala Ala
                20                  25                  30

<210> SEQ ID NO 79
<211> LENGTH: 23
<212> TYPE: PRT
<213> ORGANISM: Methanobrevibacter ruminantium

<400> SEQUENCE: 79

Met Asn Asn Lys Lys Ile Phe Val Ala Gly Leu Ala Ile Leu Ala Ile
1               5                   10                  15
Val Leu Met Gly Ser Val Ala
                20

<210> SEQ ID NO 80
<211> LENGTH: 27
<212> TYPE: PRT
<213> ORGANISM: Methanobrevibacter ruminantium

<400> SEQUENCE: 80

Met Glu Lys Thr Met Lys Ser Lys Leu Phe Ile Leu Leu Ile Ile
1               5                   10                  15
Ser Ile Leu Ile Ser Ile Ser Ser Val Ser Ala
                20                  25

<210> SEQ ID NO 81
<211> LENGTH: 23
<212> TYPE: PRT
<213> ORGANISM: Methanobrevibacter ruminantium

<400> SEQUENCE: 81

Met Asp Lys Lys Ile Phe Ile Val Ser Phe Ile Leu Leu Ala Ile Phe
1               5                   10                  15
Thr Ile Gly Ala Val Gly Ala
                20

```
<210> SEQ ID NO 82
<211> LENGTH: 27
<212> TYPE: PRT
<213> ORGANISM: Methanobrevibacter ruminantium

<400> SEQUENCE: 82

Met Met Lys Met Thr Lys Lys Asn Leu Phe Leu Ile Ser Leu Ile Leu
1               5                   10                  15

Leu Ile Ile Leu Thr Ile Gly Ala Val Ser Ala
            20                  25

<210> SEQ ID NO 83
<211> LENGTH: 27
<212> TYPE: PRT
<213> ORGANISM: Methanobrevibacter ruminantium

<400> SEQUENCE: 83

Met Val Ile Met Asn Asn Lys Lys Leu Phe Ile Val Ser Leu Ile Ile
1               5                   10                  15

Leu Thr Ile Leu Thr Ile Gly Ala Val Ser Ala
            20                  25

<210> SEQ ID NO 84
<211> LENGTH: 27
<212> TYPE: PRT
<213> ORGANISM: Methanobrevibacter ruminantium

<400> SEQUENCE: 84

Met Lys Phe Asn Lys Asn Arg Gly Ile Ser Ala Ile Ser Ile Ile Leu
1               5                   10                  15

Ile Leu Phe Leu Ser Ile Ser Met Ala Ser Ala
            20                  25

<210> SEQ ID NO 85
<211> LENGTH: 30
<212> TYPE: PRT
<213> ORGANISM: Methanobrevibacter ruminantium

<400> SEQUENCE: 85

Val Phe Ile Leu Lys Phe Glu Ile Lys Arg Ser Leu Ile Phe Ile Ser
1               5                   10                  15

Ile Leu Ala Ile Leu Ile Leu Ser Ile Gly Met Ala Ser Ala
            20                  25                  30

<210> SEQ ID NO 86
<211> LENGTH: 42
<212> TYPE: PRT
<213> ORGANISM: Methanobrevibacter ruminantium

<400> SEQUENCE: 86

Met Gln Ala Ile Ile Pro Val Lys Asp Asn Phe Leu Ile Leu Val Thr
1               5                   10                  15

Asn Met Lys Lys Ser Asp Phe Lys Arg Ile Phe Ile Cys Leu Val Leu
            20                  25                  30

Leu Thr Cys Leu Ile Gly Ala Val Ser Ala
        35                  40

<210> SEQ ID NO 87
<211> LENGTH: 26
<212> TYPE: PRT
<213> ORGANISM: Methanobrevibacter ruminantium

<400> SEQUENCE: 87
```

Met Asn Phe Lys Lys Leu Leu Met Ile Ser Leu Ile Leu Phe Val
1               5                   10                  15

Leu Ser Val Gly Phe Ser Thr Ala Ser Ala
            20                  25

<210> SEQ ID NO 88
<211> LENGTH: 24
<212> TYPE: PRT
<213> ORGANISM: Methanobrevibacter ruminantium

<400> SEQUENCE: 88

Met Lys Ile Lys Lys Ser Phe Val Ile Leu Cys Leu Ile Ile Cys Leu
1               5                   10                  15

Phe Thr Ile Ala Ser Val Ala Ala
            20

<210> SEQ ID NO 89
<211> LENGTH: 23
<212> TYPE: PRT
<213> ORGANISM: Methanobrevibacter ruminantium

<400> SEQUENCE: 89

Val Thr Val Ser Val Phe Ile Ser Ala Ser Phe Ala Phe Gly Asn Val
1               5                   10                  15

Leu Ser Asn Ala Asp Asn Gly
            20

<210> SEQ ID NO 90
<211> LENGTH: 22
<212> TYPE: PRT
<213> ORGANISM: Methanobrevibacter ruminantium

<400> SEQUENCE: 90

Met Lys Val Leu Lys Ile Ala Ile Ile Met Leu Ile Leu Ile Ile Ser
1               5                   10                  15

Leu Gly Ala Val Ser Ala
            20

<210> SEQ ID NO 91
<211> LENGTH: 27
<212> TYPE: PRT
<213> ORGANISM: Methanobrevibacter ruminantium

<400> SEQUENCE: 91

Met Asn Phe Lys Thr Lys Gly Ser Leu Ile Leu Ile Ser Leu Leu Phe
1               5                   10                  15

Ile Leu Ile Ile Gly Ile Gly Met Ala Ser Ala
            20                  25

<210> SEQ ID NO 92
<211> LENGTH: 21
<212> TYPE: PRT
<213> ORGANISM: Methanobrevibacter ruminantium

<400> SEQUENCE: 92

Met Gly Lys Phe Lys Phe Ile Phe Ile Leu Val Leu Ala Leu Phe Leu
1               5                   10                  15

Ile Cys Gly Ile Ala
            20

<210> SEQ ID NO 93
<211> LENGTH: 25
<212> TYPE: PRT

-continued

<213> ORGANISM: Methanobrevibacter ruminantium

<400> SEQUENCE: 93

Met Asp Ser Lys Lys Ile Leu Met Ile Ala Val Val Ala Leu Ile Ala
1               5                   10                  15

Ile Val Ala Val Ser Ser Cys Ser Ala
            20                  25

<210> SEQ ID NO 94
<211> LENGTH: 25
<212> TYPE: PRT
<213> ORGANISM: Methanobrevibacter ruminantium

<400> SEQUENCE: 94

Met Lys Leu Lys Ser Lys Tyr Phe Val Phe Leu Leu Ile Ile Cys Ile
1               5                   10                  15

Leu Phe Ser Ile Ser Thr Val Ser Ala
            20                  25

<210> SEQ ID NO 95
<211> LENGTH: 27
<212> TYPE: PRT
<213> ORGANISM: Methanobrevibacter ruminantium

<400> SEQUENCE: 95

Met Asn Tyr Ser Ile Ile Ile Phe Ile Ile Phe Leu Met Asp Ala Leu
1               5                   10                  15

Val Leu Met Ala Ser Ile Gln Val Cys Gly Ala
            20                  25

<210> SEQ ID NO 96
<211> LENGTH: 26
<212> TYPE: PRT
<213> ORGANISM: Methanobrevibacter ruminantium

<400> SEQUENCE: 96

Met Lys Phe Asn Ser Arg Val Leu Gly Ile Leu Ser Leu Leu Phe Val
1               5                   10                  15

Leu Thr Ile Leu Val Ser Ser Val Gly Ala
            20                  25

<210> SEQ ID NO 97
<211> LENGTH: 18
<212> TYPE: PRT
<213> ORGANISM: Methanobrevibacter ruminantium

<400> SEQUENCE: 97

Met Glu Lys Lys Thr Thr Ile Ile Leu Val Ile Leu Ile Ala Leu Ile
1               5                   10                  15

Ala Cys

<210> SEQ ID NO 98
<211> LENGTH: 25
<212> TYPE: PRT
<213> ORGANISM: Methanobrevibacter ruminantium

<400> SEQUENCE: 98

Met Lys Asn Lys Ser Leu Ile Leu Ile Ser Leu Leu Leu Ile Thr
1               5                   10                  15

Ile Ile Ser Ile Gly Ser Val Val Ala
            20                  25

```
<210> SEQ ID NO 99
<211> LENGTH: 23
<212> TYPE: PRT
<213> ORGANISM: Methanobrevibacter ruminantium

<400> SEQUENCE: 99

Met Arg Ser Thr Ile Leu Leu Ser Ala Ser Thr Ala Glu Ser Arg Ser
1               5                   10                  15

Pro Ser Leu Thr Thr Gly Arg
            20

<210> SEQ ID NO 100
<211> LENGTH: 31
<212> TYPE: PRT
<213> ORGANISM: Methanobrevibacter ruminantium

<400> SEQUENCE: 100

Val Leu Leu Ile Cys Phe Ile Gly Leu Val Glu Ala Ile Leu Met Ala
1               5                   10                  15

Leu Val Asp Trp Glu Asp Leu Ala Ile Ser Val Arg Lys Ser Pro
            20                  25                  30

<210> SEQ ID NO 101
<211> LENGTH: 24
<212> TYPE: PRT
<213> ORGANISM: Methanobrevibacter ruminantium

<400> SEQUENCE: 101

Met Asn Lys Lys Ile Ile Leu Ser Leu Leu Val Leu Leu Val Leu Ala
1               5                   10                  15

Ile Ser Val Ser Ala Val Ala Ala
            20

<210> SEQ ID NO 102
<211> LENGTH: 37
<212> TYPE: PRT
<213> ORGANISM: Methanobrevibacter ruminantium

<400> SEQUENCE: 102

Met Ser Leu Ser Ile Phe Val Leu Val Ile Gly Gly Gly Phe Ile Asn
1               5                   10                  15

Lys Arg Ile Leu Leu Ile Phe Val Phe Leu Ile Phe Phe Ile Ser Ile
            20                  25                  30

Gly Ser Val Val Ala
        35

<210> SEQ ID NO 103
<211> LENGTH: 25
<212> TYPE: PRT
<213> ORGANISM: Methanobrevibacter ruminantium

<400> SEQUENCE: 103

Met Asn Asn Lys Lys Ile Ile Met Ser Phe Leu Leu Val Leu Leu Ile
1               5                   10                  15

Ala Ile Ser Val Ser Ala Val Ser Ala
            20                  25

<210> SEQ ID NO 104
<211> LENGTH: 25
<212> TYPE: PRT
<213> ORGANISM: Methanobrevibacter ruminantium

<400> SEQUENCE: 104
```

```
Met Lys Ile Gln Arg Gly Ile Tyr Ile Ile Leu Thr Leu Leu Val Leu
1               5                   10                  15

Phe Ser Leu Ser Ala Ala Ser Ala Ala
            20                  25
```

<210> SEQ ID NO 105
<211> LENGTH: 30
<212> TYPE: PRT
<213> ORGANISM: Methanobrevibacter ruminantium

<400> SEQUENCE: 105

```
Met Glu Leu Lys Val Asp Gln Asp Lys Cys Leu Gly Cys Gly Val Cys
1               5                   10                  15

Val Ile Ala Cys Pro Val Asn Ala Ser Ile Ser Pro Glu Asn
            20                  25                  30
```

<210> SEQ ID NO 106
<211> LENGTH: 17
<212> TYPE: PRT
<213> ORGANISM: Methanobrevibacter ruminantium

<400> SEQUENCE: 106

```
Met Asn Arg Arg Ser Lys Leu Ile Ile Ala Ile Leu Ile Val Ile Ile
1               5                   10                  15

Ile
```

<210> SEQ ID NO 107
<211> LENGTH: 20
<212> TYPE: PRT
<213> ORGANISM: Methanobrevibacter ruminantium

<400> SEQUENCE: 107

```
Met Lys Arg Ser Lys Lys Leu Ile Ile Ala Ile Leu Val Val Ile Leu
1               5                   10                  15

Leu Gly Leu Leu
            20
```

<210> SEQ ID NO 108
<211> LENGTH: 35
<212> TYPE: PRT
<213> ORGANISM: Methanobrevibacter ruminantium

<400> SEQUENCE: 108

```
Met Lys Glu Tyr Lys Ile Ala Ile Ile Gly Gly Gly Pro Ala Gly Met
1               5                   10                  15

Ile Ala Ala Ile Arg Ala Ala Glu Ile Leu Gly Pro Asn Ala Val Cys
            20                  25                  30

Ile Leu Glu
        35
```

<210> SEQ ID NO 109
<211> LENGTH: 25
<212> TYPE: PRT
<213> ORGANISM: Methanobrevibacter ruminantium

<400> SEQUENCE: 109

```
Met Ala Asn Glu Gly Gly Gly His Leu Lys Thr Ile Leu Met Ile Ile
1               5                   10                  15

Ile Leu Ile Ala Phe Ile Cys Gly Leu
            20                  25
```

<210> SEQ ID NO 110

```
<211> LENGTH: 29
<212> TYPE: PRT
<213> ORGANISM: Methanobrevibacter ruminantium

<400> SEQUENCE: 110

Met Asp Asn Lys Ile Lys Ala Gly Ile Ala Leu Ala Ile Ile Val Leu
1               5                   10                  15

Val Ala Val Ile Gly Phe Ser Phe Ile Asn Glu Ser Asn
            20                  25

<210> SEQ ID NO 111
<211> LENGTH: 25
<212> TYPE: PRT
<213> ORGANISM: Methanobrevibacter ruminantium

<400> SEQUENCE: 111

Met Phe Lys Val Ser Lys Ser Ile Leu Ile Val Cys Leu Val Ser Leu
1               5                   10                  15

Phe Leu Leu Val Ser Gln Ala Ser Ala
            20                  25

<210> SEQ ID NO 112
<211> LENGTH: 25
<212> TYPE: PRT
<213> ORGANISM: Methanobrevibacter ruminantium

<400> SEQUENCE: 112

Met Trp Tyr Asp Met Lys Arg Arg Phe Tyr Leu Ile Leu Phe Ile
1               5                   10                  15

Ile Leu Leu Ile Leu Ala Ala Ile Ala
            20                  25

<210> SEQ ID NO 113
<211> LENGTH: 27
<212> TYPE: PRT
<213> ORGANISM: Methanobrevibacter ruminantium

<400> SEQUENCE: 113

Met Lys Ile Thr Val Ala Gly Val Gly Tyr Val Gly Leu Ser Leu Ala
1               5                   10                  15

Val Leu Leu Ala Gln Lys His Asp Val Thr Ala
            20                  25

<210> SEQ ID NO 114
<211> LENGTH: 30
<212> TYPE: PRT
<213> ORGANISM: Methanobrevibacter ruminantium

<400> SEQUENCE: 114

Met Asn Leu Met Lys Ile Thr Val Ala Gly Val Gly Tyr Val Gly Leu
1               5                   10                  15

Ser Ile Ala Ile Leu Leu Ala Gln Lys His Asp Val Thr Ala
            20                  25                  30

<210> SEQ ID NO 115
<211> LENGTH: 27
<212> TYPE: PRT
<213> ORGANISM: Methanobrevibacter ruminantium

<400> SEQUENCE: 115

Met Glu Ile Arg Tyr Lys Asn Leu Leu Lys Val Phe Thr Ile Phe Leu
1               5                   10                  15

Val Leu Leu Ile Ser Cys Gly Phe Ala Ser Ala
```

-continued

<210> SEQ ID NO 116
<211> LENGTH: 27
<212> TYPE: PRT
<213> ORGANISM: Methanobrevibacter ruminantium

<400> SEQUENCE: 116

Met Lys Ile Arg Tyr Lys Asn Leu Leu Lys Val Phe Thr Ile Phe Leu
1               5                   10                  15

Val Leu Leu Ile Ser Cys Gly Phe Ala Ser Ala
            20                  25

<210> SEQ ID NO 117
<211> LENGTH: 16
<212> TYPE: PRT
<213> ORGANISM: Methanobrevibacter ruminantium

<400> SEQUENCE: 117

Lys Lys Leu Ile Ile Ile Leu Leu Leu Ile Leu Leu Leu Ser Ile
1               5                   10                  15

<210> SEQ ID NO 118
<211> LENGTH: 17
<212> TYPE: PRT
<213> ORGANISM: Methanobrevibacter ruminantium

<400> SEQUENCE: 118

Lys Lys Lys Leu Ile Ile Ile Leu Leu Leu Leu Ile Leu Leu Leu Ser
1               5                   10                  15

Ile

<210> SEQ ID NO 119
<211> LENGTH: 17
<212> TYPE: PRT
<213> ORGANISM: Methanobrevibacter ruminantium

<400> SEQUENCE: 119

Lys Lys Ile Ile Ile Ile Leu Leu Leu Ile Leu Leu Leu Ile Ser
1               5                   10                  15

Ile

<210> SEQ ID NO 120
<211> LENGTH: 23
<212> TYPE: PRT
<213> ORGANISM: Methanobrevibacter ruminantium

<400> SEQUENCE: 120

Met Gln Arg Ser Leu Phe Asp Lys Val Lys Thr Ser Leu Trp Met Leu
1               5                   10                  15

Pro Ser Phe Phe Gly Leu Val
            20

<210> SEQ ID NO 121
<211> LENGTH: 27
<212> TYPE: PRT
<213> ORGANISM: Methanobrevibacter ruminantium

<400> SEQUENCE: 121

Met Lys Phe Lys Asn Ser His Ile Leu Leu Val Ser Leu Ile Ser Ile
1               5                   10                  15

Phe Leu Leu Leu Ser Ile Ser Ala Ala Ser Ala
            20                  25

<210> SEQ ID NO 122
<211> LENGTH: 25
<212> TYPE: PRT
<213> ORGANISM: Methanobrevibacter ruminantium

<400> SEQUENCE: 122

Met Asn Ser Lys Lys Ile Ala Ile Val Leu Gly Ile Ile Leu Leu Ser
1               5                   10                  15

Phe Ala Ile Val Gly Ser Ala Ser Ala
            20                  25

<210> SEQ ID NO 123
<211> LENGTH: 39
<212> TYPE: PRT
<213> ORGANISM: Methanobrevibacter ruminantium

<400> SEQUENCE: 123

Met Asp Glu Cys Lys Leu Val Leu Ile Gly Phe Gly Ala Val Gly Gln
1               5                   10                  15

Gly Val Ala Arg Ala Ile Ser Met Lys Lys Glu Met Ile Asn Glu Lys
            20                  25                  30

Phe Gly Ile Ser Leu Lys Val
        35

<210> SEQ ID NO 124
<211> LENGTH: 24
<212> TYPE: PRT
<213> ORGANISM: Methanobrevibacter ruminantium

<400> SEQUENCE: 124

Met Met Arg Lys Thr Ile Phe Gly Val Ile Phe Ile Val Phe Ile Leu
1               5                   10                  15

Phe Ser Ile Ser Thr Val Ser Ala
            20

<210> SEQ ID NO 125
<211> LENGTH: 23
<212> TYPE: PRT
<213> ORGANISM: Methanobrevibacter ruminantium

<400> SEQUENCE: 125

Met Asn Lys Gln Asn Val Phe Ala Leu Ile Leu Leu Thr Ile Ile Leu
1               5                   10                  15

Leu Ser Val Val Ala Val Ser
            20

<210> SEQ ID NO 126
<211> LENGTH: 25
<212> TYPE: PRT
<213> ORGANISM: Methanobrevibacter ruminantium

<400> SEQUENCE: 126

Met Leu Asn Lys Lys Ile Ile Ile Ile Leu Thr Phe Ile Leu Ile Leu
1               5                   10                  15

Ser Ile Ser Ser Ala Ser Ala Ser Ala
            20                  25

<210> SEQ ID NO 127
<211> LENGTH: 22
<212> TYPE: PRT
<213> ORGANISM: Methanobrevibacter ruminantium -continued

```
<400> SEQUENCE: 127

Met Gly Val Leu Ala Ser Val Ala Gly Gly Ile Phe Phe Glu Ala Gly
1               5                   10                  15

Met Ile Ala Thr Cys Thr
            20

<210> SEQ ID NO 128
<211> LENGTH: 33
<212> TYPE: PRT
<213> ORGANISM: Methanobrevibacter ruminantium

<400> SEQUENCE: 128

Val Phe Ser Val Ser Leu Asn Lys Leu Lys Ile Gly Arg Val Phe Ile
1               5                   10                  15

Cys Leu Phe Ile Leu Val Phe Ile Ser Cys Ser Ile Asn Cys Val Phe
            20                  25                  30

Ala

<210> SEQ ID NO 129
<211> LENGTH: 18
<212> TYPE: PRT
<213> ORGANISM: Methanobrevibacter ruminantium

<400> SEQUENCE: 129

Met Gly Gly Glu Ile Ile Asn Asn Glu Lys Leu Lys Leu Ile Leu Ile
1               5                   10                  15

Leu Thr

<210> SEQ ID NO 130
<211> LENGTH: 29
<212> TYPE: PRT
<213> ORGANISM: Methanobrevibacter ruminantium

<400> SEQUENCE: 130

Met Asp Lys Lys Met Ile Val Ser Val Ala Phe Leu Leu Leu Ile Leu
1               5                   10                  15

Ala Val Ala Leu Val Ser Val Phe Asp Glu Ser Asn Ser
            20                  25

<210> SEQ ID NO 131
<211> LENGTH: 22
<212> TYPE: PRT
<213> ORGANISM: Methanobrevibacter ruminantium

<400> SEQUENCE: 131

Met Lys Ile Ser Arg Ile Ile Val Leu Leu Met Ile Leu Ile Phe Thr
1               5                   10                  15

Ala Gly Met Val Tyr Ala
            20

<210> SEQ ID NO 132
<211> LENGTH: 25
<212> TYPE: PRT
<213> ORGANISM: Methanobrevibacter ruminantium

<400> SEQUENCE: 132

Met Asp Ser Lys Lys Ile Leu Val Ile Leu Gly Leu Thr Val Leu Ala
1               5                   10                  15

Ile Phe Leu Ala Ser Ser Val Ser Ala
            20                  25
```

```
<210> SEQ ID NO 133
<211> LENGTH: 33
<212> TYPE: PRT
<213> ORGANISM: Methanobrevibacter ruminantium

<400> SEQUENCE: 133

Met Lys Pro Tyr Val Ile Leu Ile Gly Ser Ala Ser Gly Ile Gly Lys
1               5                   10                  15

Ser Thr Val Ala Ala Glu Leu Ala Lys Thr Leu Asn Ile Lys His Leu
            20                  25                  30

Val

<210> SEQ ID NO 134
<211> LENGTH: 18
<212> TYPE: PRT
<213> ORGANISM: Methanobrevibacter ruminantium

<400> SEQUENCE: 134

Met Leu Ile Ser Val Leu Gly Val Ile Val Ile Ile Met Val Val
1               5                   10                  15

Ala Ala

<210> SEQ ID NO 135
<211> LENGTH: 21
<212> TYPE: PRT
<213> ORGANISM: Methanobrevibacter ruminantium

<400> SEQUENCE: 135

Met Ala Thr Arg Thr Lys Gln Thr Ile Cys Arg Leu Tyr Ser Phe His
1               5                   10                  15

Gly Gly Arg Phe Leu
            20

<210> SEQ ID NO 136
<211> LENGTH: 21
<212> TYPE: PRT
<213> ORGANISM: Methanobrevibacter ruminantium

<400> SEQUENCE: 136

Met Glu Leu Ser Lys Ser Asp Lys Tyr Leu Ile Val Val Gly Ile Ile
1               5                   10                  15

Phe Cys Leu Ala Leu
            20

<210> SEQ ID NO 137
<211> LENGTH: 22
<212> TYPE: PRT
<213> ORGANISM: Methanobrevibacter ruminantium

<400> SEQUENCE: 137

Met Lys Val Ala Ile Leu Gly Ala Gly Cys Tyr Arg Thr His Ala Ala
1               5                   10                  15

Ser Gly Ile Thr Asn Phe
            20

<210> SEQ ID NO 138
<211> LENGTH: 16
<212> TYPE: PRT
<213> ORGANISM: Methanobrevibacter ruminantium

<400> SEQUENCE: 138

Leu Ser Val Ile Leu Ile Leu Phe Leu Ala Val Ser Thr Val Ala Ala
1               5                   10                  15
```

<210> SEQ ID NO 139
<211> LENGTH: 16
<212> TYPE: PRT
<213> ORGANISM: Methanobrevibacter ruminantium

<400> SEQUENCE: 139

Met Asn Lys Lys Leu Lys Ile Ile Leu Tyr Ile Leu Leu Ala Leu Ile
1               5                   10                  15

<210> SEQ ID NO 140
<211> LENGTH: 31
<212> TYPE: PRT
<213> ORGANISM: Methanobrevibacter ruminantium

<400> SEQUENCE: 140

Met Glu Thr Lys Asn Leu Ile Ile Ile Cys Ala Thr Val Ile Leu Ala
1               5                   10                  15

Val Val Ile Val Leu Ser Ala Phe Ile Tyr Val Asn Met Gly Asn
            20                  25                  30

<210> SEQ ID NO 141
<211> LENGTH: 21
<212> TYPE: PRT
<213> ORGANISM: Methanobrevibacter ruminantium

<400> SEQUENCE: 141

Val Leu Val Leu Ala Phe Ala Ile Ile Phe Leu Gly Tyr Ser Ile Ser
1               5                   10                  15

Leu Gly Asn Asn Gln
            20

<210> SEQ ID NO 142
<211> LENGTH: 22
<212> TYPE: PRT
<213> ORGANISM: Methanobrevibacter ruminantium

<400> SEQUENCE: 142

Met Glu Leu Asn Asp Glu Ile Ile Phe Lys Val Ala Leu Ile Thr Ala
1               5                   10                  15

Leu Val Gly Met Ile Gly
            20

<210> SEQ ID NO 143
<211> LENGTH: 25
<212> TYPE: PRT
<213> ORGANISM: Methanobrevibacter ruminantium

<400> SEQUENCE: 143

Met Lys Asn Tyr Phe Asp Ile Lys Asp Lys Val Ala Val Thr Gly
1               5                   10                  15

Ala Ser Ser Gly Leu Gly Trp Gln Ile
            20                  25

<210> SEQ ID NO 144
<211> LENGTH: 32
<212> TYPE: PRT
<213> ORGANISM: Methanobrevibacter ruminantium

<400> SEQUENCE: 144

Leu Thr Phe Asn Asn Leu Arg Ile Asn Ile Lys Asp Cys Met Val Ile
1               5                   10                  15

Phe Val Val Phe Thr Val Leu Leu Leu Ser Ile Leu Ala Val Ser Ala

```
              20                  25                  30

<210> SEQ ID NO 145
<211> LENGTH: 24
<212> TYPE: PRT
<213> ORGANISM: Methanobrevibacter ruminantium

<400> SEQUENCE: 145

Met Lys Phe Lys Lys Tyr Leu Phe Ile Leu Leu Ile Ala Leu Ile Cys
1               5                   10                  15

Ile Ile Ser Val Ser Ala Val Ala
            20

<210> SEQ ID NO 146
<211> LENGTH: 20
<212> TYPE: PRT
<213> ORGANISM: Methanobrevibacter ruminantium

<400> SEQUENCE: 146

Met Asp Lys Lys Met Thr Val Leu Leu Val Ala Leu Phe Cys Leu Leu
1               5                   10                  15

Cys Val Gly Ser
            20

<210> SEQ ID NO 147
<211> LENGTH: 28
<212> TYPE: PRT
<213> ORGANISM: Methanobrevibacter ruminantium

<400> SEQUENCE: 147

Met Asp Arg Lys Asp Ile Ile Ile Ile Ile Leu Val Leu Ile Ile Ile
1               5                   10                  15

Ser Leu Leu Ala Leu Gly Leu His Asn His Gln Val
            20                  25

<210> SEQ ID NO 148
<211> LENGTH: 27
<212> TYPE: PRT
<213> ORGANISM: Methanobrevibacter ruminantium

<400> SEQUENCE: 148

Met Thr Ser Glu Ile Met Ile Leu Thr Pro Thr Ala Val Val Leu Ala
1               5                   10                  15

Ala Asp Ser Ala Val Thr Ile Ser Asp Ile Lys
            20                  25

<210> SEQ ID NO 149
<211> LENGTH: 23
<212> TYPE: PRT
<213> ORGANISM: Methanobrevibacter ruminantium

<400> SEQUENCE: 149

Met Arg Lys Lys Ile Leu Phe Leu Thr Leu Met Ile Leu Ile Cys Phe
1               5                   10                  15

Thr Leu Asn Ser Val Cys Ala
            20

<210> SEQ ID NO 150
<211> LENGTH: 23
<212> TYPE: PRT
<213> ORGANISM: Methanobrevibacter ruminantium

<400> SEQUENCE: 150
```

```
Met Arg Leu Arg Tyr Phe Ala Ile Ile Ser Leu Ile Leu Leu Ile Phe
1               5                   10                  15

Leu Val Pro Val Ser Phe Ala
            20
```

<210> SEQ ID NO 151
<211> LENGTH: 18
<212> TYPE: PRT
<213> ORGANISM: Methanobrevibacter ruminantium

<400> SEQUENCE: 151

```
Met Phe Ile Gly Leu Leu Ile Gly Leu Leu Ile Ile Pro Ile Ser
1               5                   10                  15

Phe Ala
```

<210> SEQ ID NO 152
<211> LENGTH: 24
<212> TYPE: PRT
<213> ORGANISM: Methanobrevibacter ruminantium

<400> SEQUENCE: 152

```
Leu Leu Ile Gly Leu Val Ile Cys Ala Gly Val Phe Tyr Phe Gln Phe
1               5                   10                  15

Asn Tyr Ala Thr Pro Thr Tyr Leu
            20
```

<210> SEQ ID NO 153
<211> LENGTH: 25
<212> TYPE: PRT
<213> ORGANISM: Methanobrevibacter ruminantium

<400> SEQUENCE: 153

```
Val Val Leu Val Ala Val Val Ile Gly Ser Thr Ala Phe Leu Leu
1               5                   10                  15

Asn Tyr Asp Glu Thr Val Lys Tyr Thr
            20                  25
```

<210> SEQ ID NO 154
<211> LENGTH: 20
<212> TYPE: PRT
<213> ORGANISM: Methanobrevibacter ruminantium

<400> SEQUENCE: 154

```
Met Asp Lys Lys Thr Leu Ala Ile Ile Ala Ile Ile Val Ile Ala Leu
1               5                   10                  15

Val Ala Val Gly
            20
```

<210> SEQ ID NO 155
<211> LENGTH: 24
<212> TYPE: PRT
<213> ORGANISM: Methanobrevibacter ruminantium

<400> SEQUENCE: 155

```
Met Asn Asn Lys Thr Leu Phe Ile Ile Gly Leu Phe Ile Cys Leu Leu
1               5                   10                  15

Phe Thr Ile Pro Met Val Ser Ala
            20
```

<210> SEQ ID NO 156
<211> LENGTH: 20
<212> TYPE: PRT
<213> ORGANISM: Methanobrevibacter ruminantium

```
<400> SEQUENCE: 156

Met Ile Lys Thr Asp Asn Lys Gly Gln Ile Thr Val Glu Leu Leu Leu
1               5                   10                  15

Leu Leu Ser Phe
            20

<210> SEQ ID NO 157
<211> LENGTH: 24
<212> TYPE: PRT
<213> ORGANISM: Methanobrevibacter ruminantium

<400> SEQUENCE: 157

Met Leu Asn Arg Lys Ala Leu Ile Phe Ser Leu Ile Val Leu Phe Met
1               5                   10                  15

Leu Ser Ile Ser Ala Val Ser Ala
            20

<210> SEQ ID NO 158
<211> LENGTH: 23
<212> TYPE: PRT
<213> ORGANISM: Methanobrevibacter ruminantium

<400> SEQUENCE: 158

Met Asp Asn Lys Ala Ile Ile Gly Ile Val Ile Ala Leu Ile Val Ile
1               5                   10                  15

Val Leu Ala Cys Phe Ala Tyr
            20

<210> SEQ ID NO 159
<211> LENGTH: 30
<212> TYPE: PRT
<213> ORGANISM: Methanobrevibacter ruminantium

<400> SEQUENCE: 159

Met Ser Tyr Phe Asn Lys Gly His Ile Trp Asn Ile Leu Leu Ile Cys
1               5                   10                  15

Leu Leu Ile Gly Thr Leu Ala Met Met Gly Ser Ala Ser Ala
            20                  25                  30

<210> SEQ ID NO 160
<211> LENGTH: 31
<212> TYPE: PRT
<213> ORGANISM: Methanobrevibacter ruminantium

<400> SEQUENCE: 160

Met Lys Asn Lys Ala Met Phe Leu Ile Ser Ala Leu Leu Ile Ala Val
1               5                   10                  15

Ile Leu Ser Leu Ser Ala Val Ser Ala Ala Asp Asp Ala Ile Ala
            20                  25                  30

<210> SEQ ID NO 161
<211> LENGTH: 25
<212> TYPE: PRT
<213> ORGANISM: Methanobrevibacter ruminantium

<400> SEQUENCE: 161

Met Lys Phe Asn Lys Ser Leu Ile Ala Ile Phe Val Ile Leu Ile Val
1               5                   10                  15

Ala Phe Ser Ser Ile Ser Val Ile Ala
            20                  25
```

```
<210> SEQ ID NO 162
<211> LENGTH: 20
<212> TYPE: PRT
<213> ORGANISM: Methanobrevibacter ruminantium

<400> SEQUENCE: 162

Met Asp Lys Lys Ile Ile Ile Gly Ala Val Val Ala Leu Leu Val Ile
1               5                   10                  15

Ile Val Gly Ala
            20

<210> SEQ ID NO 163
<211> LENGTH: 16
<212> TYPE: PRT
<213> ORGANISM: Methanobrevibacter ruminantium

<400> SEQUENCE: 163

Val Glu Gly Asp Asn Met Val Asn Ile Lys Thr Val Ala Leu Ala Val
1               5                   10                  15

<210> SEQ ID NO 164
<211> LENGTH: 26
<212> TYPE: PRT
<213> ORGANISM: Methanobrevibacter ruminantium

<400> SEQUENCE: 164

Met Leu Ile Met Ala Ile Leu Val Leu Leu Thr Met Ala Ser Val Ser
1               5                   10                  15

Ala Ser Glu Leu Glu Asp Ile Gln Val Thr
            20                  25

<210> SEQ ID NO 165
<211> LENGTH: 16
<212> TYPE: PRT
<213> ORGANISM: Methanobrevibacter ruminantium

<400> SEQUENCE: 165

Met Asn Asn Thr Thr Lys Ile Leu Ile Gly Val Leu Met Gly Leu Leu
1               5                   10                  15

<210> SEQ ID NO 166
<211> LENGTH: 21
<212> TYPE: PRT
<213> ORGANISM: Methanobrevibacter ruminantium

<400> SEQUENCE: 166

Met Glu Thr Glu Asn Leu Ile Ile Val Ile Leu Leu Val Leu Ile Ala
1               5                   10                  15

Met Ala Gly Ile Phe
            20

<210> SEQ ID NO 167
<211> LENGTH: 21
<212> TYPE: PRT
<213> ORGANISM: Methanobrevibacter ruminantium

<400> SEQUENCE: 167

Met Phe Leu Val Ile Leu Leu Phe Ala Phe Ile Val Ile Gly Gly Ser
1               5                   10                  15

Tyr Ser Val Phe Ala
            20

<210> SEQ ID NO 168
<211> LENGTH: 38
```

```
<212> TYPE: PRT
<213> ORGANISM: Methanobrevibacter ruminantium

<400> SEQUENCE: 168

Met Ala Leu Leu Ile Leu Ala Met Ser Cys Val Ser Ala Ser Asn Ala
1               5                   10                  15

Ser Asp Asn Leu Asp Asp Leu Thr Ile Ser Asp Ser Asn Ser Leu Asp
            20                  25                  30

Leu Val Ser Thr Ser Asn
            35

<210> SEQ ID NO 169
<211> LENGTH: 16
<212> TYPE: PRT
<213> ORGANISM: Methanobrevibacter ruminantium

<400> SEQUENCE: 169

Met Asn Asn Lys Tyr Phe Leu Gly Ile Ile Ile Ile Ile Ile Ala Val
1               5                   10                  15

<210> SEQ ID NO 170
<211> LENGTH: 31
<212> TYPE: PRT
<213> ORGANISM: Methanobrevibacter ruminantium

<400> SEQUENCE: 170

Met Leu Leu Asn Asp Lys Ser Glu Leu Leu Lys Ser Leu Ser Ile Leu
1               5                   10                  15

Phe Leu Leu Ile Val Leu Ile Thr Ser Phe Asn Ser Val Tyr Ala
            20                  25                  30

<210> SEQ ID NO 171
<211> LENGTH: 20
<212> TYPE: PRT
<213> ORGANISM: Methanobrevibacter ruminantium

<400> SEQUENCE: 171

Met Lys Lys Ile Ile Leu Gly Thr Cys Ile Leu Phe Leu Leu Ile Ser
1               5                   10                  15

Val Ala Tyr Ala
            20

<210> SEQ ID NO 172
<211> LENGTH: 27
<212> TYPE: PRT
<213> ORGANISM: Methanobrevibacter ruminantium

<400> SEQUENCE: 172

Met Lys Ile Asn Leu Lys Arg Val Ile Leu Gly Ile Ile Leu Ile Leu
1               5                   10                  15

Ile Cys Ile Ser Ser Ala Ser Ile Ile Ser Ala
            20                  25

<210> SEQ ID NO 173
<211> LENGTH: 54
<212> TYPE: DNA
<213> ORGANISM: Methanobrevibacter ruminantium

<400> SEQUENCE: 173
atggtccttg ccttaagcat aatcctactc agttcaattg cagcagcatc tgca        54

<210> SEQ ID NO 174
<211> LENGTH: 54
```

```
<212> TYPE: DNA
<213> ORGANISM: Methanobrevibacter ruminantium

<400> SEQUENCE: 174
atgagtactt ttattttagt cataataata cttggtatta ttttaataat cgca            54

<210> SEQ ID NO 175
<211> LENGTH: 71
<212> TYPE: DNA
<213> ORGANISM: Methanobrevibacter ruminantium

<400> SEQUENCE: 175
atggataata aaaaaatatt tgttattgta gctttggctc ttttagctat cgttgcagta      60
ggatctgtta g                                                           71

<210> SEQ ID NO 176
<211> LENGTH: 75
<212> TYPE: DNA
<213> ORGANISM: Methanobrevibacter ruminantium

<400> SEQUENCE: 176
atgaacaata aaaaaatatt tgccattgca gctttagcca ttatagctat cgtagcagta      60
ggatcagtca gtgct                                                       75

<210> SEQ ID NO 177
<211> LENGTH: 75
<212> TYPE: DNA
<213> ORGANISM: Methanobrevibacter ruminantium

<400> SEQUENCE: 177
atgaatgcta aaaactaac tattctagca gccttagcta ttctcgctat cgttgcagta       60
ggctcagtaa gtgct                                                       75

<210> SEQ ID NO 178
<211> LENGTH: 66
<212> TYPE: DNA
<213> ORGANISM: Methanobrevibacter ruminantium

<400> SEQUENCE: 178
atgatttgct gtgttttatt aacattttca actgttagtg caattgatat ggatggaaat      60
ctaact                                                                 66

<210> SEQ ID NO 179
<211> LENGTH: 48
<212> TYPE: DNA
<213> ORGANISM: Methanobrevibacter ruminantium

<400> SEQUENCE: 179
atgattattg ccataatctt catgtataat agggtccgca ataagaga                   48

<210> SEQ ID NO 180
<211> LENGTH: 75
<212> TYPE: DNA
<213> ORGANISM: Methanobrevibacter ruminantium

<400> SEQUENCE: 180
atgaataagg ttcaattgtc ctccatactt gctttagtat taatattatt cttgtctttg      60
gctgtagtta gtgca                                                       75

<210> SEQ ID NO 181
<211> LENGTH: 72
```

```
<212> TYPE: DNA
<213> ORGANISM: Methanobrevibacter ruminantium

<400> SEQUENCE: 181
atgagaaaag aaataatttc tatattggta attgctatta tagcaatctc agttattcca    60 actgccttt ca                                                         72

<210> SEQ ID NO 182
<211> LENGTH: 90
<212> TYPE: DNA
<213> ORGANISM: Methanobrevibacter ruminantium

<400> SEQUENCE: 182
atgaataaaa aaagatttaa attattatta actattttta tagcatttgc actcattaac    60
acttgtttta ttttaaatga taatctctca                                     90

<210> SEQ ID NO 183
<211> LENGTH: 66
<212> TYPE: DNA
<213> ORGANISM: Methanobrevibacter ruminantium

<400> SEQUENCE: 183
atgatggtca ttctactaat aacactcctt tctgttccta tcctctcact aacaattgat    60
tattca                                                               66

<210> SEQ ID NO 184
<211> LENGTH: 84
<212> TYPE: DNA
<213> ORGANISM: Methanobrevibacter ruminantium

<400> SEQUENCE: 184
atgaatatta atttaaaaaa aatcacattc ttatgtttgg ttttagttct aatcggtttg    60
atctcattta attcaatcag cgct                                           84

<210> SEQ ID NO 185
<211> LENGTH: 66
<212> TYPE: DNA
<213> ORGANISM: Methanobrevibacter ruminantium

<400> SEQUENCE: 185
atgaataatc aaaataagta ttcttgcata gttttagctg gaggcatgag cagaagaatg    60
ggtcag                                                               66

<210> SEQ ID NO 186
<211> LENGTH: 99
<212> TYPE: DNA
<213> ORGANISM: Methanobrevibacter ruminantium

<400> SEQUENCE: 186
atggaagata gaaaagcaaa atttatcgtt tatgtcgttg tatgcttact tgcttttatc    60
tgcagcagca cagtcttctc tatgactggc ggtctttct                           99

<210> SEQ ID NO 187
<211> LENGTH: 69
<212> TYPE: DNA
<213> ORGANISM: Methanobrevibacter ruminantium

<400> SEQUENCE: 187
atgaacatac taatcaatgg aactggagct atcggaatag ggcttggagc atctatgatt    60
tcacaaggt                                                            69
```

<210> SEQ ID NO 188
<211> LENGTH: 81
<212> TYPE: DNA
<213> ORGANISM: Methanobrevibacter ruminantium

<400> SEQUENCE: 188
atgataatag tcactacaat ctgtgttatc ttaattttga tagttctttt ttatggattg    60
ttccctggat tgacaaacag c                                              81

<210> SEQ ID NO 189
<211> LENGTH: 63
<212> TYPE: DNA
<213> ORGANISM: Methanobrevibacter ruminantium

<400> SEQUENCE: 189
atgtctgatg ttggtaaaac tgtaataaca actattatta ctttagtaac tactgcattt    60
ggt                                                                  63

<210> SEQ ID NO 190
<211> LENGTH: 81
<212> TYPE: DNA
<213> ORGANISM: Methanobrevibacter ruminantium

<400> SEQUENCE: 190
ttgaaatcag ataaacgggc taaatttgcc atattcttct caattgcaat ccttgccttg    60
ggactgagca atattgcagc t                                              81

<210> SEQ ID NO 191
<211> LENGTH: 108
<212> TYPE: DNA
<213> ORGANISM: Methanobrevibacter ruminantium

<400> SEQUENCE: 191
atgattaatg aataatgga caagcagaag gttataactg cctttggcat aattctattt     60
ttggcagctg ctttcagtcc gtttgtagtc ttgcctatct taggagtt                108

<210> SEQ ID NO 192
<211> LENGTH: 75
<212> TYPE: DNA
<213> ORGANISM: Methanobrevibacter ruminantium

<400> SEQUENCE: 192
atgtttaata agaagatggt tttagccata agcttattag ctgttatctt tgcatctatg    60
tgcatagttt cagca                                                     75

<210> SEQ ID NO 193
<211> LENGTH: 84
<212> TYPE: DNA
<213> ORGANISM: Methanobrevibacter ruminantium

<400> SEQUENCE: 193
atgaaaacaa atcttaaaaa aacaacaatc atattggcac tgctgatggc cattttaatt    60
ttatcgattg gagccatctc tgca                                           84

<210> SEQ ID NO 194
<211> LENGTH: 78
<212> TYPE: DNA
<213> ORGANISM: Methanobrevibacter ruminantium

<400> SEQUENCE: 194

-continued

```
atgaattcca agggaaaata tcttgtttta tttcttattt taatattatc atttagcata    60
atctctgctt catttgct                                                   78

<210> SEQ ID NO 195
<211> LENGTH: 84
<212> TYPE: DNA
<213> ORGANISM: Methanobrevibacter ruminantium

<400> SEQUENCE: 195
atgaagaaaa atttaagctt aaaaaatatt ttaatttat cattaatctt ccttttgta      60 ttaagcatag gatcttcatt tgca                                            84

<210> SEQ ID NO 196
<211> LENGTH: 72
<212> TYPE: DNA
<213> ORGANISM: Methanobrevibacter ruminantium

<400> SEQUENCE: 196
atgaaaagga atatttattt tattatttta ttagttacac tatttttaat cagtatgagt    60
gttgttagtg ca                                                         72

<210> SEQ ID NO 197
<211> LENGTH: 66
<212> TYPE: DNA
<213> ORGANISM: Methanobrevibacter ruminantium

<400> SEQUENCE: 197
atgaaaaaaa tggaaatggc tagttatatt atcttaattg catctgtatt agctatactt    60
tatgca                                                                66

<210> SEQ ID NO 198
<211> LENGTH: 72
<212> TYPE: DNA
<213> ORGANISM: Methanobrevibacter ruminantium

<400> SEQUENCE: 198
atgcctaaaa ttgcaaaatt atggaataag ctagcagatc caaagaacat tcctaggctg    60
tttgctgtaa tt                                                         72

<210> SEQ ID NO 199
<211> LENGTH: 93
<212> TYPE: DNA
<213> ORGANISM: Methanobrevibacter ruminantium

<400> SEQUENCE: 199
atgtttaatc tggctatttg ggtttattta ggtttggcat tagctatttt tggaagcctc    60
gcaactgtat ggggtcctgg agtaaaggat cca                                  93

<210> SEQ ID NO 200
<211> LENGTH: 62
<212> TYPE: DNA
<213> ORGANISM: Methanobrevibacter ruminantium

<400> SEQUENCE: 200
ttgttcgcta tagtaagcct atctgcagtc agcgcaagcg atgattttc aagttccctt     60 gc                                                                    62

<210> SEQ ID NO 201
<211> LENGTH: 72
```

```
<212> TYPE: DNA
<213> ORGANISM: Methanobrevibacter ruminantium

<400> SEQUENCE: 201
atgaaaagaa gatataaagt tttatttcta ttggccatct aactataat aagcattaat    60 gccatttcag ct                                                       72

<210> SEQ ID NO 202
<211> LENGTH: 39
<212> TYPE: DNA
<213> ORGANISM: Methanobrevibacter ruminantium

<400> SEQUENCE: 202
atgctctttt cagtaattgc tactgtatct gctacttgt                          39

<210> SEQ ID NO 203
<211> LENGTH: 40
<212> TYPE: DNA
<213> ORGANISM: Methanobrevibacter ruminantium

<400> SEQUENCE: 203
atgtttatta aaattagaag agacacttta ataatattat                         40

<210> SEQ ID NO 204
<211> LENGTH: 105
<212> TYPE: DNA
<213> ORGANISM: Methanobrevibacter ruminantium

<400> SEQUENCE: 204
atgaaagcag tcattcctgc agcagggctt ggaacaagat tccttcctgc tactaaagct   60
caaccaaaag agatgttgcc ggtttatgac aagccgacca ttcaa                  105

<210> SEQ ID NO 205
<211> LENGTH: 78
<212> TYPE: DNA
<213> ORGANISM: Methanobrevibacter ruminantium

<400> SEQUENCE: 205
atgattaaaa ctgatgtatt ggttattggt gctggacctg ctggttcttc agctgctaga   60
tttgcagcta aaggcggc                                                 78

<210> SEQ ID NO 206
<211> LENGTH: 87
<212> TYPE: DNA
<213> ORGANISM: Methanobrevibacter ruminantium

<400> SEQUENCE: 206
atggaggata atcttttgaa aaatagaaaa ctaattttga taagtatctt ccttgttagt   60
ctgcttgcaa tttctgctgt aagcgca                                       87

<210> SEQ ID NO 207
<211> LENGTH: 78
<212> TYPE: DNA
<213> ORGANISM: Methanobrevibacter ruminantium

<400> SEQUENCE: 207
atgaacagaa ataaaataat tgttttgctt gtattattga tagcagttgt tggctttaca   60
atggggccag cttgtgca                                                 78

<210> SEQ ID NO 208
<211> LENGTH: 72
```

```
<212> TYPE: DNA
<213> ORGANISM: Methanobrevibacter ruminantium

<400> SEQUENCE: 208
atgaaaaaat cagttttaa aattctaatt gctttagctt taattttatt ggctgtatca    60 attgttcat ct                                                       72

<210> SEQ ID NO 209
<211> LENGTH: 63
<212> TYPE: DNA
<213> ORGANISM: Methanobrevibacter ruminantium

<400> SEQUENCE: 209 atgaaaaga atatttttt aattgcaata atactaattg cagttgttgc agttagtgga    60
tgt                                                                63

<210> SEQ ID NO 210
<211> LENGTH: 66
<212> TYPE: DNA
<213> ORGANISM: Methanobrevibacter ruminantium

<400> SEQUENCE: 210
atgttgattg ccttacttgg cttatctgct gttgcagcag ttgacgctga cccattaact    60
gataat                                                               66

<210> SEQ ID NO 211
<211> LENGTH: 54
<212> TYPE: DNA
<213> ORGANISM: Methanobrevibacter ruminantium

<400> SEQUENCE: 211
atgagcgaaa ataatagaac tttgattaca ataggaatcg gcgcttttat tata          54

<210> SEQ ID NO 212
<211> LENGTH: 93
<212> TYPE: DNA
<213> ORGANISM: Methanobrevibacter ruminantium

<400> SEQUENCE: 212
atgggaaaga tatttaaaat tgttacaatc atattgattg tcattgcatt ggctatactt    60
ggtgttttca tctattctga tggacattct gaa                                 93

<210> SEQ ID NO 213
<211> LENGTH: 48
<212> TYPE: DNA
<213> ORGANISM: Methanobrevibacter ruminantium

<400> SEQUENCE: 213
atggataaga aacaatcat tatagctgca gtagctattc tcgttatt                  48

<210> SEQ ID NO 214
<211> LENGTH: 71
<212> TYPE: DNA
<213> ORGANISM: Methanobrevibacter ruminantium

<400> SEQUENCE: 214
atgaaattaa ataaattctt cattatcagc ataatattga ttatatttct atcaattagt    60
gcaataagtg c                                                         71

<210> SEQ ID NO 215
<211> LENGTH: 72
```

```
<212> TYPE: DNA
<213> ORGANISM: Methanobrevibacter ruminantium

<400> SEQUENCE: 215
atgaagaaaa aaatagcaat tattttagga attgcattat tagcattctt agtcatcggc    60
gcatccagcg ca                                                        72

<210> SEQ ID NO 216
<211> LENGTH: 72
<212> TYPE: DNA
<213> ORGANISM: Methanobrevibacter ruminantium

<400> SEQUENCE: 216
atgaatttca ataaaaaaat tttattaata atagcattgg tattcattgc tagtgttggc    60
attgttgcag ct                                                        72

<210> SEQ ID NO 217
<211> LENGTH: 69
<212> TYPE: DNA
<213> ORGANISM: Methanobrevibacter ruminantium

<400> SEQUENCE: 217
atgaaaagat caatcatatt tttaacaatt atattatcct tattttagt aattggctat     60 gcaagcgct                                                            69

<210> SEQ ID NO 218
<211> LENGTH: 96
<212> TYPE: DNA
<213> ORGANISM: Methanobrevibacter ruminantium

<400> SEQUENCE: 218
gtgggcataa cctttacagc aatcatcaca ggggcattag gtggaactac ttttcagaa     60 cctttaggaa actaccttag ccaattcata ccttac                              96

<210> SEQ ID NO 219
<211> LENGTH: 91
<212> TYPE: DNA
<213> ORGANISM: Methanobrevibacter ruminantium

<400> SEQUENCE: 219
atggattcta aaaaactgat tttagtgact gcattggctt ttttagctat tgtttccata    60
gcttcagtta gtgcatggga cttgtttgga a                                   91

<210> SEQ ID NO 220
<211> LENGTH: 105
<212> TYPE: DNA
<213> ORGANISM: Methanobrevibacter ruminantium

<400> SEQUENCE: 220
atgaatgtga ataagaaaat atttttactt gtaatcttta taatatctat ttcaatagct    60
ggagtatatt gtgcagacat ccatcaggat agcgatttaa ccgca                   105

<210> SEQ ID NO 221
<211> LENGTH: 60
<212> TYPE: DNA
<213> ORGANISM: Methanobrevibacter ruminantium

<400> SEQUENCE: 221
atgatactgg cactattttg ttttatagtc attggctcag caagtgcagc agactttaaa    60
```

```
<210> SEQ ID NO 222
<211> LENGTH: 54
<212> TYPE: DNA
<213> ORGANISM: Methanobrevibacter ruminantium

<400> SEQUENCE: 222
atgatctcac tgcttcttat ttcaattctt gctataagcg cagcaagtgc tgca            54

<210> SEQ ID NO 223
<211> LENGTH: 91
<212> TYPE: DNA
<213> ORGANISM: Methanobrevibacter ruminantium

<400> SEQUENCE: 223
atggaagaaa aaattgcttt agctgcttgc agtggtatga gtccaaatgg tttggttgca      60
agagttgcag ttcatgattt ggctattgac g                                    91

<210> SEQ ID NO 224
<211> LENGTH: 78
<212> TYPE: DNA
<213> ORGANISM: Methanobrevibacter ruminantium

<400> SEQUENCE: 224
atgttaaaaa ctaaattatg cggaattagt ttaaaaaatc cattaatgct tgctgcaggt      60
gttttgggaa gccatgca                                                   78

<210> SEQ ID NO 225
<211> LENGTH: 81
<212> TYPE: DNA
<213> ORGANISM: Methanobrevibacter ruminantium

<400> SEQUENCE: 225
atggaaattg tattatgtgt aacaggcagt gtagctgcag tggaaactgt taagttagct      60
cgtgaattta agcgtcaagg c                                               81

<210> SEQ ID NO 226
<211> LENGTH: 63
<212> TYPE: DNA
<213> ORGANISM: Methanobrevibacter ruminantium

<400> SEQUENCE: 226
atggtagttg caacaataat ctttgcatcc agcttattcg acgcccttta tggatttaaa      60
aac                                                                   63

<210> SEQ ID NO 227
<211> LENGTH: 54
<212> TYPE: DNA
<213> ORGANISM: Methanobrevibacter ruminantium

<400> SEQUENCE: 227
atgatattgg caatattgct tgccgttgga atgacactta ctgcagtaag tgca            54

<210> SEQ ID NO 228
<211> LENGTH: 75
<212> TYPE: DNA
<213> ORGANISM: Methanobrevibacter ruminantium

<400> SEQUENCE: 228
atgaataagc gaatatttct atatatagca ctgattttta ttatttccct gctttctttt      60
tctgcagtca gtgct                                                      75
```

```
<210> SEQ ID NO 229
<211> LENGTH: 69
<212> TYPE: DNA
<213> ORGANISM: Methanobrevibacter ruminantium

<400> SEQUENCE: 229
atgaaatata ataaaaagat attcttttta tttttattat tgtgtctcat aattcctcaa      60
gctatttat                                                              69

<210> SEQ ID NO 230
<211> LENGTH: 75
<212> TYPE: DNA
<213> ORGANISM: Methanobrevibacter ruminantium

<400> SEQUENCE: 230
atgaattcta ataagactta tgcagtatta ggattattgc tcttattaat cttatccata      60
ggcgctatta gtgca                                                       75

<210> SEQ ID NO 231
<211> LENGTH: 81
<212> TYPE: DNA
<213> ORGANISM: Methanobrevibacter ruminantium

<400> SEQUENCE: 231
atgataaata aagaataat tagtcttagt ctgctgatta tattggtctt tctcattatt       60
ggattaagtg cagtcagtgc t                                                81

<210> SEQ ID NO 232
<211> LENGTH: 75
<212> TYPE: DNA
<213> ORGANISM: Methanobrevibacter ruminantium

<400> SEQUENCE: 232
atggatttta aaaagcaat ccctctattt gctttattgc tattgatttt atttattatc       60
ggctcttcaa gcgca                                                       75

<210> SEQ ID NO 233
<211> LENGTH: 75
<212> TYPE: DNA
<213> ORGANISM: Methanobrevibacter ruminantium

<400> SEQUENCE: 233
atgaagctta aaagttttc agtcattta gcggtattgc ttgtagcaat acttgctatt        60
ggggctgtaa gtgca                                                       75

<210> SEQ ID NO 234
<211> LENGTH: 54
<212> TYPE: DNA
<213> ORGANISM: Methanobrevibacter ruminantium

<400> SEQUENCE: 234 atgatttaa tatccttaat tttagttatc ttaagcattt cttgtgtaag tgct             54

<210> SEQ ID NO 235
<211> LENGTH: 66
<212> TYPE: DNA
<213> ORGANISM: Methanobrevibacter ruminantium

<400> SEQUENCE: 235
atggacaact ccaatattat aatctcagta attatagtat tatgtattgc agcaggagta      60
actgca                                                                 66
```

```
<210> SEQ ID NO 236
<211> LENGTH: 66
<212> TYPE: DNA
<213> ORGANISM: Methanobrevibacter ruminantium

<400> SEQUENCE: 236
atggataatt caagcattct tatatccgta atcatcgttt tatgtattgc agcaggagta      60
actgcc                                                                66

<210> SEQ ID NO 237
<211> LENGTH: 66
<212> TYPE: DNA
<213> ORGANISM: Methanobrevibacter ruminantium

<400> SEQUENCE: 237
atgagaaagg aaattttaat tgcagctatt gcaatcatat taatattatg tggaggtgta      60
tttgca                                                                66

<210> SEQ ID NO 238
<211> LENGTH: 54
<212> TYPE: DNA
<213> ORGANISM: Methanobrevibacter ruminantium

<400> SEQUENCE: 238
atgttgatat caattgtact tatatctctc attgctttag gtgcagtaag tgca            54

<210> SEQ ID NO 239
<211> LENGTH: 63
<212> TYPE: DNA
<213> ORGANISM: Methanobrevibacter ruminantium

<400> SEQUENCE: 239
atgaaagaaa ttgctattta tctcatcctt atcataattg ttcttattgc cgcacaacac      60
tta                                                                   63

<210> SEQ ID NO 240
<211> LENGTH: 63
<212> TYPE: DNA
<213> ORGANISM: Methanobrevibacter ruminantium

<400> SEQUENCE: 240
ttgtttgaag caggtatgat tgctcttcct actggtttgc ctggacttgc cttgttgggg      60
ctt                                                                   63

<210> SEQ ID NO 241
<211> LENGTH: 66
<212> TYPE: DNA
<213> ORGANISM: Methanobrevibacter ruminantium

<400> SEQUENCE: 241
atgaaaaact ggaaaataat tggattaata ttaatcatcc ttcttgctgt cgtttcagtt      60
agcggc                                                                66

<210> SEQ ID NO 242
<211> LENGTH: 102
<212> TYPE: DNA
<213> ORGANISM: Methanobrevibacter ruminantium

<400> SEQUENCE: 242
atgagaaata aaaagatttt cattttttact ttaatgattg tcatgctatt atcgcttgct      60
```

```
gcagtttcag caaatgatct ggataatctt gaagttgatg at                   102

<210> SEQ ID NO 243
<211> LENGTH: 83
<212> TYPE: DNA
<213> ORGANISM: Methanobrevibacter ruminantium

<400> SEQUENCE: 243
atgagtatta aacgaatatt acttacgagt ttaatgctat ttataataat attttcaatt    60
tcgtttgtaa gtgcaaatga aaa                                           83

<210> SEQ ID NO 244
<211> LENGTH: 64
<212> TYPE: DNA
<213> ORGANISM: Methanobrevibacter ruminantium

<400> SEQUENCE: 244
atggataagg taggaattat aggagcaggt agtctaggta cagctttagc tcaaacagtg    60
gcta                                                                64

<210> SEQ ID NO 245
<211> LENGTH: 57
<212> TYPE: DNA
<213> ORGANISM: Methanobrevibacter ruminantium

<400> SEQUENCE: 245
ttgatctgta gcatacaggc ctgctcggcc tcatgcactg cagtctatgt agggcct      57

<210> SEQ ID NO 246
<211> LENGTH: 90
<212> TYPE: DNA
<213> ORGANISM: Methanobrevibacter ruminantium

<400> SEQUENCE: 246
atgaaaatat caagaattat acttatatta ttgcttttt g ttgtattttt tgaaatagga    60
ctgttcagct catataccat agtaaatgct                                    90

<210> SEQ ID NO 247
<211> LENGTH: 60
<212> TYPE: DNA
<213> ORGANISM: Methanobrevibacter ruminantium

<400> SEQUENCE: 247
atgattttaa ttatttcact attccttatt tcattactcg ctatcggtgc ggcaagcgca    60

<210> SEQ ID NO 248
<211> LENGTH: 72
<212> TYPE: DNA
<213> ORGANISM: Methanobrevibacter ruminantium

<400> SEQUENCE: 248
atgaaattat ataaaaatag cataatcatt ttattattaa ttttaatttt atcgattgga    60
gcagctgcag ct                                                       72

<210> SEQ ID NO 249
<211> LENGTH: 66
<212> TYPE: DNA
<213> ORGANISM: Methanobrevibacter ruminantium

<400> SEQUENCE: 249
ttggcagtga ttttgataat cctatttca cttggaactg ttgcagcaag tgaaaatata    60
```

-continued

```
gttatt                                                              66

<210> SEQ ID NO 250
<211> LENGTH: 93
<212> TYPE: DNA
<213> ORGANISM: Methanobrevibacter ruminantium

<400> SEQUENCE: 250
atgagaaacc ctaaagatta tattatgaag actgattatt tgattattct tatggcctta   60
ttgctgattt ctatagtttc acctatagca gct                                93

<210> SEQ ID NO 251
<211> LENGTH: 69
<212> TYPE: DNA
<213> ORGANISM: Methanobrevibacter ruminantium

<400> SEQUENCE: 251
atgaataata aaaagatatt tgtggccgga ttagccatat ggctattgt tctaatggga    60 tcagttgct                                                           69

<210> SEQ ID NO 252
<211> LENGTH: 81
<212> TYPE: DNA
<213> ORGANISM: Methanobrevibacter ruminantium

<400> SEQUENCE: 252
atggagaaaa ctatgaaatc taaactttt atacttctaa tcattatctc tattctaata    60
agcatttcat cagtttcagc a                                             81

<210> SEQ ID NO 253
<211> LENGTH: 69
<212> TYPE: DNA
<213> ORGANISM: Methanobrevibacter ruminantium

<400> SEQUENCE: 253
atggataaaa agattttat agttagcttt attctgctag ctattttcac aatagggct     60 gttggcgct                                                           69

<210> SEQ ID NO 254
<211> LENGTH: 81
<212> TYPE: DNA
<213> ORGANISM: Methanobrevibacter ruminantium

<400> SEQUENCE: 254
atgatgaaaa tgactaaaaa gaatcttttt ttaattagtt taatactact aattattctt   60
acaattggtg ctgtcagcgc a                                             81

<210> SEQ ID NO 255
<211> LENGTH: 81
<212> TYPE: DNA
<213> ORGANISM: Methanobrevibacter ruminantium

<400> SEQUENCE: 255
atggtgatta tgaataataa aaagcttttt attgttagtt tgattatact aactatttg    60 acaataggcg ctgtcagtgc a                                             81

<210> SEQ ID NO 256
<211> LENGTH: 81
<212> TYPE: DNA
<213> ORGANISM: Methanobrevibacter ruminantium
```

```
<400> SEQUENCE: 256
atgaagttta taaaaatag gggcatatct gccatatcaa taattttaat tctatttta      60 agtatttcta tggcatctgc t                                              81

<210> SEQ ID NO 257
<211> LENGTH: 90
<212> TYPE: DNA
<213> ORGANISM: Methanobrevibacter ruminantium

<400> SEQUENCE: 257
gtgtttattt tgaaatttga aattaaaaga agtttaatat tcatttcaat attagcaata    60
ttgatcttat ctattggaat ggcatctgaa                                     90

<210> SEQ ID NO 258
<211> LENGTH: 126
<212> TYPE: DNA
<213> ORGANISM: Methanobrevibacter ruminantium

<400> SEQUENCE: 258
atgcaagcaa ttattccagt taaagacaat tttctaattt tagtgacaaa tatgaagaaa    60
agtgatttta aacgtatatt catatgttta gttcttctta cttgcttgat tggtgcagta   120
agtgct                                                              126

<210> SEQ ID NO 259
<211> LENGTH: 78
<212> TYPE: DNA
<213> ORGANISM: Methanobrevibacter ruminantium

<400> SEQUENCE: 259
atgaacttta aaaactttt aatgatttca ttaatcttat tatttgtctt atcagtagga     60
tttagcacag caagcgct                                                  78

<210> SEQ ID NO 260
<211> LENGTH: 72
<212> TYPE: DNA
<213> ORGANISM: Methanobrevibacter ruminantium

<400> SEQUENCE: 260
atgaaaatta aaagagttt tgtcattta tgcttaatta tctgtttatt tactattgca      60
agtgttgcag ct                                                        72

<210> SEQ ID NO 261
<211> LENGTH: 69
<212> TYPE: DNA
<213> ORGANISM: Methanobrevibacter ruminantium

<400> SEQUENCE: 261
gtgactgttt cagttttat aagtgcttca tttgcttttg gcaatgttct aagcaatgca     60
gataacgga                                                            69

<210> SEQ ID NO 262
<211> LENGTH: 66
<212> TYPE: DNA
<213> ORGANISM: Methanobrevibacter ruminantium

<400> SEQUENCE: 262
atgaaggtct taaagatagc aattatcatg cttattttaa tcatatctct gggagcggtt    60
tcagca                                                               66
```

-continued

```
<210> SEQ ID NO 263
<211> LENGTH: 81
<212> TYPE: DNA
<213> ORGANISM: Methanobrevibacter ruminantium

<400> SEQUENCE: 263
atgaatttta aaacaaaagg aagcttgatt cttatttcat tacttttcat tttaataata    60
ggtattggaa tggcatcagc a                                              81

<210> SEQ ID NO 264
<211> LENGTH: 63
<212> TYPE: DNA
<213> ORGANISM: Methanobrevibacter ruminantium

<400> SEQUENCE: 264
atgggaaaat ttaaatttat atttattcta gttttagctc tattttaat atgtggaatt     60 gct                                                                  63

<210> SEQ ID NO 265
<211> LENGTH: 75
<212> TYPE: DNA
<213> ORGANISM: Methanobrevibacter ruminantium

<400> SEQUENCE: 265
atggattcta agaaaatatt aatgattgct gtagttgctt taatagcaat tgttgctgta    60
agttcatgct ctgca                                                     75

<210> SEQ ID NO 266
<211> LENGTH: 75
<212> TYPE: DNA
<213> ORGANISM: Methanobrevibacter ruminantium

<400> SEQUENCE: 266
atgaagttaa aatcaaagta ttttgtattt ttactcataa tatgtatcct attcagtatt    60
tcaacagttt cagcg                                                     75

<210> SEQ ID NO 267
<211> LENGTH: 81
<212> TYPE: DNA
<213> ORGANISM: Methanobrevibacter ruminantium

<400> SEQUENCE: 267
atgaattatt ccattattat cttcattatc tttcttatgg atgcattggt gttaatggct    60
agcatacaag tctgtggagc t                                              81

<210> SEQ ID NO 268
<211> LENGTH: 78
<212> TYPE: DNA
<213> ORGANISM: Methanobrevibacter ruminantium

<400> SEQUENCE: 268
atgaagttta attcaagagt tttagggatt ttatctctat tatttgttct tacaattctt    60
gtttcaagtg tggggggca                                                 78

<210> SEQ ID NO 269
<211> LENGTH: 54
<212> TYPE: DNA
<213> ORGANISM: Methanobrevibacter ruminantium

<400> SEQUENCE: 269
```

-continued

```
atggaaaaga aaactacaat tatattggtt attttaattg ctcttattgc atgc          54

<210> SEQ ID NO 270
<211> LENGTH: 75
<212> TYPE: DNA
<213> ORGANISM: Methanobrevibacter ruminantium

<400> SEQUENCE: 270
atgaagaata agagtttaat attaatttct ttattattac tgattacaat aataagcata   60
ggatctgttg ttgca                                                    75

<210> SEQ ID NO 271
<211> LENGTH: 69
<212> TYPE: DNA
<213> ORGANISM: Methanobrevibacter ruminantium

<400> SEQUENCE: 271
atgagaagca ctatcctgtt aagtgcaagt actgcggaaa gccgttcacc aagtctcaca   60
acaggcaga                                                           69

<210> SEQ ID NO 272
<211> LENGTH: 93
<212> TYPE: DNA
<213> ORGANISM: Methanobrevibacter ruminantium

<400> SEQUENCE: 272
gtgcttctca tttgctttat aggattggtt gaggcgatac tgatggcatt ggttgattgg   60
gaggacttgg caatatccgt tcgcaagtct cct                                93

<210> SEQ ID NO 273
<211> LENGTH: 72
<212> TYPE: DNA
<213> ORGANISM: Methanobrevibacter ruminantium

<400> SEQUENCE: 273
atgaataaaa aaattatctt atccctcctt ttagtattat tagtagctat ttctgtctct   60
gcagttgcag ca                                                       72

<210> SEQ ID NO 274
<211> LENGTH: 110
<212> TYPE: DNA
<213> ORGANISM: Methanobrevibacter ruminantium

<400> SEQUENCE: 274
atgtcgttat ccatatttgt tctggttata ggaggtggat ttattaataa aagaatatta   60
ttaatattcg tatttctaat attcttcata agtattggat ctgtagttgc              110

<210> SEQ ID NO 275
<211> LENGTH: 75
<212> TYPE: DNA
<213> ORGANISM: Methanobrevibacter ruminantium

<400> SEQUENCE: 275
atgaacaata aaagattat aatgtctttt ctattggtcc tattgattgc aatatctgtc    60
tctgcagttt cagca                                                    75

<210> SEQ ID NO 276
<211> LENGTH: 75
<212> TYPE: DNA
<213> ORGANISM: Methanobrevibacter ruminantium
```

```
<400> SEQUENCE: 276
atgaaaatcc aaagaggtat atatataata ttaactttac ttgttctctt tagcctttct    60
gctgcaagcg cagca                                                     75

<210> SEQ ID NO 277
<211> LENGTH: 90
<212> TYPE: DNA
<213> ORGANISM: Methanobrevibacter ruminantium

<400> SEQUENCE: 277
atggaactta agtagatca agataaatgt ttaggttgtg gagtatgtgt tatcgcatgt    60
cctgtaaacg cttccatcag tccggaaaac                                    90

<210> SEQ ID NO 278
<211> LENGTH: 51
<212> TYPE: DNA
<213> ORGANISM: Methanobrevibacter ruminantium

<400> SEQUENCE: 278
atgaatcgaa gatcaaagtt aataattgcg attttaatag ttatcataat a             51

<210> SEQ ID NO 279
<211> LENGTH: 60
<212> TYPE: DNA
<213> ORGANISM: Methanobrevibacter ruminantium

<400> SEQUENCE: 279
atgaaaagat caaaaaaatt aattatagca attcttgttg taatccttt gggattacta    60

<210> SEQ ID NO 280
<211> LENGTH: 105
<212> TYPE: DNA
<213> ORGANISM: Methanobrevibacter ruminantium

<400> SEQUENCE: 280
atgaaagaat acaagatagc aattataggagggcag caggaatgat agctgcaata    60
agagccgcag aaatattagg cccaaatgca gtatgcattc tagag                  105

<210> SEQ ID NO 281
<211> LENGTH: 75
<212> TYPE: DNA
<213> ORGANISM: Methanobrevibacter ruminantium

<400> SEQUENCE: 281
atggcaaatg aaggtggagg acatttaaag actattttga tgattataat cttaatagct    60
tttatttgtg gtctt                                                    75

<210> SEQ ID NO 282
<211> LENGTH: 87
<212> TYPE: DNA
<213> ORGANISM: Methanobrevibacter ruminantium

<400> SEQUENCE: 282
atggataata aaatcaaagc aggcattgca cttgcaataa tcgttttagt ggctgtcatt    60
ggcttttcat tcattaatga aagcaat                                       87

<210> SEQ ID NO 283
<211> LENGTH: 75
<212> TYPE: DNA
<213> ORGANISM: Methanobrevibacter ruminantium
```

```
<400> SEQUENCE: 283
atgtttaaag taagcaaaag catattaatc gtttgtttag tatcccttt cctattagtt    60 tcacaagcta gcgct                                                    75

<210> SEQ ID NO 284
<211> LENGTH: 75
<212> TYPE: DNA
<213> ORGANISM: Methanobrevibacter ruminantium

<400> SEQUENCE: 284
atgtggtatg atatgaaaag aagaaggttt tatttaatat tatttataat tctattgatt    60
ttagcagcta tagca                                                    75

<210> SEQ ID NO 285
<211> LENGTH: 81
<212> TYPE: DNA
<213> ORGANISM: Methanobrevibacter ruminantium

<400> SEQUENCE: 285
atgaaaatta cagttgcggg tgtaggatat gtagggcttt cacttgctgt tctgctcgct    60
caaaaacatg atgttacagc t                                             81

<210> SEQ ID NO 286
<211> LENGTH: 90
<212> TYPE: DNA
<213> ORGANISM: Methanobrevibacter ruminantium

<400> SEQUENCE: 286
atgaatttga tgaaaattac agttgcggga gtgggatatg tagggctttc tattgctatt    60
ctgcttgccc agaaacatga tgtaaccgca                                    90

<210> SEQ ID NO 287
<211> LENGTH: 81
<212> TYPE: DNA
<213> ORGANISM: Methanobrevibacter ruminantium

<400> SEQUENCE: 287
atggagataa gatataaaaa tttattaaaa gttttactat ttttcttgt tttactcatc    60 agttgcggat ttgcctcagc a                                             81

<210> SEQ ID NO 288
<211> LENGTH: 81
<212> TYPE: DNA
<213> ORGANISM: Methanobrevibacter ruminantium

<400> SEQUENCE: 288
atgaagataa gatataaaaa tttattaaaa gttttactat ttttcttgt tttactcatc    60 agttgcggat ttgcctcagc a                                             81

<210> SEQ ID NO 289
<211> LENGTH: 69
<212> TYPE: DNA
<213> ORGANISM: Methanobrevibacter ruminantium

<400> SEQUENCE: 289
atgcaacgtt cattatttga taaagttaaa acatccttat ggatgcttcc atccttttt    60 ggattggta                                                           69
```

```
<210> SEQ ID NO 290
<211> LENGTH: 81
<212> TYPE: DNA
<213> ORGANISM: Methanobrevibacter ruminantium

<400> SEQUENCE: 290
atgaaattta agaattcaca tatcttactc gtttcattaa tatccatttt cctattgttg      60
agcataagcg cagcttctgc a                                                81

<210> SEQ ID NO 291
<211> LENGTH: 75
<212> TYPE: DNA
<213> ORGANISM: Methanobrevibacter ruminantium

<400> SEQUENCE: 291
atgaattcta aaagatagc aattgttctt ggaataatat tgctttcatt tgcaattgta       60
ggctctgcat cagct                                                       75

<210> SEQ ID NO 292
<211> LENGTH: 117
<212> TYPE: DNA
<213> ORGANISM: Methanobrevibacter ruminantium

<400> SEQUENCE: 292
atggatgaat gtaaacttgt attaatcggt tttggcgctg taggccaagg tgttgcacgt      60
gcaatatcca tgaaaaagga atgatcaat gagaagtttg gcataagcct aaaagta         117

<210> SEQ ID NO 293
<211> LENGTH: 72
<212> TYPE: DNA
<213> ORGANISM: Methanobrevibacter ruminantium

<400> SEQUENCE: 293
atgatgagga aacaatatt tggagttata tttatcgttt ttatttatt cagcatttca        60 acggtttcag ca                                                          72

<210> SEQ ID NO 294
<211> LENGTH: 69
<212> TYPE: DNA
<213> ORGANISM: Methanobrevibacter ruminantium

<400> SEQUENCE: 294
atgaataaac aaaacgtatt tgctttgata ttattaacaa tcattctttt atctgtagtt      60
gctgtcagc                                                              69

<210> SEQ ID NO 295
<211> LENGTH: 75
<212> TYPE: DNA
<213> ORGANISM: Methanobrevibacter ruminantium

<400> SEQUENCE: 295
atgttgaata aaaaaataat aataatttta acatttattt taatattgtc tatttcttca     60
gcaagtgcat ctgca                                                       75

<210> SEQ ID NO 296
<211> LENGTH: 66
<212> TYPE: DNA
<213> ORGANISM: Methanobrevibacter ruminantium

<400> SEQUENCE: 296
atgggagtat tagctagtgt tgctggaggc atattttttg aagcaggcat gattgctact     60
``` tgtaca                                                            66

<210> SEQ ID NO 297
<211> LENGTH: 99
<212> TYPE: DNA
<213> ORGANISM: Methanobrevibacter ruminantium

<400> SEQUENCE: 297
gtgttttcag tgagtttaaa taaacttaag attggtagag ttttatttg tcttttatt   60 ttagttttta tttcttgttc aattaattgt gtttttgca                        99

<210> SEQ ID NO 298
<211> LENGTH: 54
<212> TYPE: DNA
<213> ORGANISM: Methanobrevibacter ruminantium

<400> SEQUENCE: 298
atgggaggtg aataataaa taatgaaaaa ttaaagttaa ttttaatttt aacc         54

<210> SEQ ID NO 299
<211> LENGTH: 87
<212> TYPE: DNA
<213> ORGANISM: Methanobrevibacter ruminantium

<400> SEQUENCE: 299
atggataaga aaatgattgt ttcagtggct tttcttttat tgattttggc agtggcttta  60
gtctctgtat ttgatgaaag caatagc                                     87

<210> SEQ ID NO 300
<211> LENGTH: 66
<212> TYPE: DNA
<213> ORGANISM: Methanobrevibacter ruminantium

<400> SEQUENCE: 300
atgaaaatct caagaataat tgtattatta atgattctaa tcttcactgc aggaatggtt  60
tatgca                                                            66

<210> SEQ ID NO 301
<211> LENGTH: 75
<212> TYPE: DNA
<213> ORGANISM: Methanobrevibacter ruminantium

<400> SEQUENCE: 301
atggattcta aaaaaatatt agttatttta ggtttaactg ttttagctat ttttttagct  60
agttcagtta gtgct                                                  75

<210> SEQ ID NO 302
<211> LENGTH: 99
<212> TYPE: DNA
<213> ORGANISM: Methanobrevibacter ruminantium

<400> SEQUENCE: 302
atgaaaccat atgtaattct cataggaagc gcttcaggga taggaaaatc cacagttgca  60
gctgaacttg caaaaacatt aaacattaag cacttggtg                        99

<210> SEQ ID NO 303
<211> LENGTH: 54
<212> TYPE: DNA
<213> ORGANISM: Methanobrevibacter ruminantium

<400> SEQUENCE: 303

```
atgttaatat cagtcttggg agtgattgta attatcatta tggtagttgc agct           54
```

<210> SEQ ID NO 304
<211> LENGTH: 63
<212> TYPE: DNA
<213> ORGANISM: Methanobrevibacter ruminantium

<400> SEQUENCE: 304

```
atggcaacca gaacaaaaca aactatatgc aggttgtatt ccttccatgg gggtcgtttc     60
tta                                                                   63
```

<210> SEQ ID NO 305
<211> LENGTH: 63
<212> TYPE: DNA
<213> ORGANISM: Methanobrevibacter ruminantium

<400> SEQUENCE: 305

```
atggaattaa gtaaaagtga caaatattta atcgtagtag ggattatatt ctgtcttgca     60
tta                                                                   63
```

<210> SEQ ID NO 306
<211> LENGTH: 66
<212> TYPE: DNA
<213> ORGANISM: Methanobrevibacter ruminantium

<400> SEQUENCE: 306

```
atgaaagtag caattttagg tgctggctgt tacagaactc acgcagctag tggaattaca     60
aatttt                                                                66
```

<210> SEQ ID NO 307
<211> LENGTH: 48
<212> TYPE: DNA
<213> ORGANISM: Methanobrevibacter ruminantium

<400> SEQUENCE: 307

```
ttgtcagtta ttctgattct gttttagca gtttcaacgg tagctgca                   48
```

<210> SEQ ID NO 308
<211> LENGTH: 48
<212> TYPE: DNA
<213> ORGANISM: Methanobrevibacter ruminantium

<400> SEQUENCE: 308

```
atgaataaga aacttaaaat aatcctttat attttattgg ctttaata                  48
```

<210> SEQ ID NO 309
<211> LENGTH: 93
<212> TYPE: DNA
<213> ORGANISM: Methanobrevibacter ruminantium

<400> SEQUENCE: 309

```
atggaaacta aaaatcttat aatcatttgt gcaactgtaa tattggctgt tgtaatagtt     60
ttatctgctt ttatttatgt caacatgggc aat                                  93
```

<210> SEQ ID NO 310
<211> LENGTH: 63
<212> TYPE: DNA
<213> ORGANISM: Methanobrevibacter ruminantium

<400> SEQUENCE: 310

```
gtgcttgttt tagcttttgc aataatattt ctaggatatt ccatctcctt aggaaacaat     60
```

-continued

```
caa                                                                 63

<210> SEQ ID NO 311
<211> LENGTH: 66
<212> TYPE: DNA
<213> ORGANISM: Methanobrevibacter ruminantium

<400> SEQUENCE: 311
atggaattga atgatgaaat aatatttaaa gttgcactga ttactgcatt ggtcggaatg    60
attggg                                                              66

<210> SEQ ID NO 312
<211> LENGTH: 75
<212> TYPE: DNA
<213> ORGANISM: Methanobrevibacter ruminantium

<400> SEQUENCE: 312
atgaaaaatt atttcgacat aaaagacaaa gtagcagttg taaccggtgc ttcttccgga    60
ttaggttggc aaatt                                                    75

<210> SEQ ID NO 313
<211> LENGTH: 95
<212> TYPE: DNA
<213> ORGANISM: Methanobrevibacter ruminantium

<400> SEQUENCE: 313
ttgactttca acaaccttag aataaacatt aaagattgca tggtaatatt tgtagtgttt    60
acagtattgc ttttatctat tttagctgta agtgc                              95

<210> SEQ ID NO 314
<211> LENGTH: 73
<212> TYPE: DNA
<213> ORGANISM: Methanobrevibacter ruminantium

<400> SEQUENCE: 314
atgaaattca aaaatatttt atttattctg ctaatagctc ttatttgcat aatcagtgtc    60
tctgcagttg ctg                                                      73

<210> SEQ ID NO 315
<211> LENGTH: 60
<212> TYPE: DNA
<213> ORGANISM: Methanobrevibacter ruminantium

<400> SEQUENCE: 315
atggataaaa aaatgacagt tttattggtt gccctatttt gccttctctg tgtaggctca    60

<210> SEQ ID NO 316
<211> LENGTH: 83
<212> TYPE: DNA
<213> ORGANISM: Methanobrevibacter ruminantium

<400> SEQUENCE: 316
atggatagaa aggacatcat aatcataata ctcgttctca taatcatatc actattggca    60
ttgggccttc ataatcatca agt                                           83

<210> SEQ ID NO 317
<211> LENGTH: 81
<212> TYPE: DNA
<213> ORGANISM: Methanobrevibacter ruminantium

<400> SEQUENCE: 317
```

```
atgacatctg agattatgat tttaacacca actgcagtgg ttttagcggc ggacagtgca    60
gttacaataa gcgatataaa a                                              81

<210> SEQ ID NO 318
<211> LENGTH: 69
<212> TYPE: DNA
<213> ORGANISM: Methanobrevibacter ruminantium

<400> SEQUENCE: 318
atgaggaaaa agatcctttt cctaactttg atgatactaa tctgttttac tttaaacagc    60
gtttgtgct                                                            69

<210> SEQ ID NO 319
<211> LENGTH: 69
<212> TYPE: DNA
<213> ORGANISM: Methanobrevibacter ruminantium

<400> SEQUENCE: 319
atgagattaa gatattttgc aataattagt ttaattcttt taatattttt agttccagtt    60
agttttgca                                                            69

<210> SEQ ID NO 320
<211> LENGTH: 54
<212> TYPE: DNA
<213> ORGANISM: Methanobrevibacter ruminantium

<400> SEQUENCE: 320
atgtttattg gcttattatt aataggtcta ttaatcatcc ctataagttt tgct           54

<210> SEQ ID NO 321
<211> LENGTH: 71
<212> TYPE: DNA
<213> ORGANISM: Methanobrevibacter ruminantium

<400> SEQUENCE: 321
ttgctaattg gacttgtcat ctgtgcaggt gtcttttatt tccaatttaa ctatgcaact    60
cccacatatc t                                                         71

<210> SEQ ID NO 322
<211> LENGTH: 75
<212> TYPE: DNA
<213> ORGANISM: Methanobrevibacter ruminantium

<400> SEQUENCE: 322
gtggttttag ttgctgttgt agtgattggc tctactgcat tcctattaaa ttatgatgaa    60
actgtaaaat acact                                                     75

<210> SEQ ID NO 323
<211> LENGTH: 60
<212> TYPE: DNA
<213> ORGANISM: Methanobrevibacter ruminantium

<400> SEQUENCE: 323
atggataaaa aaactctagc aattattgct attatcgtta tagctcttgt agctgttggt    60

<210> SEQ ID NO 324
<211> LENGTH: 72
<212> TYPE: DNA
<213> ORGANISM: Methanobrevibacter ruminantium

<400> SEQUENCE: 324
```

```
atgaataata agacattatt tatcattggt ttattcatat gtcttttatt taccatacct    60
atggtatcag ct                                                        72

<210> SEQ ID NO 325
<211> LENGTH: 60
<212> TYPE: DNA
<213> ORGANISM: Methanobrevibacter ruminantium

<400> SEQUENCE: 325
atgataaaaa cagacaataa aggacagata acagtcgaac tgctccttct tttaagcttt    60

<210> SEQ ID NO 326
<211> LENGTH: 72
<212> TYPE: DNA
<213> ORGANISM: Methanobrevibacter ruminantium

<400> SEQUENCE: 326
atgttaaata gaaaggcttt gattttttca ttgattgttt tatttatgct atccatttct    60
gctgtttcag ct                                                        72

<210> SEQ ID NO 327
<211> LENGTH: 69
<212> TYPE: DNA
<213> ORGANISM: Methanobrevibacter ruminantium

<400> SEQUENCE: 327
atggataata aagcgataat tggaattgta attgcattga ttgtaattgt ccttgcatgc    60
tttgcttat                                                            69

<210> SEQ ID NO 328
<211> LENGTH: 90
<212> TYPE: DNA
<213> ORGANISM: Methanobrevibacter ruminantium

<400> SEQUENCE: 328
atgagttatt ttaataaagg acatatatgg aatattttat taatttgtct tctcatcgga    60
actttggcta tgatgggttc agcaagtgcc                                     90

<210> SEQ ID NO 329
<211> LENGTH: 93
<212> TYPE: DNA
<213> ORGANISM: Methanobrevibacter ruminantium

<400> SEQUENCE: 329
atgaaaaaca aggcaatgtt tttaatatct gcattattga tagcagttat tctatctctc    60
agtgctgtaa gtgctgcaga tgatgctatt gct                                 93

<210> SEQ ID NO 330
<211> LENGTH: 75
<212> TYPE: DNA
<213> ORGANISM: Methanobrevibacter ruminantium

<400> SEQUENCE: 330
atgaaattta acaagagttt aattgcaatt tttgtaattt tgattgttgc tttcagttcc    60
atatctgtca ttgca                                                     75

<210> SEQ ID NO 331
<211> LENGTH: 60
<212> TYPE: DNA
<213> ORGANISM: Methanobrevibacter ruminantium
```

```
<400> SEQUENCE: 331
atggataaaa aaattattat cggtgcagtt gttgcacttc ttgttataat tgttggtgct      60

<210> SEQ ID NO 332
<211> LENGTH: 48
<212> TYPE: DNA
<213> ORGANISM: Methanobrevibacter ruminantium

<400> SEQUENCE: 332
gtggaaggtg ataatatggt aaatataaaa actgttgcat tagctgtt                  48

<210> SEQ ID NO 333
<211> LENGTH: 78
<212> TYPE: DNA
<213> ORGANISM: Methanobrevibacter ruminantium

<400> SEQUENCE: 333
atgctgatta tggcaattct tgttttattg accatggcca gcgtaagtgc cagcgaactt      60
gaagacattc aagtcaca                                                   78

<210> SEQ ID NO 334
<211> LENGTH: 48
<212> TYPE: DNA
<213> ORGANISM: Methanobrevibacter ruminantium

<400> SEQUENCE: 334
atgaataaca ctactaaaat attaattgga gttcttatgg gactgctt                  48

<210> SEQ ID NO 335
<211> LENGTH: 63
<212> TYPE: DNA
<213> ORGANISM: Methanobrevibacter ruminantium

<400> SEQUENCE: 335
atggaaacag aaaatttaat tattgtaatt cttttagttt taatagctat ggccggaatt      60
ttc                                                                   63

<210> SEQ ID NO 336
<211> LENGTH: 63
<212> TYPE: DNA
<213> ORGANISM: Methanobrevibacter ruminantium

<400> SEQUENCE: 336 atgttttgg ttatattatt atttgcattt attgttatag gaggatctta ttcggtattt      60
gct                                                                   63

<210> SEQ ID NO 337
<211> LENGTH: 114
<212> TYPE: DNA
<213> ORGANISM: Methanobrevibacter ruminantium

<400> SEQUENCE: 337
atggctttgc ttattcttgc aatgtcatgt gtgtctgcaa gcaatgcaag tgataatttg      60
gatgatttaa ccatttcaga cagtaattca ctagatcttg tatctacatc aaat          114

<210> SEQ ID NO 338
<211> LENGTH: 48
<212> TYPE: DNA
<213> ORGANISM: Methanobrevibacter ruminantium

<400> SEQUENCE: 338
```

-continued

```
atgaacaata atactttttt aggaataatt ataataataa ttgcagtt          48
```

<210> SEQ ID NO 339
<211> LENGTH: 93
<212> TYPE: DNA
<213> ORGANISM: Methanobrevibacter ruminantium

<400> SEQUENCE: 339

```
atgctttttaa atgataaatc tgaactatta aaatcattat ctattttatt tttgctaata   60
gttctaatta caagttttaa ttcagtttat gca                                 93
```

<210> SEQ ID NO 340
<211> LENGTH: 60
<212> TYPE: DNA
<213> ORGANISM: Methanobrevibacter ruminantium

<400> SEQUENCE: 340

```
atgaaaaaaa taattcttgg aacatgtatc ttattcttgt tgattagtgt cgcatatgca   60
```

<210> SEQ ID NO 341
<211> LENGTH: 81
<212> TYPE: DNA
<213> ORGANISM: Methanobrevibacter ruminantium

<400> SEQUENCE: 341

```
atgaaaatta atttaaaaag agttatttg ggaattattt tgattttgat ttgcatttcc    60
tcagcaagta tcatttcagc a                                              81
```

<210> SEQ ID NO 342
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342

```
atggtgctgg cgctgagcat tattctgctg agcagcattg cggcggcgag cgcg          54
```

<210> SEQ ID NO 343
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343

```
atgagcacct ttattctggt gattattatt ctgggcatta ttctgattat tgcg           54
```

<210> SEQ ID NO 344
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344

```
atggataaca aaaaaatttt tgtgattgtg gcgctggcgc tgctggcgat tgtggcggtg   60
ggcagcgtga gcgcg                                                     75
```

<210> SEQ ID NO 345

```
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
atgaacaaca aaaaattttt tgcgattgcg gcgctggcga ttattgcgat tgtggcggtg      60
ggcagcgtga gcgcg                                                      75

<210> SEQ ID NO 346
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
atgaacgcga aaaactgac cattctggcg gcgctggcga ttctggcgat tgtggcggtg       60
ggcagcgtga gcgcg                                                      75

<210> SEQ ID NO 347
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
atgatttgct gcgtgctgct gacctttagc accgtgagcg cgattgatat ggatggcaac      60
ctgacc                                                                66

<210> SEQ ID NO 348
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
atgattattg cgattatttt tatgtataac cgcgtgcgca acaaacgc                  48

<210> SEQ ID NO 349
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
atgaacaaag tgcagctgag cagcattctg gcgctggtgc tgattctgtt tctgagcctg      60
gcggtggtga gcgcg                                                      75

<210> SEQ ID NO 350
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 350
atgcgcaaag aaattattag cattctggtg attgcgatta ttgcgattag cgtgattccg      60
accgcgttta gc                                                          72

<210> SEQ ID NO 351
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
atgaacaaaa aacgctttaa actgctgctg accattttta ttgcgtttgc gctgattaac      60 acctgctttta ttctgaacga taacctgagc                                     90

<210> SEQ ID NO 352
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
atgatggtga ttctgctgat taccctgctg agcgtgccga ttctgagcct gaccattgat      60
tatagc                                                                 66

<210> SEQ ID NO 353
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
atgaacatta acctgaaaaa aattacccttt ctgtgcctgg tgctggtgct gattggcctg     60
attagcttta acagcattag cgcg                                             84

<210> SEQ ID NO 354
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
atgaacaacc agaacaaata tagctgcatt gtgctggcgg gcggcatgag ccgccgcatg      60
ggccag                                                                 66

<210> SEQ ID NO 355
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
atggaagatc gcaaagcgaa atttattgtg tatgtggtgg tgtgcctgct ggcgtttatt      60
tgcagcagca ccgtgtttag catgaccggc ggcctgagc                             99
```

<210> SEQ ID NO 356
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
atgaacattc tgattaacgg caccggcgcg attggcattg gcctgggcgc gagcatgatt      60
agccagggc                                                             69

<210> SEQ ID NO 357
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
atgattattg tgaccaccat ttgcgtgatt ctgattctga ttgtgctgtt ttatggcctg      60
tttccgggcc tgaccaacag c                                               81

<210> SEQ ID NO 358
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
atgagcgatg tgggcaaaac cgtgattacc accattatta ccctggtgac caccgcgttt      60
ggc                                                                   63

<210> SEQ ID NO 359
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
atgaaaagcg ataaacgcgc gaaatttgcg attttttta gcattgcgat tctggcgctg      60
ggcctgagca acattgcggc g                                               81

<210> SEQ ID NO 360
<211> LENGTH: 108
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
atgattaacg gcattatgga taaacagaaa gtgattaccg cgtttggcat tattctgttt      60
ctggcggcgg cgtttagccc gtttgtggtg ctgccgattc tgggcgtg                 108

<210> SEQ ID NO 361
<211> LENGTH: 75
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 361
atgtttaaca aaaaaatggt gctggcgatt agcctgctgg cggtgatttt tgcgagcatg    60
tgcattgtga gcgcg                                                     75

<210> SEQ ID NO 362
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
atgaaaacca acctgaaaaa aaccaccatt attctggcgc tgctgatggc gattctgatt    60
ctgagcattg gcgcgattag cgcg                                           84

<210> SEQ ID NO 363
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
atgaacagca aaggcaaata tctggtgctg tttctgattc tgattctgag ctttagcatt    60
attagcgcga gctttgcg                                                  78

<210> SEQ ID NO 364
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
atgaaaaaaa acctgagcct gaaaaacatt ctgattctga gcctgatttt tctgtttgtg    60
ctgagcattg gcagcagctt tgcg                                           84

<210> SEQ ID NO 365
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
atgaaacgca acatttattt tattattctg ctggtgaccc tgtttctgat tagcatgagc    60
gtggtgagcg cg                                                        72

<210> SEQ ID NO 366
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 366
atgaaaaaaa tggaaatggc gagctatatt attctgattg cgagcgtgct ggcgattctg      60
tatgcg                                                                 66

<210> SEQ ID NO 367
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
atgccgaaaa ttgcgaaact gtggaacaaa ctggcggatc cgaaaaacat tccgcgcctg      60
tttgcggtga tt                                                          72

<210> SEQ ID NO 368
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
atgtttaacc tggcgatttg ggtgtatctg ggcctggcgc tggcgatttt tggcagcctg      60
gcgaccgtgt ggggcccggg cgtgaaagat ccg                                   93

<210> SEQ ID NO 369
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
atgtttgcga ttgtgagcct gagcgcggtg agcgcgagcg atgattttag cagcagcctg      60
gcggatgata gcgatagcga t                                                81

<210> SEQ ID NO 370
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
atgaaacgcc gctataaagt gctgtttctg ctggcgattc tgaccattat tagcattaac      60
gcgattagcg cg                                                          72

<210> SEQ ID NO 371
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
atgctgttta gcgtgattgc gaccgtgagc gcgacctgc                             39
```

```
<210> SEQ ID NO 372
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
atgtttatta aaattcgccg cgataccctg attattctgc tg                          42

<210> SEQ ID NO 373
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
atgaaagcgg tgattccggc ggcgggcctg ggcacccgct ttctgccggc gaccaaagcg       60
cagccgaaag aaatgctgcc ggtgtatgat aaaccgacca ttcag                      105

<210> SEQ ID NO 374
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
atgattaaaa ccgatgtgct ggtgattggc gcgggcccgg cgggcagcag cgcggcgcgc       60
tttgcggcga aaggcggc                                                    78

<210> SEQ ID NO 375
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
atggaagata acctgctgaa aaccgcaaa ctgattctga ttagcatttt tctggtgagc        60
ctgctggcga ttagcgcggt gagcgcg                                          87

<210> SEQ ID NO 376
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
atgaaccgca acaaaattat tgtgctgctg gtgctgctga ttgcggtggt gggctttacc       60
atgggcccgg cgtgcgcg                                                    78

<210> SEQ ID NO 377
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 377
atgaaaaaaa gcgtgtttaa aattctgatt gcgctggcgc tgattctgct ggcggtgagc    60
attgtgagca gc    72

<210> SEQ ID NO 378
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
atgaaaaaaa acatttttct gattgcgatt attctgattg cggtggtggc ggtgagcggc    60
tgc    63

<210> SEQ ID NO 379
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
atgctgattg cgctgctggg cctgagcgcg gtggcggcgg tggatgcgga tccgctgacc    60
gataac    66

<210> SEQ ID NO 380
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
atgagcgaaa acaaccgcac cctgattacc attggcattg gcgcgtttat tatt    54

<210> SEQ ID NO 381
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
atgggcaaaa tttttaaaat tgtgaccatt attctgattg tgattgcgct ggcgattctg    60
ggcgtgttta tttatagcga tggccatagc gaa    93

<210> SEQ ID NO 382
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
atggataaaa aaaccattat tattgcggcg gtggcgattc tggtgatt    48

<210> SEQ ID NO 383

-continued

```
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
atgaaactga acaaattttt tattattagc attattctga ttatttttct gagcattagc      60
gcgattagcg cg                                                          72

<210> SEQ ID NO 384
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
atgaaaaaaa aaattgcgat tattctgggc attgcgctgc tggcgtttct ggtgattggc      60
gcgagcagcg cg                                                          72

<210> SEQ ID NO 385
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 385
atgaacttta acaaaaaaat tctgctgatt attgcgctgg tgtttattgc gagcgtgggc      60
attgtggcgg cg                                                          72

<210> SEQ ID NO 386
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
atgaaacgca gcattatttt tctgaccatt attctgagcc tgtttctggt gattggctat      60
gcgagcgcg                                                              69

<210> SEQ ID NO 387
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
atgggcatta cctttaccgc gattattacc ggcgcgctgg cggcaccac ctttagcgaa       60 ccgctgggca actatctgag ccagtttatt ccgtat                                96

<210> SEQ ID NO 388
<211> LENGTH: 75
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 388
atggatagca aaaaactgat tctggtgacc gcgctggcgt ttctggcgat tgtgagcatt    60
gcgagcgtga gcgcg                                                    75

<210> SEQ ID NO 389
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
atgaacgtga acaaaaaaat ttttctgctg gtgattttta ttattagcat tagcattgcg    60
ggcgtgtatt gcgcggatat tcatcaggat agcgatctga ccgcg                  105

<210> SEQ ID NO 390
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
atgattctgg cgctgttttg ctttattgtg attggcagcg cgagcgcggc ggattttaaa    60

<210> SEQ ID NO 391
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 391
atgattagcc tgctgctgat tagcattctg gcgattagcg cggcgagcgc ggcg          54

<210> SEQ ID NO 392
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
atggaagaaa aaattgcgct ggcggcgtgc agcggcatga gcccgaacgg cctggtggcg    60
cgcgtggcgg tgcatgatct ggcgattgat                                    90

<210> SEQ ID NO 393
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
atgctgaaaa ccaaactgtg cggcattagc ctgaaaaacc cgctgatgct ggcggcgggc    60
gtgctgggca gccatgcg                                                 78

<210> SEQ ID NO 394
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
atggaaattg tgctgtgcgt gaccggcagc gtggcggcgg tggaaaccgt gaaactggcg    60
cgcgaattta aacgccaggg c                                              81

<210> SEQ ID NO 395
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
atggtggtgg cgaccattat ttttgcgagc agcctgtttg atgcgctgta tggctttaaa    60
aac                                                                  63

<210> SEQ ID NO 396
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
atgattctgg cgattctgct ggcggtgggc atgaccctga ccgcggtgag cgcg           54

<210> SEQ ID NO 397
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
atgaacaaac gcatttttct gtatattgcg ctgattttta ttattagcct gctgagcttt    60
agcgcggtga gcgcg                                                     75

<210> SEQ ID NO 398
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
atgaaatata acaaaaaaat ttttttttctg tttctgctgc tgtgcctgat tattccgcag   60
gcgatttat                                                            69

<210> SEQ ID NO 399
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
atgaacagca acaaaaccta tgcggtgctg ggcctgctgc tgctgctgat tctgagcatt    60
ggcgcgatta gcgcg                                                    75

<210> SEQ ID NO 400
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
atgattaaca aacgcattat tagcctgagc ctgctgatta ttctggtgtt tctgattatt    60
ggcctgagcg cggtgagcgc g                                             81

<210> SEQ ID NO 401
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
atggatttta aaaagcgat tccgctgttt gcgctgctgc tgctgattct gtttattatt    60
ggcagcagca gcgcg                                                    75

<210> SEQ ID NO 402
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
atgaaactga aaaatttag cgtgattctg gcggtgctgc tggtggcgat tctggcgatt    60
ggcgcggtga gcgcg                                                    75

<210> SEQ ID NO 403
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
atgattctga ttagcctgat tctggtgatt ctgagcatta gctgcgtgag cgcg          54

<210> SEQ ID NO 404
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
atggataaca gcaacattat tattagcgtg attattgtgc tgtgcattgc ggcgggcgtg    60
accgcg                                                              66

```
<210> SEQ ID NO 405
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
atggataaca gcagcattct gattagcgtg attattgtgc tgtgcattgc ggcgggcgtg      60
accgcg                                                                66

<210> SEQ ID NO 406
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
atgcgcaaag aaattctgat tgcggcgatt gcgattattc tgattctgtg cggcggcgtg      60
tttgcg                                                                66

<210> SEQ ID NO 407
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
atgctgatta gcattgtgct gattagcctg attgcgctgg gcgcggtgag cgcg            54

<210> SEQ ID NO 408
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
atgaaagaaa ttgcgattta tctgattctg attattattg tgctgattgc ggcgcagcat      60
ctg                                                                   63

<210> SEQ ID NO 409
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
atgtttgaag cgggcatgat tgcgctgccg accggcctgc cgggcctggc gctgctgggc      60
ctg                                                                   63

<210> SEQ ID NO 410
<211> LENGTH: 66
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 410
atgaaaaact ggaaaattat tggcctgatt ctgattattc tgctggcggt ggtgagcgtg    60
agcggc                                                              66

<210> SEQ ID NO 411
<211> LENGTH: 102
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
atgaaaccgc tgattattaa aattagcatt ttttgcaaca aaaaaatttt tatttttacc    60
ctgatgattg tgatgctgct gagcctggcg gcggtgagcg cg                     102

<210> SEQ ID NO 412
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
atgagcatta aacgcattct gctgaccagc ctgatgctgt ttattattat ttttagcatt    60
agctttgtga gcgcg                                                    75

<210> SEQ ID NO 413
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
atggataaag tgggcattat tggcgcgggc agcctgggca ccgcgctggc gcagaccgtg    60
gcgaacaacg tg                                                       72

<210> SEQ ID NO 414
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
atgatttgca gcattcaggc gtgcagcgcg agctgcaccg cggtgtatgt gggcccg       57

<210> SEQ ID NO 415
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
atgaaaatta gccgcattat tctgattctg ctgctgtttg tggtgttttt tgaaattggc    60
ctgtttagca gctataccat tgtgaacgcg                                    90

<210> SEQ ID NO 416
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 416
atgattctga ttattagcct gtttctgatt agcctgctgg cgattggcgc ggcgagcgcg        60

<210> SEQ ID NO 417
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 417
atgaaactgt ataaaaacag cattattatt ctgctgctga ttctgattct gagcattggc        60
gcggcggcgg cg                                                            72

<210> SEQ ID NO 418
<211> LENGTH: 66
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 418
atggcggtga ttctgattat tctgtttagc ctgggcaccg tggcggcgag cgaaaacatt        60
gtgatt                                                                   66

<210> SEQ ID NO 419
<211> LENGTH: 93
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 419
atgcgcaacc cgaaagatta tattatgaaa accgattatc tgattattct gatggcgctg        60
ctgctgatta gcattgtgag cccgattgcg gcg                                     93

<210> SEQ ID NO 420
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 420
atgaacaaca aaaaattttt tgtggcgggc ctggcgattc tggcgattgt gctgatgggc        60
agcgtggcg                                                                69

<210> SEQ ID NO 421
<211> LENGTH: 81
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 421
atggaaaaaa ccatgaaaag caaactgttt attctgctga ttattattag cattctgatt      60
agcattagca gcgtgagcgc g                                                81

<210> SEQ ID NO 422
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
atggataaaa aaatttttat tgtgagcttt attctgctgg cgattttac cattggcgcg       60 gtgggcgcg                                                              69

<210> SEQ ID NO 423
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
atgatgaaaa tgaccaaaaa aaacctgttt ctgattagcc tgattctgct gattattctg      60
accattggcg cggtgagcgc g                                                81

<210> SEQ ID NO 424
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
atggtgatta tgaacaacaa aaaactgttt attgtgagcc tgattattct gaccattctg      60
accattggcg cggtgagcgc g                                                81

<210> SEQ ID NO 425
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
atgaaattta acaaaaaccg cggcattagc gcgattagca ttattctgat tctgtttctg      60
agcattagca tggcgagcgc g                                                81

<210> SEQ ID NO 426
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426

```
atgtttattc tgaaatttga aattaaacgc agcctgattt ttattagcat tctggcgatt    60
ctgattctga gcattggcat ggcgagcgcg                                     90
```

<210> SEQ ID NO 427
<211> LENGTH: 126
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427

```
atgcaggcga ttattccggt gaaagataac tttctgattc tggtgaccaa catgaaaaaa    60
agcgatttta aacgcatttt tatttgcctg gtgctgctga cctgcctgat tggcgcggtg   120
agcgcg                                                              126
```

<210> SEQ ID NO 428
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428

```
atgaacttta aaaaactgct gatgattagc ctgattctgc tgtttgtgct gagcgtgggc    60
tttagcaccg cgagcgcg                                                  78
```

<210> SEQ ID NO 429
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429

```
atgaaaatta aaaaaagctt tgtgattctg tgcctgatta tttgcctgtt taccattgcg    60
agcgtggcgg cg                                                        72
```

<210> SEQ ID NO 430
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430

```
atgaccgtga gcgtgtttat tagcgcgagc tttgcgtttg caacgtgct gagcaacgcg     60 gataacggc                                                            69
```

<210> SEQ ID NO 431
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431

```
atgaaagtgc tgaaaattgc gattattatg ctgattctga ttattagcct gggcgcggtg    60
agcgcg                                                               66
```

<210> SEQ ID NO 432
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
atgaacttta aaaccaaagg cagcctgatt ctgattagcc tgctgtttat tctgattatt      60
ggcattggca tggcgagcgc g                                               81

<210> SEQ ID NO 433
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
atgggcaaat ttaaatttat ttttattctg gtgctggcgc tgtttctgat ttgcggcatt      60
gcg                                                                   63

<210> SEQ ID NO 434
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
atggatagca aaaaaattct gatgattgcg gtggtggcgc tgattgcgat tgtggcggtg      60
agcagctgca gcgcg                                                      75

<210> SEQ ID NO 435
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
atgaaactga aaagcaaata ttttgtgttt ctgctgatta tttgcattct gtttagcatt      60
agcaccgtga gcgcg                                                      75

<210> SEQ ID NO 436
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
atgaactata gcattattat ttttattatt tttctgatgg atgcgctggt gctgatggcg      60
agcattcagg tgtgcggcgc g                                               81

<210> SEQ ID NO 437
<211> LENGTH: 78
<212> TYPE: DNA

-continued

```
<213> ORGANISM: Artificial Sequence
<220> FEATURE:
<223> OTHER INFORMATION: Description of Artificial Sequence: Synthetic
      oligonucleotide

<400> SEQUENCE: 437
atgaaattta acagccgcgt gctgggcatt ctgagcctgc tgtttgtgct gaccattctg      60
gtgagcagcg tgggcgcg                                                   78

<210> SEQ ID NO 438
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
atggaaaaaa aaaccaccat tattctggtg attctgattg cgctgattgc gtgc           54

<210> SEQ ID NO 439
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
atgaaaaaca aaagcctgat tctgattagc ctgctgctgc tgattaccat tattagcatt     60
ggcagcgtgg tggcg                                                      75

<210> SEQ ID NO 440
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
atgcgcagca ccattctgct gagcgcgagc accgcggaaa gccgcagccc gagcctgacc     60
accggccgc                                                             69

<210> SEQ ID NO 441
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
atgctgctga tttgctttat tggcctggtg aagcgattc tgatggcgct ggtggattgg      60
gaagatctgg cgattagcgt gcgcaaaagc ccg                                  93

<210> SEQ ID NO 442
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
```

```
atgaacaaaa aaattattct gagcctgctg ctggtgctgc tggtggcgat tagcgtgagc      60
gcggtggcgg cg                                                         72

<210> SEQ ID NO 443
<211> LENGTH: 111
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
atgagcctga gcattttttgt gctggtgatt ggcggcggct ttattaacaa acgcattctg      60 ctgattttttg tgtttctgat ttttttttatt agcattggca gcgtggtggc g             111

<210> SEQ ID NO 444
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
atgaacaaca aaaaaattat tatgagcttt ctgctggtgc tgctgattgc gattagcgtg      60
agcgcggtga gcgcg                                                      75

<210> SEQ ID NO 445
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445 atgaaaaattc agcgcggcat ttatattatt ctgaccctgc tggtgctgtt tagcctgagc      60
gcggcgagcg cggcg                                                      75

<210> SEQ ID NO 446
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 446
atggaactga aagtggatca ggataaatgc ctgggctgcg gcgtgtgcgt gattgcgtgc      60
ccggtgaacg cgagcattag cccggaaaac                                      90

<210> SEQ ID NO 447
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
atgaaccgcc gcagcaaaact gattattgcg attctgattg tgattattat t              51

<210> SEQ ID NO 448
<211> LENGTH: 60
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
atgaaacgca gcaaaaaact gattattgcg attctggtgg tgattctgct gggcctgctg      60

<210> SEQ ID NO 449
<211> LENGTH: 105
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
atgaaagaat ataaaattgc gattattggc ggcggcccgg cgggcatgat tgcggcgatt      60
cgcgcggcgg aaattctggg cccgaacgcg gtgtgcattc tggaa                     105

<210> SEQ ID NO 450
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
atggcgaacg aaggcggcgg ccatctgaaa accattctga tgattattat tctgattgcg      60
tttatttgcg gcctg                                                       75

<210> SEQ ID NO 451
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
atggataaca aaattaaagc gggcattgcg ctggcgatta ttgtgctggt ggcggtgatt      60
ggctttagct ttattaacga aagcaac                                          87

<210> SEQ ID NO 452
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 452
atgtttaaag tgagcaaaag cattctgatt gtgtgcctgg tgagcctgtt tctgctggtg      60
agccaggcga gcgcg                                                       75

<210> SEQ ID NO 453
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
```

```
atgtggtatg atatgaaacg ccgccgcttt tatctgattc tgtttattat tctgctgatt    60
ctggcggcga ttgcg                                                     75

<210> SEQ ID NO 454
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
atgaaaatta ccgtggcggg cgtgggctat gtgggcctga gcctggcggt gctgctggcg    60
cagaaacatg atgtgaccgc g                                              81

<210> SEQ ID NO 455
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
atgaacctga tgaaaattac cgtggcgggc gtgggctatg tgggcctgag cattgcgatt    60
ctgctggcgc agaaacatga tgtgaccgcg                                     90

<210> SEQ ID NO 456
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
atggaaattc gctataaaaa cctgctgaaa gtgtttacca tttttctggt gctgctgatt    60
agctgcggct ttgcgagcgc g                                              81

<210> SEQ ID NO 457
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
atgaaaattc gctataaaaa cctgctgaaa gtgtttacca tttttctggt gctgctgatt    60
agctgcggct ttgcgagcgc g                                              81

<210> SEQ ID NO 458
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 458
atgcagcgca gcctgtttga taaagtgaaa accagcctgt ggatgctgcc gagctttttt    60
ggcctggtg                                                            69
```

<210> SEQ ID NO 459
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
atgaaattta aaaacagcca tattctgctg gtgagcctga ttagcatttt tctgctgctg    60
agcattagcg cggcgagcgc g                                              81

<210> SEQ ID NO 460
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
atgaacagca aaaaaattgc gattgtgctg ggcattattc tgctgagctt tgcgattgtg    60
ggcagcgcga gcgcg                                                     75

<210> SEQ ID NO 461
<211> LENGTH: 117
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
atggatgaat gcaaactggt gctgattggc tttggcgcgg tgggccaggg cgtggcgcgc    60
gcgattagca tgaaaaaaga atgattaac gaaaaatttg gcattagcct gaaagtg      117

<210> SEQ ID NO 462
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
atgatgcgca aaaccatttt tggcgtgatt tttattgtgt ttattctgtt tagcattagc    60
accgtgagcg cg                                                        72

<210> SEQ ID NO 463
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
atgaacaaac agaacgtgtt tgcgctgatt ctgctgacca ttattctgct gagcgtggtg    60
gcggtgagc                                                            69

<210> SEQ ID NO 464
<211> LENGTH: 75
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 464
atgctgaaca aaaaaattat tattattctg acctttattc tgattctgag cattagcagc      60
gcgagcgcga gcgcg                                                       75

<210> SEQ ID NO 465
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
atgggcgtgc tggcgagcgt ggcgggcggc atttttttg aagcgggcat gattgcgacc       60
tgcacc                                                                 66

<210> SEQ ID NO 466
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
atgtttagcg tgagcctgaa caaactgaaa attggccgcg tgtttatttg cctgtttatt      60
ctggtgttta ttagctgcag cattaactgc gtgtttgcg                             99

<210> SEQ ID NO 467
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
atgggcggcg aaattattaa caacgaaaaa ctgaaactga ttctgattct gacc            54

<210> SEQ ID NO 468
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
atggataaaa aaatgattgt gagcgtggcg tttctgctgc tgattctggc ggtggcgctg      60
gtgagcgtgt tgatgaaag caacagc                                           87

<210> SEQ ID NO 469
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
atgaaaatta gccgcattat tgtgctgctg atgattctga ttttaccgc gggcatggtg      60
``` tatgcg                                                                66

<210> SEQ ID NO 470
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
atggatagca aaaaaattct ggtgattctg ggcctgaccg tgctggcgat tttctggcg       60 agcagcgtga gcgcg                                                      75

<210> SEQ ID NO 471
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
atgaaaccgt atgtgattct gattggcagc gcgagcggca ttggcaaaag caccgtggcg     60
gcggaactgg cgaaaaccct gaacattaaa catctggtg                            99

<210> SEQ ID NO 472
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
atgctgatta gcgtgctggg cgtgattgtg attattatta tggtggtggc ggcg           54

<210> SEQ ID NO 473
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
atggcgaccc gcaccaaaca gaccatttgc cgcctgtata gctttcatgg cggccgcttt     60
ctg                                                                   63

<210> SEQ ID NO 474
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
atggaactga gcaaaagcga taaatatctg attgtggtgg gcattatttt ttgcctggcg     60
ctg                                                                   63

<210> SEQ ID NO 475
<211> LENGTH: 66
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 475
atgaaagtgg cgattctggg cgcgggctgc tatcgcaccc atgcggcgag cggcattacc    60
aactttt                                                              66

<210> SEQ ID NO 476
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
atgagcgtga ttctgattct gtttctggcg gtgagcaccg tggcggcg                 48

<210> SEQ ID NO 477
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
atgaacaaaa aactgaaaat tattctgtat attctgctgg cgctgatt                 48

<210> SEQ ID NO 478
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
atggaaacca aaacctgat tattatttgc gcgaccgtga ttctggcggt ggtgattgtg    60
ctgagcgcgt ttatttatgt gaacatgggc aac                                 93

<210> SEQ ID NO 479
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
atgctggtgc tggcgtttgc gattatttt ctgggctata gcattagcct gggcaacaac    60
cag                                                                  63

<210> SEQ ID NO 480
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
atggaactga acgatgaaat tatttttaaa gtggcgctga ttaccgcgct ggtgggcatg    60
```

```
attggc                                                              66

<210> SEQ ID NO 481
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
atgaaaaact attttgatat taaagataaa gtggcggtgg tgaccggcgc gagcagcggc    60
ctgggctggc agatt                                                    75

<210> SEQ ID NO 482
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482 atgacctta acaacctgcg cattaacatt aaagattgca tggtgatttt tgtggtgttt    60
accgtgctgc tgctgagcat tctggcggtg agcgcg                             96

<210> SEQ ID NO 483
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
atgaaattta aaaatatct gtttattctg ctgattgcgc tgatttgcat tattagcgtg     60
agcgcggtgg cg                                                       72

<210> SEQ ID NO 484
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
atggataaaa aaatgaccgt gctgctggtg gcgctgtttt gcctgctgtg cgtgggcagc    60

<210> SEQ ID NO 485
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
atggatcgca aagatattat tattattatt ctggtgctga ttattattag cctgctggcg    60
ctgggcctgc ataaccatca ggtg                                          84

<210> SEQ ID NO 486
<211> LENGTH: 81
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 486
atgaccagcg aaattatgat tctgaccccg accgcggtgg tgctggcggc ggatagcgcg    60
gtgaccatta gcgatattaa a                                              81

<210> SEQ ID NO 487
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
atgcgcaaaa aaattctgtt tctgaccctg atgattctga tttgctttac cctgaacagc    60
gtgtgcgcg                                                            69

<210> SEQ ID NO 488
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
atgcgcctgc gctattttgc gattattagc ctgattctgc tgattttcct ggtgccggtg    60
agctttgcg                                                            69

<210> SEQ ID NO 489
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
atgtttattg gcctgctgct gattggcctg ctgattattc cgattagctt tgcg          54

<210> SEQ ID NO 490
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
atgctgattg gcctggtgat ttgcgcgggc gtgttttatt ttcagtttaa ctatgcgacc    60
ccgacctatc tg                                                        72

<210> SEQ ID NO 491
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
atggtgctgg tggcggtggt ggtgattggc agcaccgcgt ttctgctgaa ctatgatgaa    60
```
accgtgaaat atacc 75

<210> SEQ ID NO 492
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
atggataaaa aaaccctggc gattattgcg attattgtga ttgcgctggt ggcggtgggc 60

<210> SEQ ID NO 493
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
atgaacaaca aaaccctgtt tattattggc ctgtttattt gcctgctgtt taccattccg 60
atggtgagcg cg 72

<210> SEQ ID NO 494
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
atgattaaaa ccgataacaa aggccagatt accgtggaac tgctgctgct gctgagcttt 60

<210> SEQ ID NO 495
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
atgctgaacc gcaaagcgct gattttagc ctgattgtgc tgtttatgct gagcattagc 60
gcggtgagcg cg 72

<210> SEQ ID NO 496
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
atggataaca aagcgattat tggcattgtg attgcgctga ttgtgattgt gctggcgtgc 60
tttgcgtat 69

<210> SEQ ID NO 497
<211> LENGTH: 90
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 497
atgagctatt ttaacaaagg ccatatttgg aacattctgc tgatttgcct gctgattggc      60
accctggcga tgatgggcag cgcgagcgcg                                       90

<210> SEQ ID NO 498
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
atgaaaaaca aagcgatgtt tctgattagc gcgctgctga ttgcggtgat tctgagcctg      60
agcgcggtga gcgcggcgga tgatgcgatt gcg                                   93

<210> SEQ ID NO 499
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
atgaaattta acaaaagcct gattgcgatt tttgtgattc tgattgtggc gtttagcagc      60
attagcgtga ttgcg                                                       75

<210> SEQ ID NO 500
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
atggataaaa aaattattat tggcgcggtg gtggcgctgc tggtgattat tgtgggcgcg      60

<210> SEQ ID NO 501
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
atggaaggcg ataacatggt gaacattaaa accgtggcgc tggcggtg                   48

<210> SEQ ID NO 502
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
atgctgatta tggcgattct ggtgctgctg accatggcga gcgtgagcgc gagcgaactg      60
gaagatattc aggtgacc                                                    78

```
<210> SEQ ID NO 503
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
atgaacaaca ccaccaaaat tctgattggc gtgctgatgg gcctgctg                 48

<210> SEQ ID NO 504
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
atggaaaccg aaaacctgat tattgtgatt ctgctggtgc tgattgcgat ggcgggcatt    60
ttt                                                                  63

<210> SEQ ID NO 505
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
atgtttctgg tgattctgct gtttgcgttt attgtgattg cggcagcta tagcgtgttt    60 gcg                                                                  63

<210> SEQ ID NO 506
<211> LENGTH: 114
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
atggcgctgc tgattctggc gatgagctgc gtgagcgcga gcaacgcgag cgataacctg    60
gatgatctga ccattagcga tagcaacagc ctggatctgg tgagcaccag caac         114

<210> SEQ ID NO 507
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
atgaacaaca aatattttct gggcattatt attattatta ttgcggtg                 48

<210> SEQ ID NO 508
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 508
atgctgctga acgataaaag cgaactgctg aaaagcctga gcattctgtt tctgctgatt      60
gtgctgatta ccagctttaa cagcgtgtat gcg                                    93

<210> SEQ ID NO 509
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
atgaaaaaaa ttattctggg cacctgcatt ctgtttctgc tgattagcgt ggcgtatgcg      60

<210> SEQ ID NO 510
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
atgaaaatta acctgaaacg cgtgattctg ggcattattc tgattctgat ttgcattagc      60
agcgcgagca ttattagcgc g                                                 81

<210> SEQ ID NO 511
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
aaaaaactga ttattattct gctgctgctg attctgctgc tgagcatt                   48

<210> SEQ ID NO 512
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
aaaaaaatta ttattatttt attattatta attttattat taatttcaat t               51

<210> SEQ ID NO 513
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
aaaaaaatta ttattattct gctgctgctg attctgctgc tgattagcat t               51

<210> SEQ ID NO 514
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      6xHis tag

<400> SEQUENCE: 514

His His His His His His
1               5
```